(12) United States Patent
Khanna et al.

(10) Patent No.: US 10,155,027 B2
(45) Date of Patent: *Dec. 18, 2018

(54) ALPHA-GALACTOSIDASE A AND 1-DEOXYGALACTONOJIRIMYCIN CO-FORMULATION FOR THE TREATMENT OF FABRY DISEASE

(71) Applicant: Amicus Therapeutics, Inc., Cranbury, NJ (US)

(72) Inventors: Richie Khanna, Somerset, NJ (US); Kenneth Valenzano, East Brunswick, NJ (US); Susan Elizabeth Fowles, Herts (GB)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/426,583

(22) Filed: Feb. 7, 2017

(65) Prior Publication Data

US 2017/0209548 A1 Jul. 27, 2017

Related U.S. Application Data

(63) Continuation-in-part of application No. 14/415,155, filed as application No. PCT/US2013/050721 on Jul. 16, 2013, now Pat. No. 9,694,056.

(60) Provisional application No. 61/672,566, filed on Jul. 17, 2012.

(51) Int. Cl.
*A61K 38/47* (2006.01)
*A61K 9/00* (2006.01)
*A61K 31/445* (2006.01)

(52) U.S. Cl.
CPC ............ *A61K 38/47* (2013.01); *A61K 9/0019* (2013.01); *A61K 31/445* (2013.01); *C12Y 302/01022* (2013.01)

(58) Field of Classification Search
CPC .................................................... A61K 38/47
See application file for complete search history.

(56) References Cited

U.S. PATENT DOCUMENTS

| 7,446,098 B2 | 11/2008 | Fan |
| 7,750,050 B2 | 6/2010 | Schuchman et al. |
| 7,833,742 B2 | 11/2010 | Treco et al. |
| 7,910,545 B2 | 3/2011 | Meeker et al. |
| 2003/0077806 A1 | 4/2003 | Selden et al. |
| 2006/0153829 A1 | 7/2006 | Fan |
| 2010/0113517 A1 | 5/2010 | Palling |
| 2011/0143419 A1 | 6/2011 | Do |

FOREIGN PATENT DOCUMENTS

| EP | 1171128 B1 | 1/2002 |
| WO | 2004/069190 A2 | 8/2004 |
| WO | 2004/074450 A2 | 9/2004 |
| WO | 2008/121826 A2 | 10/2008 |
| WO | 2008/134628 A2 | 11/2008 |

OTHER PUBLICATIONS

Khanna et al., Molecular Genetics and Metabolism, 2011, 102:S24, abstract.*
Ishii et al., The J of Pharmacology and Experimental Therapeutics, 2009, 328:723-731.*
Frustaci et al., N Engl J Med., 2001, 345(1):25-32.*
Extended European Search Report in PCT/US2013/050721 dated Nov. 30, 2015, 14 pages.
SYPRO Orange Protein Gel Stain (5000X Concentrate in DMSO) Safety Data Sheet, Life Technologies, Jun. 5, 2015, 6 pages.
Benjamin, Elfrida R., et al., "Co-administration With the Pharmacological Chaperone AT1001 Increases Recombinant Human alpha-Galactose A Tissue Uptake and Improves Substrate Reduction in Fabry Mice", Molecular Therapy vol. 20, No. 4, Apr. 2012, 717-726.
Guce, Abigail I., et al., "The Molecular Basis of Pharmacological Chaperoning in Human alpha-Galactosidase", Chemistry & Biology, vol. 18, Dec. 23, 2011, 1521-1526.
Guce, Abigail I., et al., "The Molecular Basis of Pharmacological Chaperoning in Human alpha-Galactosidase", Supplemental Data, Chemistry & Biology vol. 18, Dec. 23, 2011, 12 pages.
Parenti, "Treating lysosomal storage diseases with pharmacological chaperones: from concept to clinics", EMBO Molecular Medicine vol. 1, 2009, 268-279.
Porto, "Synergy between the pharmacological chaperone 1-deoxygalactonojirimycin and the human recombinant alpha-galactosidase A in cultured fibroblasts from patients with Fabry disease", J. Interit. Metab. Dis. vol. 35, 2012, 513-520.
Porto, et al., "The Pharmacological Chaperone N-butyldeoxynokirimycin Enhances Enzyme Replacement Therapy in Pompe Disease Fibroblasts", Molecular Therapy (www.moleculartherapy.org), vol. 17 No. 6, Jun. 2009, 964-971.
Xu, et al., "Conformulation of a Novel Human alpha-Galactosidase A With the Pharmacological Chaperone AT1001 Leads to Improved Substrate Reduction in Fabry Mice", Molecular Therapy vol. 23 No. 7, Jul. 2015, 1169-1181.
Non-Final Office Action in U.S. Appl. No. 14/415,155 dated Jan. 5, 2016, 8 pages.
Final Office Action in U.S. Appl. No. 14/415,155 dated May 31, 2016, 7 pages.
Non-Final Office Action in U.S. Appl. No. 14/415,155 dated Aug. 30, 2016, 8 pages.

* cited by examiner

*Primary Examiner* — Bin Shen
(74) *Attorney, Agent, or Firm* — Servilla Whitney LLC

(57) ABSTRACT

The present application provides compositions comprising α-galactosidase A in combination with an active site-specific chaperone for the α-galactosidase A, and methods for treating Fabry disease in a subject in need thereof, that includes a method of administering to the subject such compositions. The present application also provides methods for increasing the in vitro and in vivo stability of an α-galactosidase A enzyme formulation. The present application also provides methods for treating Fabry disease using intravenous administration of 1-deoxygalactonojirimycin.

19 Claims, 24 Drawing Sheets

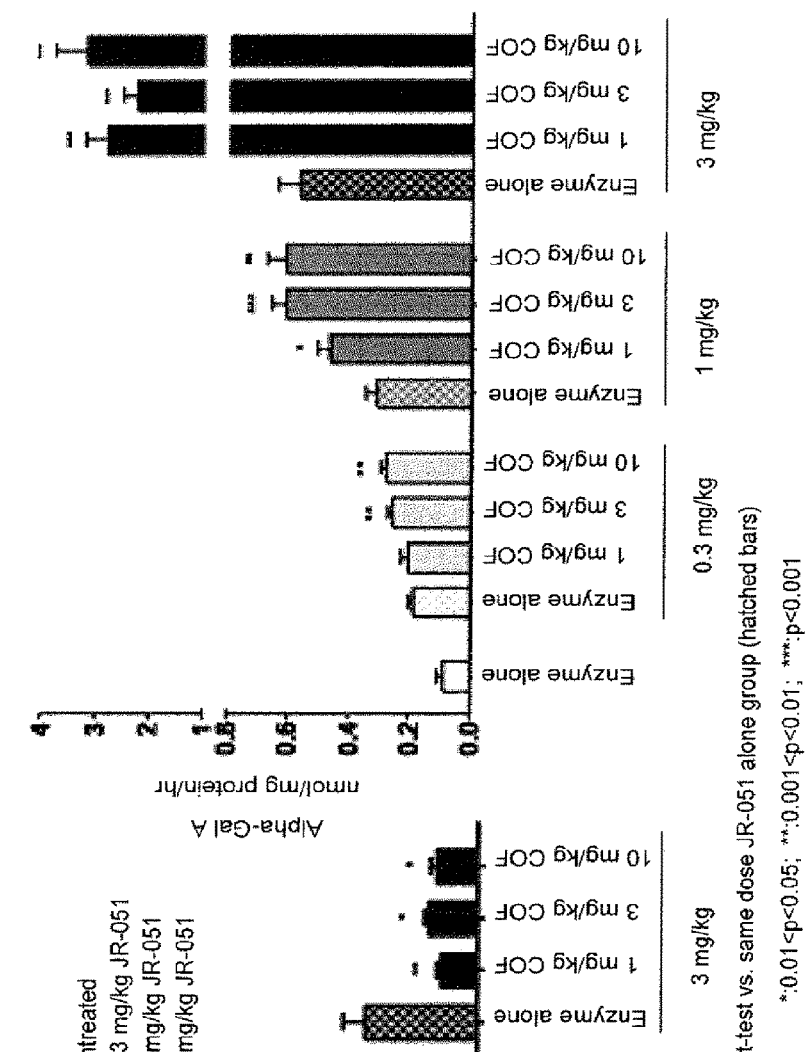
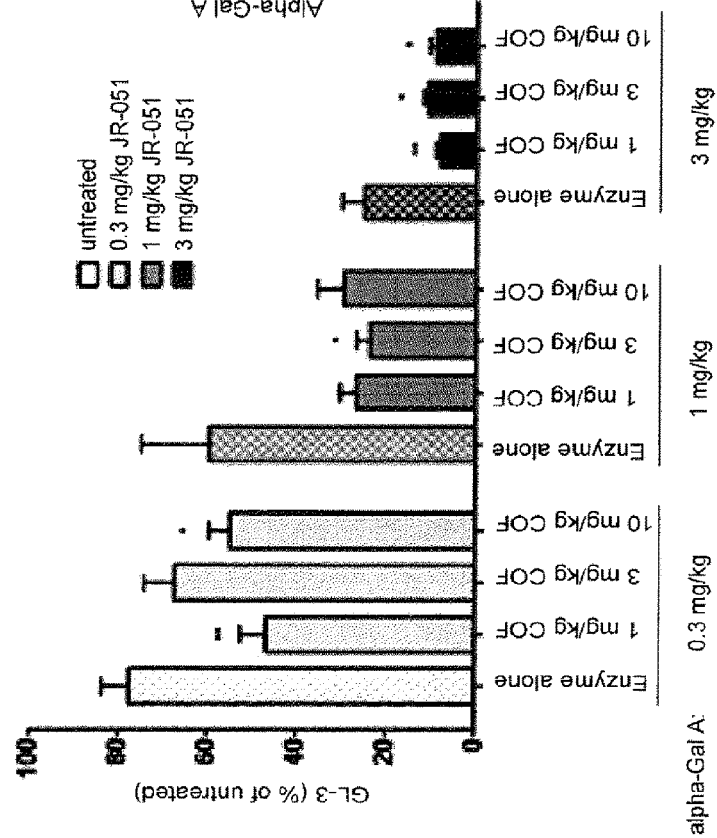
Figure 5A
Figure 5B

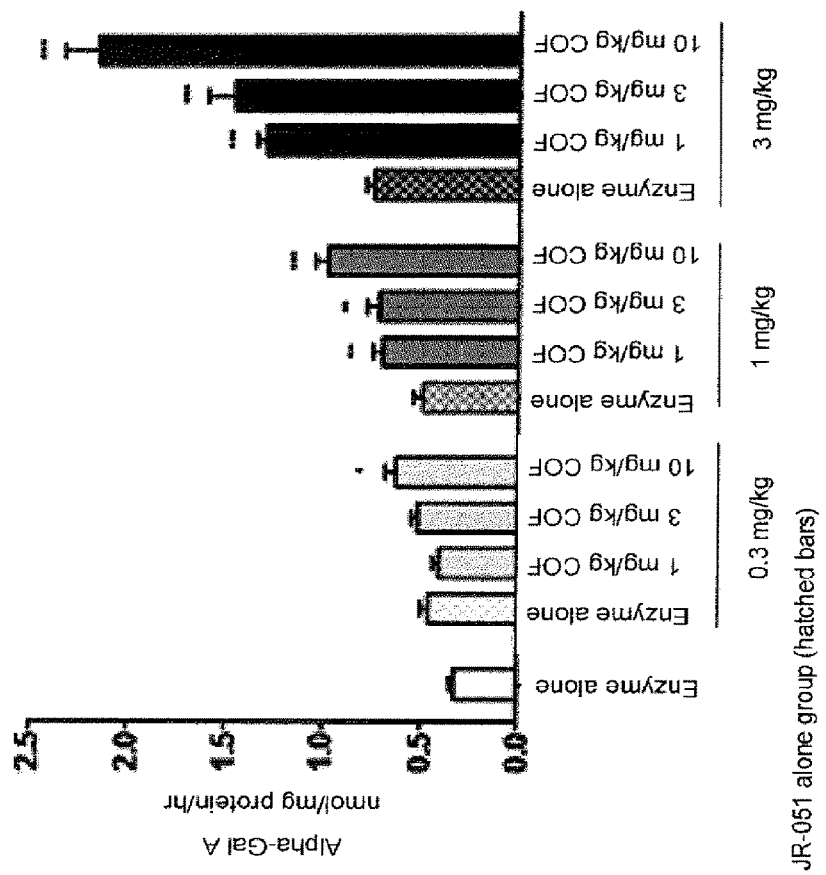
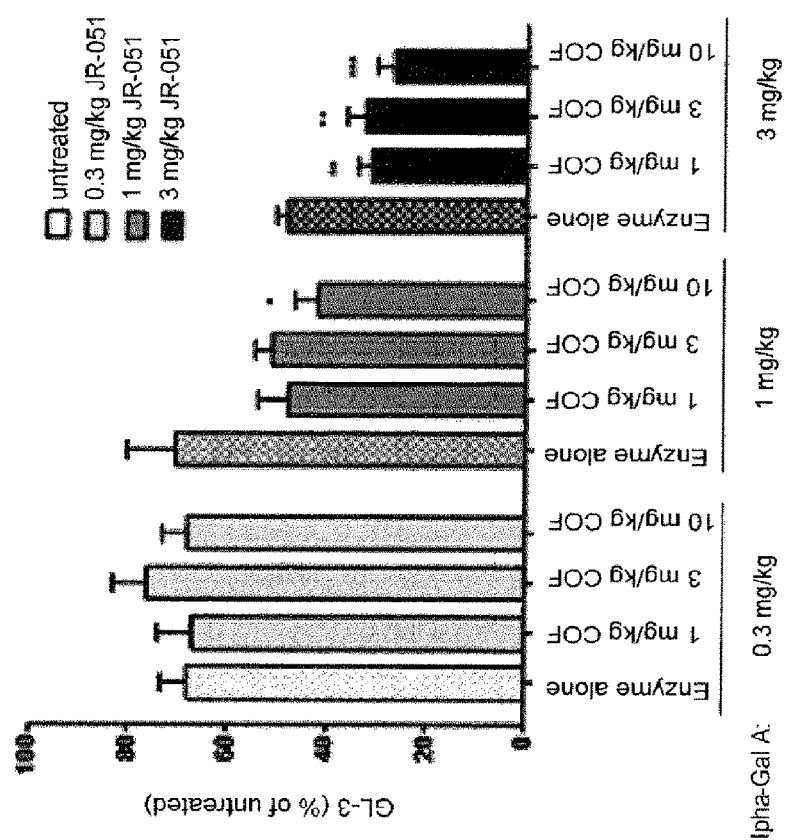
Figure 7A
Figure 7B

Figure 8

| Treatment group (PO; COF) | 0.3 mg/kg JR-051 | 1 mg/kg JR-051 | 3 mg/kg JR-051 |
|---|---|---|---|
| Enzyme alone | 32.0 | 29.4 | 51.6 |
| + 1 mg/kg AT1001 | 33.0 | 52.0 | 68.8** |
| + 3 mg/kg AT1001 | 23.8 | 48.7 | 67.3** |
| + 10 mg/kg AT1001 | 31.9 | 58.0* | 73.0*** |

Data normalized to GL-3 levels in untreated KO mouse kidney (100%; 521 μg/g tissue) and wild-type (0%; 75 μg/g tissue) (% reduction = 100% - % of untreated)

| % Initial Activity | | | | |
|---|---|---|---|---|
| Time (hr) | 5 nM JR051 | 5 nM JR051 10 μM AT1001 | 50 nM JR051 | 50 nM JR051 10 μM AT1001 | 5 nM Fabrazyme |
| 0 | 100.00 | 100.00 | 100.00 | 100.00 | 100.00 |
| 1 | 91.12 | 147.52 | 96.36 | 115.84 | 85.74 |
| 3 | 70.26 | 144.80 | 82.09 | 120.06 | 61.24 |
| 6 | 44.66 | 129.85 | 59.01 | 104.71 | 38.53 |
| 24 | 7.93 | 145.09 | 16.73 | 114.23 | 5.97 |

*p value <0.05, p value <0.01, * p value <0.001 compared to baseline
p value <0.05, ##p value <0.01, ###p value <0.001 compared to enzyme alone

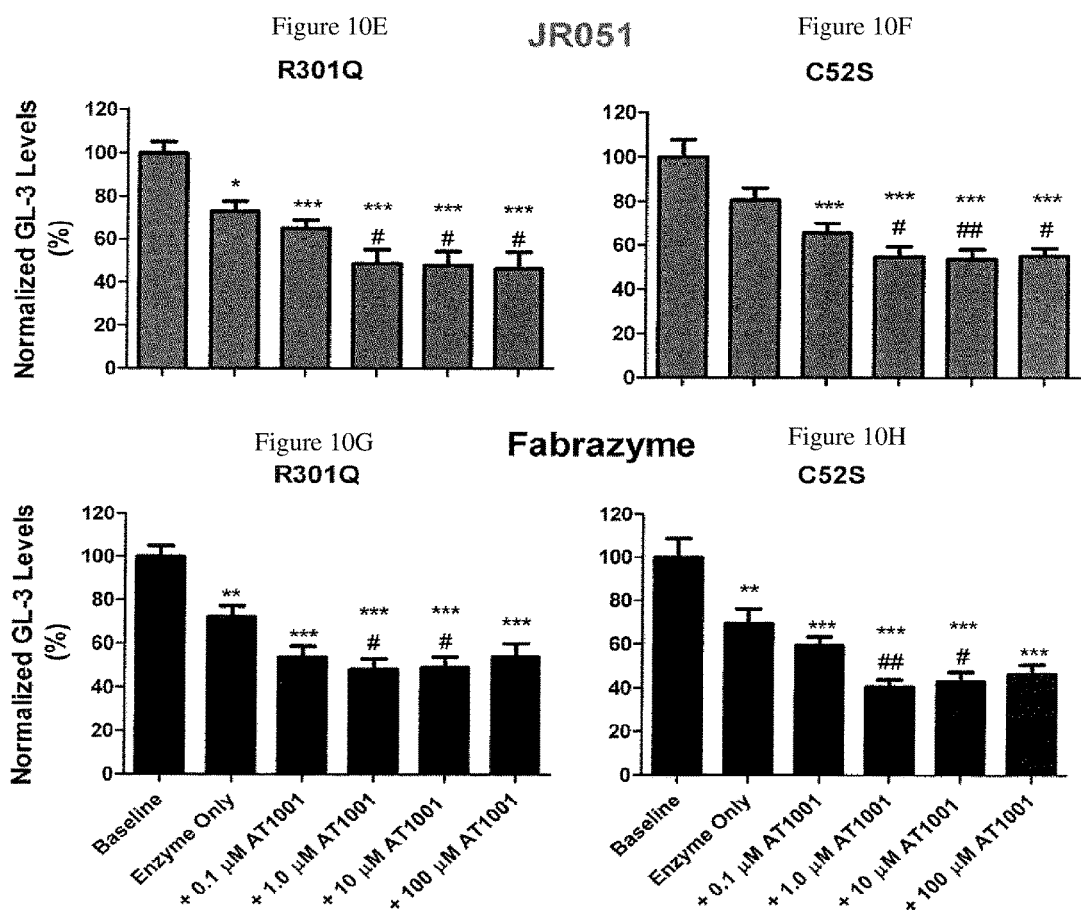
*p value <0.05, *** p value <0.001 compared to baseline; #p value <0.05, ##p value <0.01 compared to enzyme alone

Figure 11A

| Skin | | JR-051 (mg/kg) | | |
|---|---|---|---|---|
| | | 0.5 | 1 | 3 |
| AT1001 (mg/kg) | 0 | 85.7 | 90.7 | 97.4 |
| | 0.3 | 92.5 # | 95.5 | 97.7 |
| | 1 | 90.0 | 95.9 | 98.7 # |
| | 3 | 95.4 # | 97.0 # | 98.7 # |
| | 10 | 94.6 # | 97.6 # | 99.2 # |

Figure 11B

| HEART | | JR-051 (mg/kg) | | |
|---|---|---|---|---|
| | | 0.5 | 1 | 3 |
| AT1001 (mg/kg) | 0 | 72.1 | 82.7 | 93.7 |
| | 0.3 | 82.7 # | 87.9 | 93.5 |
| | 1 | 77.1 | 88.0 | 98.3 # |
| | 3 | 94.7 # | 98.5 # | 98.6 # |
| | 10 | 94.7 # | 97.0 # | 98.6 # |

Figure 11C

| KIDNEY | | JR-051 (mg/kg) | | |
|---|---|---|---|---|
| | | 0.5 | 1 | 3 |
| AT1001 (mg/kg) | 0 | 42.7 | 54.9 | 69.5 |
| | 0.3 | 48.5 | 59.1 | 64.8 |
| | 1 | 40.1 | 58.3 | 78.8 # |
| | 3 | 66.3 # | 79.4 # | 76.0 |
| | 10 | 58.5 # | 64.5 | 77.1 |

ALPHA-GALACTOSIDASE A AND 1-DEOXYGALACTONOJIRIMYCIN CO-FORMULATION FOR THE TREATMENT OF FABRY DISEASE

CROSS-REFERENCE TO RELATED APPLICATION

This application is a continuation-in-part application of U.S. application Ser. No. 14/415,155, filed on Jul. 16, 2013, now U.S. Pat. No. 9,694,056, which is a National Stage Application of PCT/US13/50721, filed on Jul. 16, 2013, which claims priority to U.S. Provisional Application Ser. No. 61/672,566 filed on Jul. 17, 2012, all of which are incorporated by reference herein in their entirety.

1. INTRODUCTION

The present application relates to compositions comprising a co-formulation of an α-galactosidase A enzyme and 1-deoxygalactonojirimycin, and to methods of treating, preventing, and/or ameliorating Fabry Disease by administering such co-formulations to a subject in need of treatment. The present application also relates to the intravenous administration of 1-deoxygalactonojirimycin, and to methods of treating, preventing, and/or ameliorating Fabry Disease by such intravenous administration. The present application also relates to compositions and medicaments which can be used in the treatment of Fabry Disease.

2. BACKGROUND

Fabry disease is a progressive, X-linked inborn error of glycospingolipid metabolism caused by a deficiency in the lysosomal enzyme α-galactosidase A (α-Gal A) as a result of mutations in the α-Gal A gene (GLA). Despite being an X-linked disorder, females can express varying degrees of clinical manifestations. Fabry is a rare disease with incidence estimated between 1 in 40,000 males to 1 in 117,000 in the general population. Moreover, there are variants of later-onset phenotype of Fabry disease that can be under-diagnosed, as they do not present with classical signs and symptoms. This, and the study of newborn screening for Fabry disease, suggests that the actual incidence of Fabry disease can be higher than currently estimated.

Clinical manifestation of the disease can correlate with residual α-Gal A levels. Untreated, life expectancy in Fabry patients is reduced and death usually occurs in the fourth or fifth decade because of vascular disease affecting the kidneys, heart and/or central nervous system. The enzyme deficiency leads to intracellular accumulation of the substrate, globotriaosylceramide (GL-3) in the vascular endothelium and visceral tissues throughout the body. Gradual deterioration of renal function and the development of azotemia, due to glycospingolipid deposition, usually occur in the third to fifth decades of life, but can occur as early as in the second decade. Renal lesions are found in both hemizygous (male) and heterozygous (female) patients.

Cardiac disease occurs in most males and many females. Early cardiac findings include left ventricular enlargement, valvular involvement and conduction abnormalities. Mitral insufficiency is the most frequent valvular lesion typically present in childhood or adolescence. Cerebrovascular manifestations result primarily from multifocal small-vessel involvement and can include thromboses, transient ischemic attacks, basilar artery ischemia and aneurysm, seizures, hemiplegia, hemianesthesia, aphasia, labyrinthine disorders, or cerebral hemorrhages. Average age of onset of cerebrovascular manifestations is 33.8 years. Personality change and psychotic behavior can manifest with increasing age.

The current approved treatment for Fabry disease is enzyme replacement therapy ("ERT"). Two α-Gal A products are currently available for the treatment of Fabry disease: agalsidase alfa (Replagal®, Shire Human Genetic Therapies) and agalsidase beta (Fabrazyme®; Genzyme Corporation). These two forms of ERT are intended to compensate for a patient's inadequate α-Gal A activity with a recombinant form of the enzyme, administered intravenously. While ERT is effective in many settings, the treatment also has limitations. ERT has not been demonstrated to decrease the risk of stroke, cardiac muscle responds slowly, and GL-3 elimination from some of the cell types of the kidneys is limited. Some patients develop immune reactions to ERT.

1-deoxygalactonojirimycin and its salt, 1-deoxygalactonojirimycin hydrochloride (also known by its United States Adopted Name (USAN), migalastat hydrochloride) acts as a pharmacological chaperone for mutant α-Gal A by selectively binding to the enzyme, thereby increasing its stability and helping the enzyme fold into its correct three-dimensional shape. This stabilization of α-Gal A allows the cell's quality control mechanisms to recognize the enzyme as properly folded so that trafficking of the enzyme to the lysosome is increased, allowing it to carry out its intended biological function, the metabolism of GL-3. As a result of restoring the proper trafficking of α-Gal A from the ER to the lysosome, migalastat hydrochloride also reduces the accumulation of misfolded protein in the ER, which can alleviate stress on cells and some inflammatory-like responses that can be contributing factors in Fabry disease. Multiple in vitro and in vivo preclinical studies, as well as clinical studies, of migalastat hydrochloride have been conducted. Migalastat hydrochloride has been shown to increase the amount of intracellular α-Gal A protein and to enhance transport of mutant enzyme to the lysosome.

3. SUMMARY OF THE APPLICATION

The present application relates to compositions for the treatment of Fabry Disease comprising an α-galactosidase A (α-Gal A) enzyme (e.g., a recombinant human α-Gal A (rhα-Gal A)) in combination with an Active Site-Specific Chaperone (ASSC) for the α-Gal A enzyme (e.g., 1-deoxygalactonojirimycin (DGJ)).

The present application also relates to methods for the treatment of Fabry Disease, by administering to a subject in need of such treatment an α-Gal A enzyme, in combination with an Active Site-Specific Chaperone (ASSC) for the α-Gal A enzyme (e.g., 1-deoxygalactonojirimycin (DGJ)).

The present application also provides a combined formulation of an α-Gal A enzyme and an Active Site-Specific Chaperone (ASSC) for the α-Gal A enzyme (e.g., 1-deoxygalactonojirimycin (DGJ)) for use in the treatment of Fabry disease.

The present application also provides the use of an α-Gal A enzyme and an Active Site-Specific Chaperone (ASSC) for the α-Gal A enzyme (e.g., 1-deoxygalactonojirimycin (DGJ)) in the preparation of a medicament for the treatment of Fabry disease, wherein the treatment comprises administering a composition comprising a co-formulation of the α-Gal A enzyme and the ASSC for the α-Gal A enzyme to a subject in need thereof.

The present application also relates to methods for the treatment of Fabry Disease, by intravenously administering 1-deoxygalactonojirimycin (DGJ) or a pharmaceutically acceptable salt thereof, to a subject in need of such treatment.

In one or more embodiments, the 1-deoxygalactonojirimycin is 1-deoxygalactonojirimycin-hydrochloride (DGJ-HCl), also known as migalastat hydrochloride.

In certain embodiments, the dosage of DGJ or salt thereof is selected from of about 0.1 to about 15 mg/kg.

In certain embodiments, the dosage of DGJ or salt thereof is selected from the group consisting of about 0.1, 0.3, 1, 3, and 10 mg/kg.

In certain embodiments, the dosage of DGJ or salt thereof is about 0.3 to about 10 mg/kg.

In certain embodiments, the DGJ or salt thereof is administered once per day, once every two days, once every three days, once every four days, once every five days, once every six days, or once every seven days.

In one or more embodiments, the patient is also intravenously administered a recombinant human α-galactosidase A.

In one or more embodiments, the α-Gal A enzyme is agalsidase alfa or agalsidase beta.

In certain embodiments, the α-Gal A enzyme is combined with DGJ to create a co-formulation prior to administration to a subject.

In certain embodiments, the co-formulation of an α-Gal A enzyme and an Active Site-Specific Chaperone (ASSC) for the α-Gal A enzyme (e.g., 1-deoxygalactonojirimycin (DGJ)) is presented for parenteral administration. In one embodiment administration is by single or repeated intravenous bolus injections of the co-formulation. In one embodiment administration is by intravenous infusion of the co-formulation.

In certain embodiments, the α-Gal A enzyme is combined with DGJ at a concentration of between about 0.5 and about 20 μM. In certain embodiments, the α-Gal A enzyme is combined with DGJ at a concentration of about 1.2, 2, 4, 8, or 12 μM.

In certain embodiments, DGJ is combined with the α-Gal A enzyme at a concentration of between about 50 and about 20,000 μM. In certain embodiments, DGJ is combined with the α-Gal A enzyme at a concentration of about 449, 748, 1,495, 4,490, or 14,950 μM.

In certain embodiments, the compositions of the application comprise about 1.2 μM α-Gal A enzyme and about 449 μM DGJ.

In certain embodiments, the compositions of the application comprise about 1.2 μM α-Gal A enzyme and about 748 μM DGJ.

In certain embodiments, the compositions of the application comprise about 1.2 μM α-Gal A enzyme and about 1,495 μM DGJ.

In certain embodiments, the compositions of the application comprise about 1.2 μM α-Gal A enzyme and about 4,490 μM DGJ.

In certain embodiments, the compositions of the application comprise about 1.2 μM α-Gal A enzyme and about 14,950 μM DGJ.

In certain embodiments, the compositions of the application comprise about 2 μM α-Gal A enzyme and about 449 μM DGJ.

In certain embodiments, the compositions of the application comprise about 2 μM α-Gal A enzyme and about 748 μM DGJ.

In certain embodiments, the compositions of the application comprise about 2 μM α-Gal A enzyme and about 1,495 μM DGJ.

In certain embodiments, the compositions of the application comprise about 2 μM α-Gal A enzyme and about 4,490 μM DGJ.

In certain embodiments, the compositions of the application comprise about 2 μM α-Gal A enzyme and about 14,950 μM DGJ.

In certain embodiments, the compositions of the application comprise about 4 μM α-Gal A enzyme and about 449 μM DGJ.

In certain embodiments, the compositions of the application comprise about 4 μM α-Gal A enzyme and about 748 μM DGJ.

In certain embodiments, the compositions of the application comprise about 4 μM α-Gal A enzyme and about 1,495 μM DGJ.

In certain embodiments, the compositions of the application comprise about 4 μM α-Gal A enzyme and about 4,490 μM DGJ.

In certain embodiments, the compositions of the application comprise about 4 μM α-Gal A enzyme and about 14,950 μM DGJ.

In certain embodiments, the compositions of the application comprise about 8 μM α-Gal A enzyme and about 449 μM DGJ.

In certain embodiments, the compositions of the application comprise about 8 μM α-Gal A enzyme and about 748 μM DGJ.

In certain embodiments, the compositions of the application comprise about 8 μM α-Gal A enzyme and about 1,495 μM DGJ.

In certain embodiments, the compositions of the application comprise about 8 μM α-Gal A enzyme and about 4,490 μM DGJ.

In certain embodiments, the compositions of the application comprise about 8 μM α-Gal A enzyme and about 14,950 μM DGJ.

In certain embodiments, the compositions of the application comprise about 12 μM α-Gal A enzyme and about 449 μM DGJ.

In certain embodiments, the compositions of the application comprise about 12 μM α-Gal A enzyme and about 748 μM DGJ.

In certain embodiments, the compositions of the application comprise about 12 μM α-Gal A enzyme and about 1,495 μM DGJ.

In certain embodiments, the compositions of the application comprise about 12 μM α-Gal A enzyme and about 4,490 μM DGJ.

In certain embodiments, the compositions of the application comprise about 12 μM α-Gal A enzyme and about 14,950 μM DGJ.

The present invention also provides the use of a co-formulation of between about 0.5 and about 20 μM α-Gal A and between about 50 and about 20,000 μM DGJ or a pharmaceutically acceptable salt thereof in the preparation of a medicament for the treatment of Fabry disease, wherein the medicament is formulated for parenteral administration to a subject.

The present invention also provides the use of a co-formulation of about 1.2, 2, 4, 8, or 12 μM α-Gal A and about 449, 748, 1,495, 4,490, or 14,950 μM DGJ or a pharmaceutically acceptable salt thereof in the preparation of a medicament for the treatment of Fabry disease, wherein the medicament is formulated for parenteral administration to a subject.

The present invention also provides a co-formulation of between about 0.5 and about 20 μM α-Gal A and between about 50 and about 20,000 μM DGJ or a pharmaceutically acceptable salt thereof for use in the treatment of Fabry disease, wherein the co-formulation is administered parenterally.

The present invention also provides a co-formulation of about 1.2, 2, 4, 8, or 12 μM α-Gal A and about 449, 748, 1,495, 4,490, or 14,950 μM DGJ or a pharmaceutically acceptable salt thereof for use in the treatment of Fabry disease, wherein the co-formulation is administered parenterally.

In certain embodiments, the α-Gal A enzyme and DGJ are combined to create a co-formulation with a molar ratio of DGJ to α-Gal A enzyme of between about 13,000:1 and about 50:1, or between about 10,000:1 and about 75:1, or between about 1,000:1 and about 100:1.

In certain embodiments, the α-Gal A enzyme and DGJ are combined to create a co-formulation for administration to a subject, wherein the dosage of α-Gal A enzyme of the co-formulation administered to the subject is between about 0.1 and about 5 mg/kg. In certain embodiments, the dosage of α-Gal A enzyme of the co-formulation administered to the subject is about 0.3, 0.5, 1, 2 or 3 mg/kg.

In certain embodiments, the α-Gal A enzyme and DGJ are combined to create a co-formulation for administration to a subject, wherein the dosage of DGJ of the co-formulation administered to the subject is between about 0.1 and about 15 mg/kg. In certain embodiments, the dosage of DGJ of the co-formulation administered to the subject is about 0.1, 0.3, 0.5, 1, 3, or 10 mg/kg.

In certain embodiments, the α-Gal A enzyme and DGJ are combined to create a co-formulation for administration to a subject, wherein the dosage of α-Gal A enzyme administered to the subject is about 0.3 mg/kg, and the dosage of DGJ administered to the subject is about 0.1 mg/kg.

In certain embodiments, the α-Gal A enzyme and DGJ are combined to create a co-formulation for administration to a subject, wherein the dosage of α-Gal A enzyme administered to the subject is about 0.3 mg/kg, and the dosage of DGJ administered to the subject is about 0.3 mg/kg.

In certain embodiments, the α-Gal A enzyme and DGJ are combined to create a co-formulation for administration to a subject, wherein the dosage of α-Gal A enzyme administered to the subject is about 0.3 mg/kg, and the dosage of DGJ administered to the subject is about 0.5 mg/kg.

In certain embodiments, the α-Gal A enzyme and DGJ are combined to create a co-formulation for administration to a subject, wherein the dosage of α-Gal A enzyme administered to the subject is about 0.3 mg/kg, and the dosage of DGJ administered to the subject is about 1 mg/kg.

In certain embodiments, the α-Gal A enzyme and DGJ are combined to create a co-formulation for administration to a subject, wherein the dosage of α-Gal A enzyme administered to the subject is about 0.3 mg/kg, and the dosage of DGJ administered to the subject is about 3 mg/kg.

In certain embodiments, the α-Gal A enzyme and DGJ are combined to create a co-formulation for administration to a subject, wherein the dosage of α-Gal A enzyme administered to the subject is about 0.3 mg/kg, and the dosage of DGJ administered to the subject is about 10 mg/kg.

In certain embodiments, the α-Gal A enzyme and DGJ are combined to create a co-formulation for administration to a subject, wherein the dosage of α-Gal A enzyme administered to the subject is about 0.5 mg/kg, and the dosage of DGJ administered to the subject is about 0.1 mg/kg.

In certain embodiments, the α-Gal A enzyme and DGJ are combined to create a co-formulation for administration to a subject, wherein the dosage of α-Gal A enzyme administered to the subject is about 0.5 mg/kg, and the dosage of DGJ administered to the subject is about 0.3 mg/kg.

In certain embodiments, the α-Gal A enzyme and DGJ are combined to create a co-formulation for administration to a subject, wherein the dosage of α-Gal A enzyme administered to the subject is about 0.5 mg/kg, and the dosage of DGJ administered to the subject is about 0.5 mg/kg.

In certain embodiments, the α-Gal A enzyme and DGJ are combined to create a co-formulation for administration to a subject, wherein the dosage of α-Gal A enzyme administered to the subject is about 0.5 mg/kg, and the dosage of DGJ administered to the subject is about 1 mg/kg.

In certain embodiments, the α-Gal A enzyme and DGJ are combined to create a co-formulation for administration to a subject, wherein the dosage of α-Gal A enzyme administered to the subject is about 0.5 mg/kg, and the dosage of DGJ administered to the subject is about 3 mg/kg.

In certain embodiments, the α-Gal A enzyme and DGJ are combined to create a co-formulation for administration to a subject, wherein the dosage of α-Gal A enzyme administered to the subject is about 0.5 mg/kg, and the dosage of DGJ administered to the subject is about 10 mg/kg.

In certain embodiments, the α-Gal A enzyme and DGJ are combined to create a co-formulation for administration to a subject, wherein the dosage of α-Gal A enzyme administered to the subject is about 1 mg/kg, and the dosage of DGJ administered to the subject is about 0.1 mg/kg.

In certain embodiments, the α-Gal A enzyme and DGJ are combined to create a co-formulation for administration to a subject, wherein the dosage of α-Gal A enzyme administered to the subject is about 1 mg/kg, and the dosage of DGJ administered to the subject is about 0.3 mg/kg.

In certain embodiments, the α-Gal A enzyme and DGJ are combined to create a co-formulation for administration to a subject, wherein the dosage of α-Gal A enzyme administered to the subject is about 1 mg/kg, and the dosage of DGJ administered to the subject is about 0.5 mg/kg.

In certain embodiments, the α-Gal A enzyme and DGJ are combined to create a co-formulation for administration to a subject, wherein the dosage of α-Gal A enzyme administered to the subject is about 1 mg/kg, and the dosage of DGJ administered to the subject is about 1 mg/kg.

In certain embodiments, the α-Gal A enzyme and DGJ are combined to create a co-formulation for administration to a subject, wherein the dosage of α-Gal A enzyme administered to the subject is about 1 mg/kg, and the dosage of DGJ administered to the subject is about 3 mg/kg.

In certain embodiments, the α-Gal A enzyme and DGJ are combined to create a co-formulation for administration to a subject, wherein the dosage of α-Gal A enzyme administered to the subject is about 1 mg/kg, and the dosage of DGJ administered to the subject is about 10 mg/kg.

In certain embodiments, the α-Gal A enzyme and DGJ are combined to create a co-formulation for administration to a subject, wherein the dosage of α-Gal A enzyme administered to the subject is about 2 mg/kg, and the dosage of DGJ administered to the subject is about 0.1 mg/kg.

In certain embodiments, the α-Gal A enzyme and DGJ are combined to create a co-formulation for administration to a subject, wherein the dosage of α-Gal A enzyme administered to the subject is about 2 mg/kg, and the dosage of DGJ administered to the subject is about 0.3 mg/kg.

In certain embodiments, the α-Gal A enzyme and DGJ are combined to create a co-formulation for administration to a subject, wherein the dosage of α-Gal A enzyme administered to the subject is about 2 mg/kg, and the dosage of DGJ administered to the subject is about 0.5 mg/kg.

In certain embodiments, the α-Gal A enzyme and DGJ are combined to create a co-formulation for administration to a subject, wherein the dosage of α-Gal A enzyme administered to the subject is about 2 mg/kg, and the dosage of DGJ administered to the subject is about 1 mg/kg.

In certain embodiments, the α-Gal A enzyme and DGJ are combined to create a co-formulation for administration to a subject, wherein the dosage of α-Gal A enzyme administered to the subject is about 2 mg/kg, and the dosage of DGJ administered to the subject is about 3 mg/kg.

In certain embodiments, the α-Gal A enzyme and DGJ are combined to create a co-formulation for administration to a subject, wherein the dosage of α-Gal A enzyme administered to the subject is about 2 mg/kg, and the dosage of DGJ administered to the subject is about 10 mg/kg.

In certain embodiments, the α-Gal A enzyme and DGJ are combined to create a co-formulation for administration to a subject, wherein the dosage of α-Gal A enzyme administered to the subject is about 3 mg/kg, and the dosage of DGJ administered to the subject is about 0.1 mg/kg. In certain embodiments, the α-Gal A enzyme and DGJ are combined to create a co-formulation for administration to a subject, wherein the dosage of α-Gal A enzyme administered to the subject is about 3 mg/kg, and the dosage of DGJ administered to the subject is about 0.3 mg/kg.

In certain embodiments, the α-Gal A enzyme and DGJ are combined to create a co-formulation for administration to a subject, wherein the dosage of α-Gal A enzyme administered to the subject is about 3 mg/kg, and the dosage of DGJ administered to the subject is about 0.5 mg/kg.

In certain embodiments, the α-Gal A enzyme and DGJ are combined to create a co-formulation for administration to a subject, wherein the dosage of α-Gal A enzyme administered to the subject is about 3 mg/kg, and the dosage of DGJ administered to the subject is about 1 mg/kg.

In certain embodiments, the α-Gal A enzyme and DGJ are combined to create a co-formulation for administration to a subject, wherein the dosage of α-Gal A enzyme administered to the subject is about 3 mg/kg, and the dosage of DGJ administered to the subject is about 3 mg/kg.

In certain embodiments, the α-Gal A enzyme and DGJ are combined to create a co-formulation for administration to a subject, wherein the dosage of α-Gal A enzyme administered to the subject is about 3 mg/kg, and the dosage of DGJ administered to the subject is about 10 mg/kg.

The present invention also provides the use of a co-formulation of α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount between about 0.1 and about 0.5 mg/kg, and the DGJ of the co-formulation is formulated for administration in an amount between about 0.1 and about 15 mg/kg.

The present invention also provides the use of a co-formulation of α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount of about 0.3, 0.5, 1, 2 or 3 mg/kg, and the DGJ of the co-formulation is formulated for administration in an amount of about 0.1, 0.3, 0.5, 1, 3, or 10 mg/kg.

The present invention also provides a co-formulation of α-Gal A and DGJ or a pharmaceutically acceptable salt thereof for use in the treatment of Fabry disease, wherein the co-formulation is administered parenterally, and wherein the α-Gal A of the co-formulation is administered in an amount between about 0.1 and about 0.5 mg/kg, and the DGJ of the co-formulation is administered in an amount between about 0.1 and about 15 mg/kg.

The present invention also provides a co-formulation of α-Gal A and DGJ or a pharmaceutically acceptable salt thereof for use in the treatment of Fabry disease, wherein the co-formulation is administered parenterally, and wherein the α-Gal A of the co-formulation is administered in an amount of about 0.3, 0.5, 1, 2 or 3 mg/kg, and the DGJ of the co-formulation is administered in an amount of about 0.1, 0.3, 0.5, 1, 3, or 10 mg/kg.

According to one aspect of the application, methods of enhancing delivery of α-Gal A to tissues, for example heart, kidney or skin tissue, of an individual with Fabry disease are provided. The methods include administering α-Gal A in combination with an ASSC intravenously to the individual, wherein the α-Gal A and ASSC are present in a co-formulation. In some embodiments, the α-Gal A in combination with an ASSC is administered in a sufficient dose to result in a peak concentration of α-Gal A in plasma and/or tissues of the subject within about 24 hours after the administration of the dose. In certain embodiments, the α-Gal A in combination with an ASSC is administered in a sufficient dose to result in a peak concentration of α-Gal A in plasma and/or tissues of the subject within about 0.2 to about 50 hours, or about 40, 30, 20, 10, 5, 1, 0.5 or fewer hours after the administration of the dose. In some embodiments, the dose does not result in a toxic level of α-Gal A in the liver of the individual.

The present application further provides a method for increasing the stability of an α-Gal A enzyme in a proper conformation, in vivo and in vitro. In one embodiment, an α-Gal A enzyme (e.g., a recombinant human α-Gal A (rhα-Gal A)) in combination with an ASSC for the α-Gal A enzyme (e.g., 1-deoxygalactonojirimycin) is administered to an individual in need of such treatment. The α-Gal A enzyme is stabilized conformationally when combined with an ASSC and is well-suited to withstand, for example, thermal and pH challenges.

In certain embodiments, the co-formulation compositions of the present application are stable at a pH equal to or greater than about pH 5, 6 or 7.

In certain embodiments, the co-formulations of the application maintain physical and chemical stability over extended periods, and have a viscosity suitable for intravenous administration.

In various non-limiting embodiments, the ASSC for the α-Gal A enzyme is a small molecule inhibitor of the α-Gal A enzyme, including reversible competitive inhibitors of the α-Gal A enzyme.

In one particular non-limiting embodiment, the ASSC is 1-deoxygalactonojirimycin (DGJ), or a pharmaceutically acceptable salt, ester or prodrug of 1-deoxygalactonojirimycin. In one embodiment, the salt is hydrochloride salt (i.e., 1-deoxygalactonojirimycin-HCl).

In one particular non-limiting embodiment, a combined formulation of recombinant human α-Gal A (rhα-Gal A)) with 1-deoxygalactonojirimycin-HCl is provided for intravenous administration to a patient in need thereof at a dose of 0.3 mg/kg rhα-Gal A and 0.1 mg/kg 1-deoxygalactonojirimycin (as the HCl salt).

In a further embodiment, a combined formulation of recombinant human α-Gal A (rhα-Gal A)) with 1-deoxygalactonojirimycin-HCl is provided for intravenous administration to a patient in need thereof at a dose of 0.3 mg/kg rhα-Gal A and 0.3 mg/kg 1-deoxygalactonojirimycin (as the HCl salt).

In a further embodiment the co-formulation is provided for intravenous administration to a patient in need thereof at a dose of 0.3 mg/kg rhα-Gal A and 0.5 mg/kg 1-deoxygalactonojirimycin (as the HCl salt).

In a further embodiment the co-formulation is provided for intravenous administration to a patient in need thereof at a dose of 0.3 mg/kg rhα-Gal A and 1 mg/kg 1-deoxygalactonojirimycin (as the HCl salt).

In a further embodiment the co-formulation is provided for intravenous administration to a patient in need thereof at a dose of 0.3 mg/kg rhα-Gal A and 3 mg/kg 1-deoxygalactonojirimycin (as the HCl salt).

In a further embodiment the co-formulation is provided for intravenous administration to a patient in need thereof at a dose of 0.3 mg/kg rhα-Gal A and 10 mg/kg 1-deoxygalactonojirimycin (as the HCl salt).

In a further embodiment the co-formulation is provided for intravenous administration to a patient in need thereof at a dose of 0.5 mg/kg rhα-Gal A and 0.1 mg/kg 1-deoxygalactonojirimycin (as the HCl salt).

In a further embodiment the co-formulation is provided for intravenous administration to a patient in need thereof at a dose of 0.5 mg/kg rhα-Gal A and 0.3 mg/kg 1-deoxygalactonojirimycin (as the HCl salt).

In a further embodiment the co-formulation is provided for intravenous administration to a patient in need thereof at a dose of 0.5 mg/kg rhα-Gal A and 0.5 mg/kg 1-deoxygalactonojirimycin (as the HCl salt).

In a further embodiment the co-formulation is provided for intravenous administration to a patient in need thereof at a dose of 0.5 mg/kg rhα-Gal A and 1 mg/kg 1-deoxygalactonojirimycin (as the HCl salt).

In a further embodiment the co-formulation is provided for intravenous administration to a patient in need thereof at a dose of 0.5 mg/kg rhα-Gal A and 3 mg/kg 1-deoxygalactonojirimycin (as the HCl salt).

In a further embodiment the co-formulation is provided for intravenous administration to a patient in need thereof at a dose of 0.5 mg/kg rhα-Gal A and 10 mg/kg 1-deoxygalactonojirimycin (as the HCl salt).

In a further embodiment the co-formulation is provided for intravenous administration to a patient in need thereof at a dose of 1 mg/kg rhα-Gal A and 0.1 mg/kg 1-deoxygalactonojirimycin (as the HCl salt).

In a further embodiment the co-formulation is provided for intravenous administration to a patient in need thereof at a dose of 1 mg/kg rhα-Gal A and 0.3 mg/kg 1-deoxygalactonojirimycin (as the HCl salt).

In a further embodiment the co-formulation is provided for intravenous administration to a patient in need thereof at a dose of 1 mg/kg rhα-Gal A and 0.5 mg/kg 1-deoxygalactonojirimycin (as the HCl salt).

In a further embodiment the co-formulation is provided for intravenous administration to a patient in need thereof at a dose of 1 mg/kg rhα-Gal A and 1 mg/kg 1-deoxygalactonojirimycin (as the HCl salt).

In a further embodiment the co-formulation is provided for intravenous administration to a patient in need thereof at a dose of 1 mg/kg rhα-Gal A and 3 mg/kg 1-deoxygalactonojirimycin (as the HCl salt).

In a further embodiment the co-formulation is provided for intravenous administration to a patient in need thereof at a dose of 1 mg/kg rhα-Gal A and 10 mg/kg 1-deoxygalactonojirimycin (as the HCl salt).

In a further embodiment the co-formulation is provided for intravenous administration to a patient in need thereof at a dose of 2 mg/kg rhα-Gal A and 0.1 mg/kg 1-deoxygalactonojirimycin (as the HCl salt).

In a further embodiment the co-formulation is provided for intravenous administration to a patient in need thereof at a dose of 2 mg/kg rhα-Gal A and 0.3 mg/kg 1-deoxygalactonojirimycin (as the HCl salt).

In a further embodiment the co-formulation is provided for intravenous administration to a patient in need thereof at a dose of 2 mg/kg rhα-Gal A and 0.5 mg/kg 1-deoxygalactonojirimycin (as the HCl salt).

In a further embodiment the co-formulation is provided for intravenous administration to a patient in need thereof at a dose of 2 mg/kg rhα-Gal A and 1 mg/kg 1-deoxygalactonojirimycin (as the HCl salt).

In a further embodiment the co-formulation is provided for intravenous administration to a patient in need thereof at a dose of 2 mg/kg rhα-Gal A and 3 mg/kg 1-deoxygalactonojirimycin (as the HCl salt).

In a further embodiment the co-formulation is provided for intravenous administration to a patient in need thereof at a dose of 2 mg/kg rhα-Gal A and 10 mg/kg 1-deoxygalactonojirimycin (as the HCl salt).

In a further embodiment the co-formulation is provided for intravenous administration to a patient in need thereof at a dose of 3 mg/kg rhα-Gal A and 0.1 mg/kg 1-deoxygalactonojirimycin (as the HCl salt).

In a further embodiment the co-formulation is provided for intravenous administration to a patient in need thereof at a dose of 3 mg/kg rhα-Gal A and 0.3 mg/kg 1-deoxygalactonojirimycin (as the HCl salt).

In a further embodiment the co-formulation is provided for intravenous administration to a patient in need thereof at a dose of 3 mg/kg rhα-Gal A and 0.5 mg/kg 1-deoxygalactonojirimycin (as the HCl salt).

In a further embodiment the co-formulation is provided for intravenous administration to a patient in need thereof at a dose of 3 mg/kg rhα-Gal A and 1 mg/kg 1-deoxygalactonojirimycin (as the HCl salt).

In a further embodiment the co-formulation is provided for intravenous administration to a patient in need thereof at a dose of 3 mg/kg rhα-Gal A and 3 mg/kg 1-deoxygalactonojirimycin (as the HCl salt).

In a further embodiment the co-formulation is provided for intravenous administration to a patient in need thereof at a dose of 3 mg/kg rhα-Gal A and 10 mg/kg 1-deoxygalactonojirimycin (as the HCl salt).

The present invention also provides the use of a co-formulation of α-Gal A and DGJ or a pharmaceutically acceptable salt thereof in the preparation of a medicament for the treatment of Fabry disease, wherein the medicament is formulated for intravenous administration to a subject, and wherein the α-Gal A of the co-formulation is formulated for administration in an amount of about 0.3, 0.5, 1, 2 or 3 mg/kg, and the DGJ (as the HCl salt) of the co-formulation is formulated for administration in an amount of about 0.1, 0.3, 0.5, 1, 3, or 10 mg/kg.

The present invention also provides a co-formulation of α-Gal A and DGJ or a pharmaceutically acceptable salt thereof for use in the treatment of Fabry disease, wherein the co-formulation is administered intravenously, and wherein the α-Gal A of the co-formulation is administered in an amount of about 0.3, 0.5, 1, 2 or 3 mg/kg, and the DGJ (as the HCl salt) of the co-formulation is administered in an amount of about 0.1, 0.3, 0.5, 1, 3, or 10 mg/kg.

The present application also provides a kit for treating Fabry disease in a subject, the kit comprising from between about 0.5 and 20 µM of an α-Gal A enzyme, and from between about 50 and about 20,000 µM of 1-deoxygalactonojirimycin.

4. BRIEF DESCRIPTION OF THE DRAWINGS

Figure 3A:
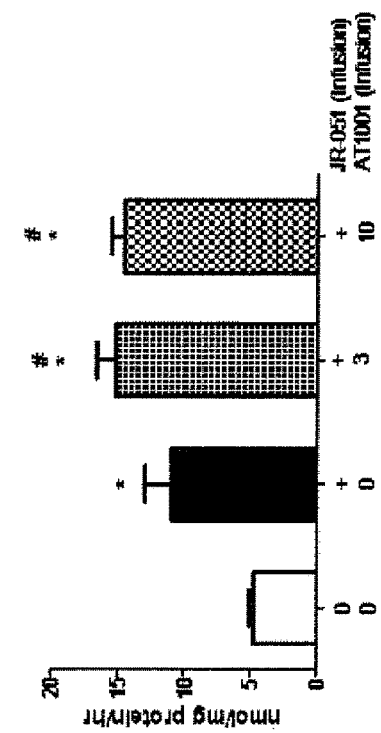
Figure 3A:
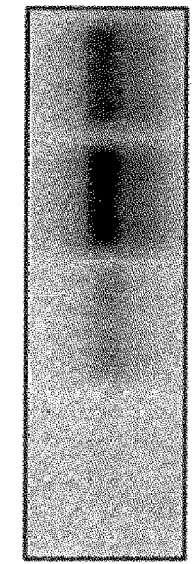
Figure 3B:
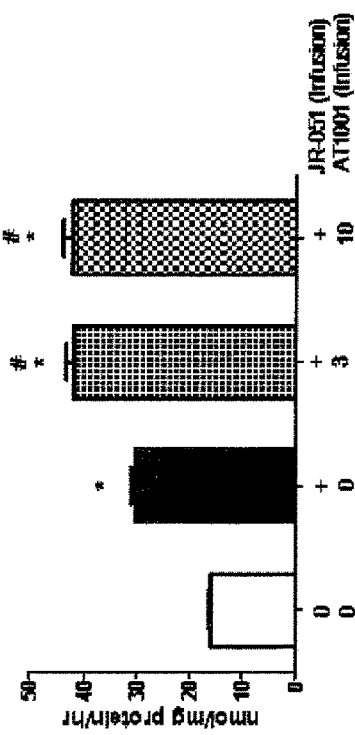
Figure 3B:
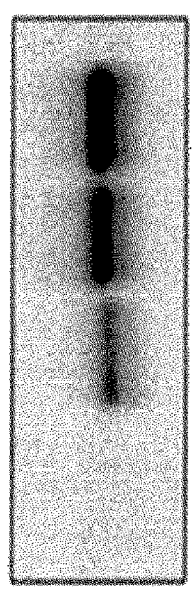

FIG. 3A-B shows tissue uptake of α-Gal A (JR-051) in (A) kidney and (B) heart tissue in WT mice following IV infusion administration of α-Gal A or a co-formulation of α-Gal A and DGJ-HCl, as described in Example 1.

Figure 4:
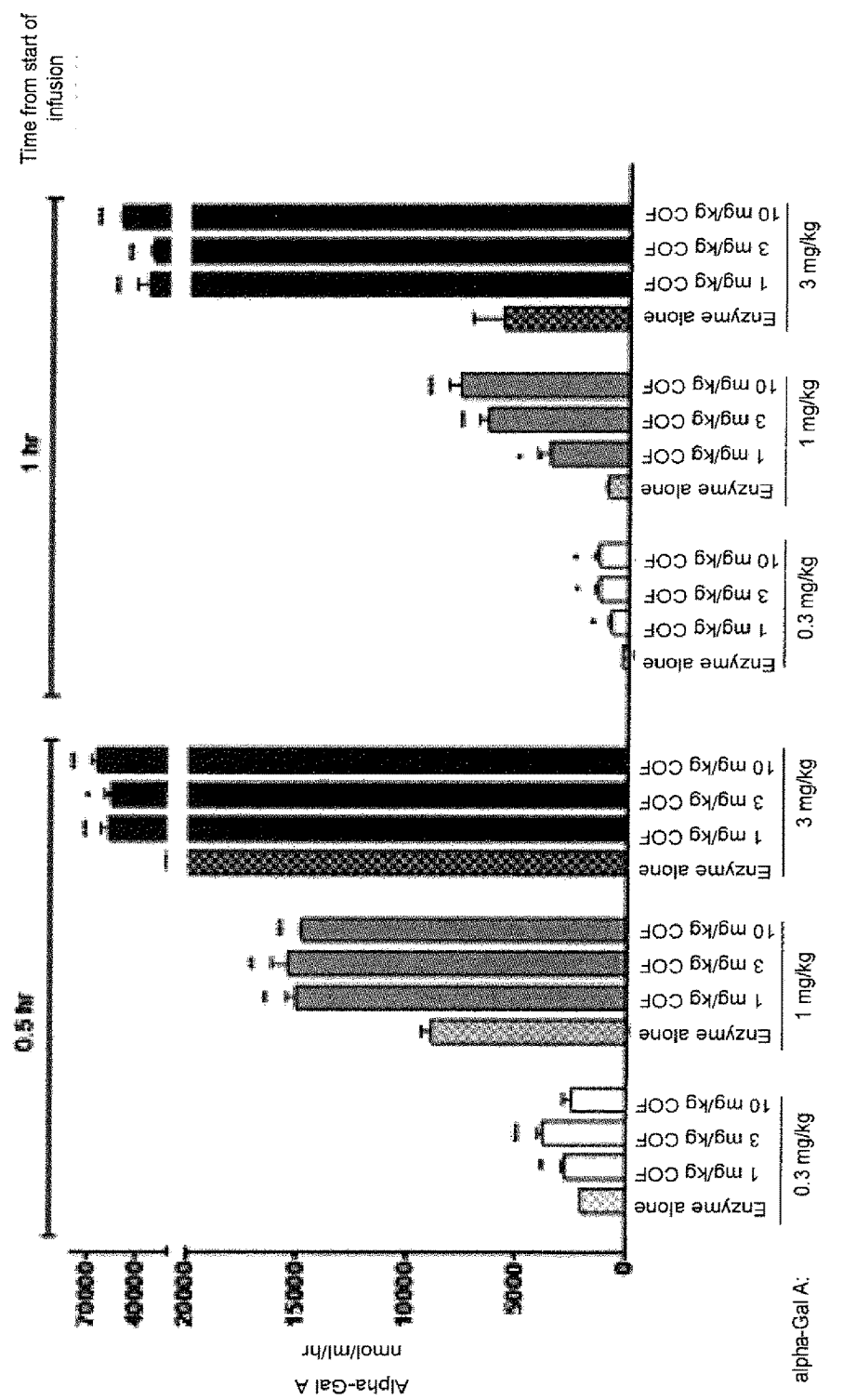

FIG. 4 shows plasma PK of α-Gal A (JR-051) in GLA KO mice following IV infusion administration of α-Gal A or a co-formulation of α-Gal A and DGJ-HCl, as described in Example 2. The co-formulated composition is referred to as "COF" in the graph.

Figure 5C:
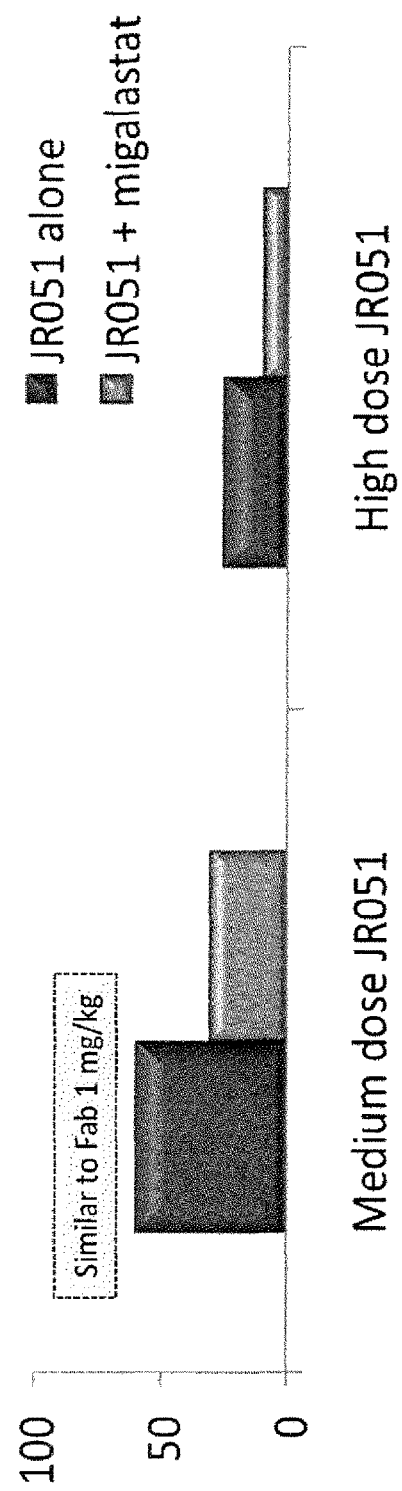

FIG. 5A-C shows GL-3 reduction (A) and (C) and tissue uptake (B) of α-Gal A (JR-051) in heart tissue of GLA KO mice following IV infusion administration of α-Gal A or a co-formulation of α-Gal A and DGJ-HCl, as described in Example 2.

Figure 6:
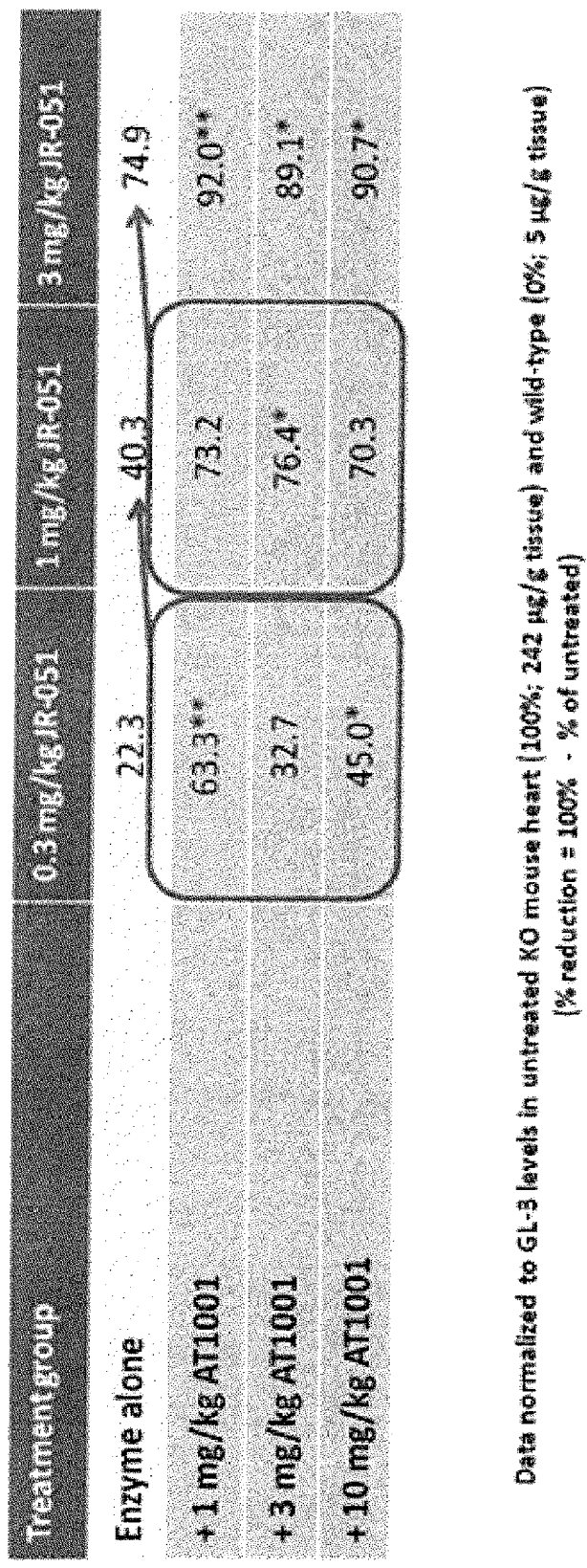

FIG. 6 shows GL-3 reduction (% reduction) in heart tissue of GLA KO mice following IV infusion administration of α-Gal A or a co-formulation of α-Gal A and DGJ-HCl, as described in Example 2.

Figure 7C:
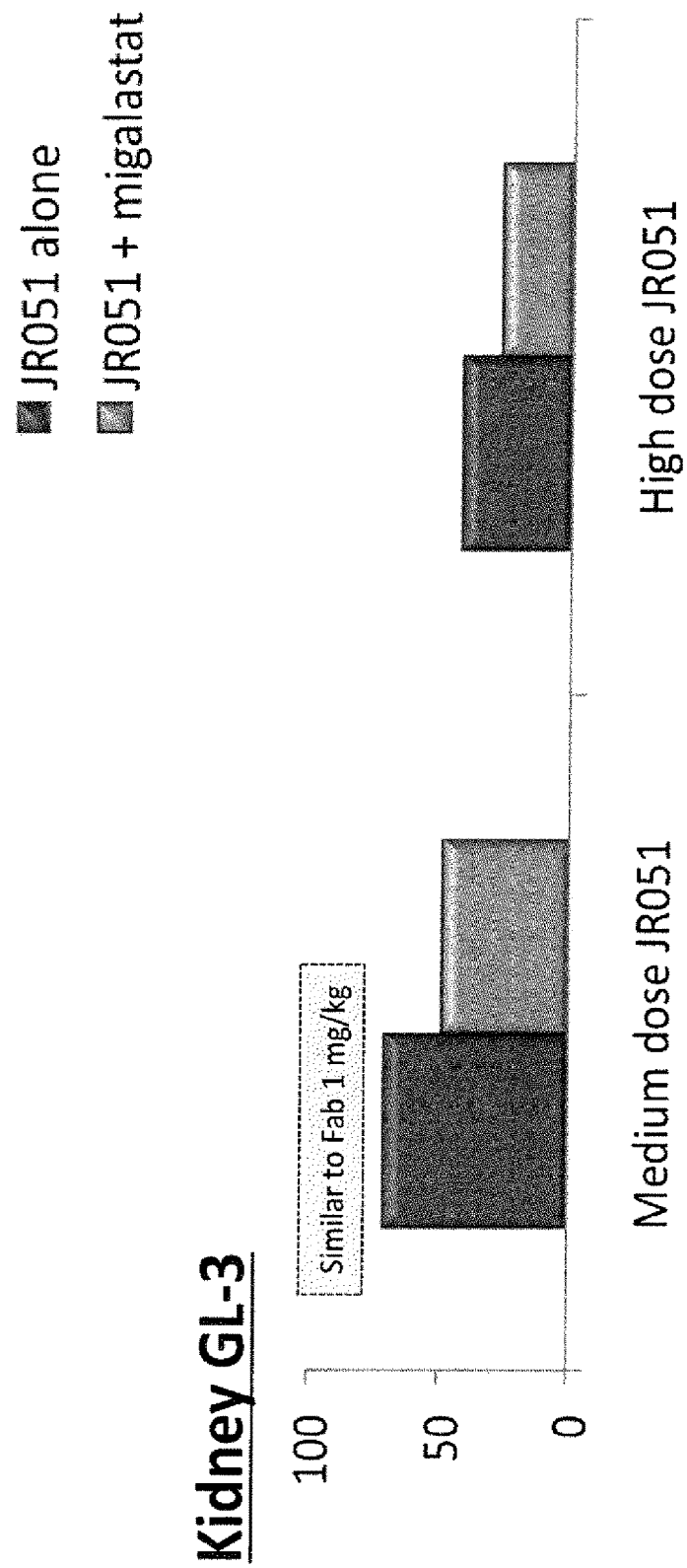

FIG. 7A-C shows GL-3 reduction (A) and (C) and tissue uptake (B) of α-Gal A (JR-051) in kidney tissue and of GLA KO mice following IV infusion administration of α-Gal A or a co-formulation of α-Gal A and DGJ-HCl, as described in Example 2.

FIG. 8 shows GL-3 reduction (% reduction) in kidney tissue of GLA KO mice following IV infusion administration of α-Gal A or a co-formulation of α-Gal A and DGJ-HCl, as described in Example 2.

Figures 9A, 9B:
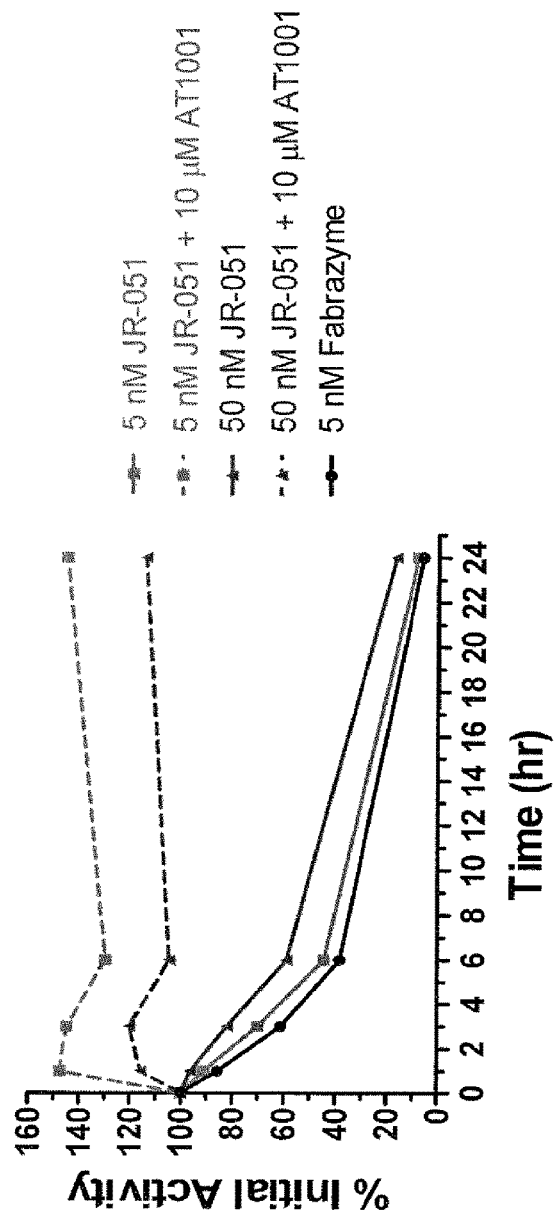

FIG. 9A-B shows the stability of α-Gal A formulated with or without DGJ in human whole blood ex vivo. Co-formulating α-Gal A (JR-051) with DGJ-HCL increases the stability of the enzyme in blood, and prevents loss of enzyme activity.

FIG. 10A-H shows α-Gal A uptake (A-D) and GL-3 reduction (E-H) in Fabry patient derived fibroblast cells. The fibroblast cells expressed the R301Q (A, C, E and G) or C52S (B, D, F and H) mutations. Cells were cultured with α-Gal A (JR-051 or Fabrazyme) formulated alone or with 0.1 µM, 1.0 µM, 10 µM or 100 µM DGJ.

FIG. 11A-C shows GL-3% reduction in skin, heart and kidney following administration of α-Gal A alone or as a co-formulation with DGJ to GLA KO mice, as described in Example 3. Data normalized to GL-3 levels in untreated KO and WT mouse tissues; % reduction=100%−% of untreated.

Figure 12:
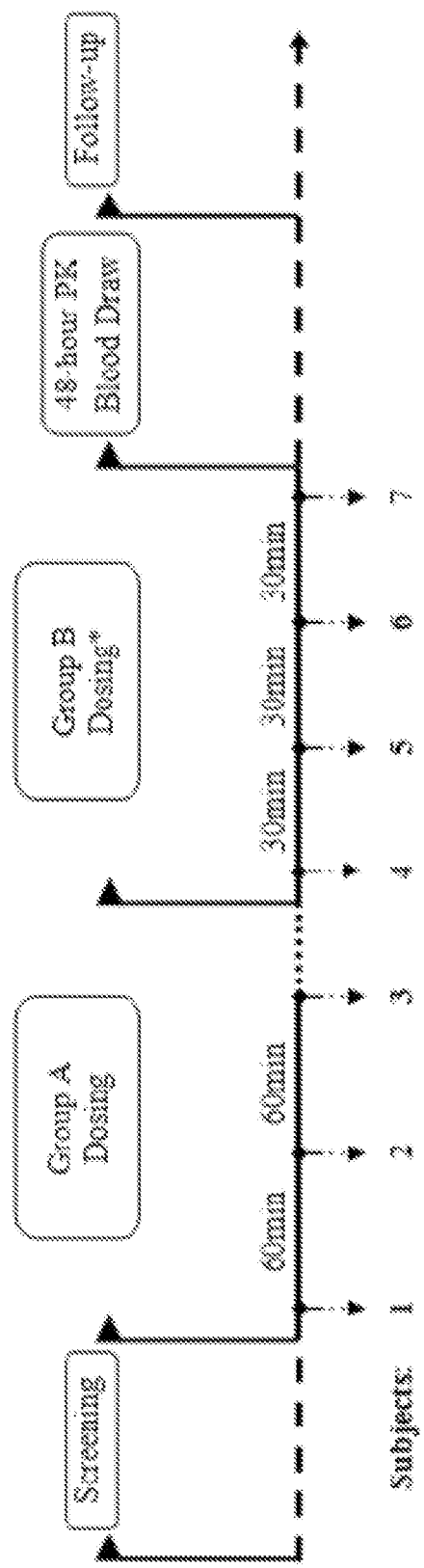

FIG. 12 shows a single dose cohort design for a study of migalastat intravenous dosing in human subjects.

Figure 13:
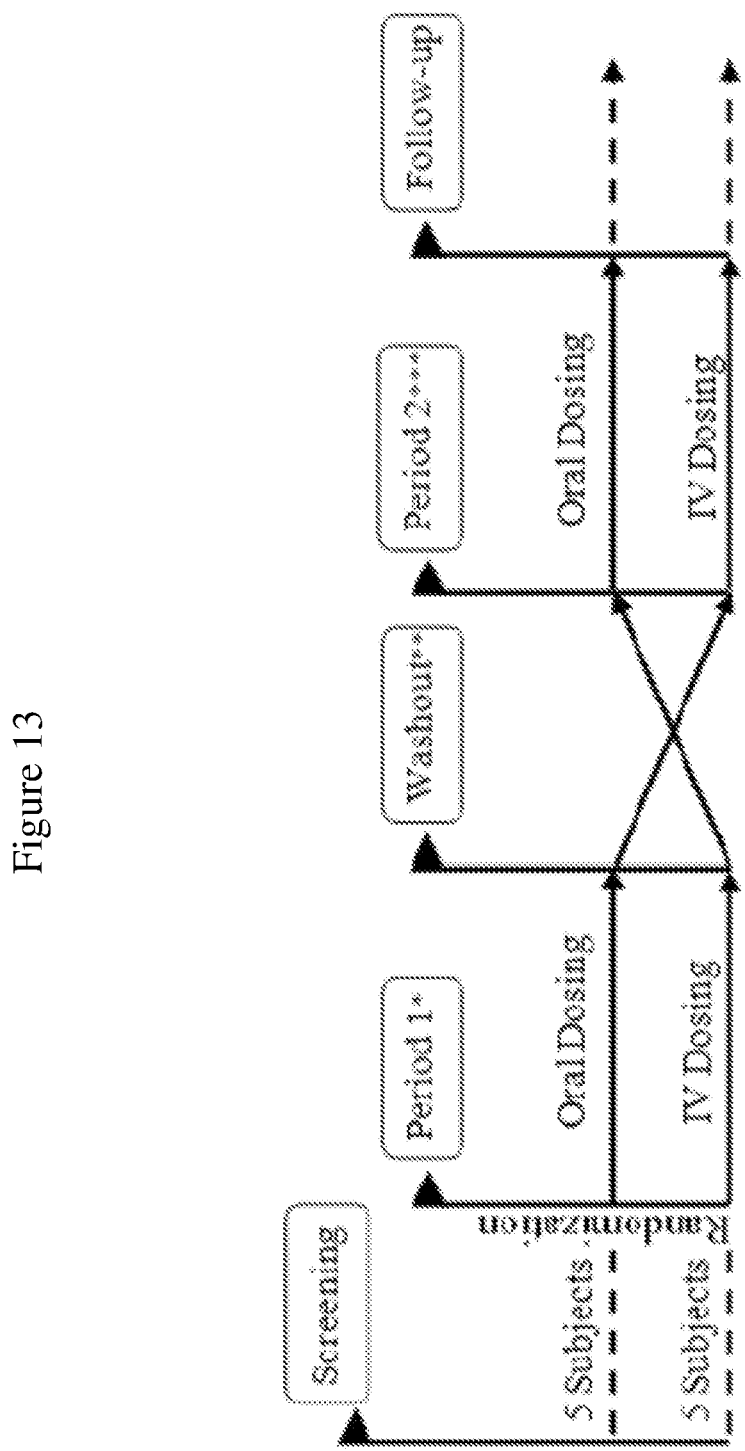

FIG. 13 shows cohort crossover design for a study of migalastat intravenous and oral administration in human subjects.

Figure 14A:
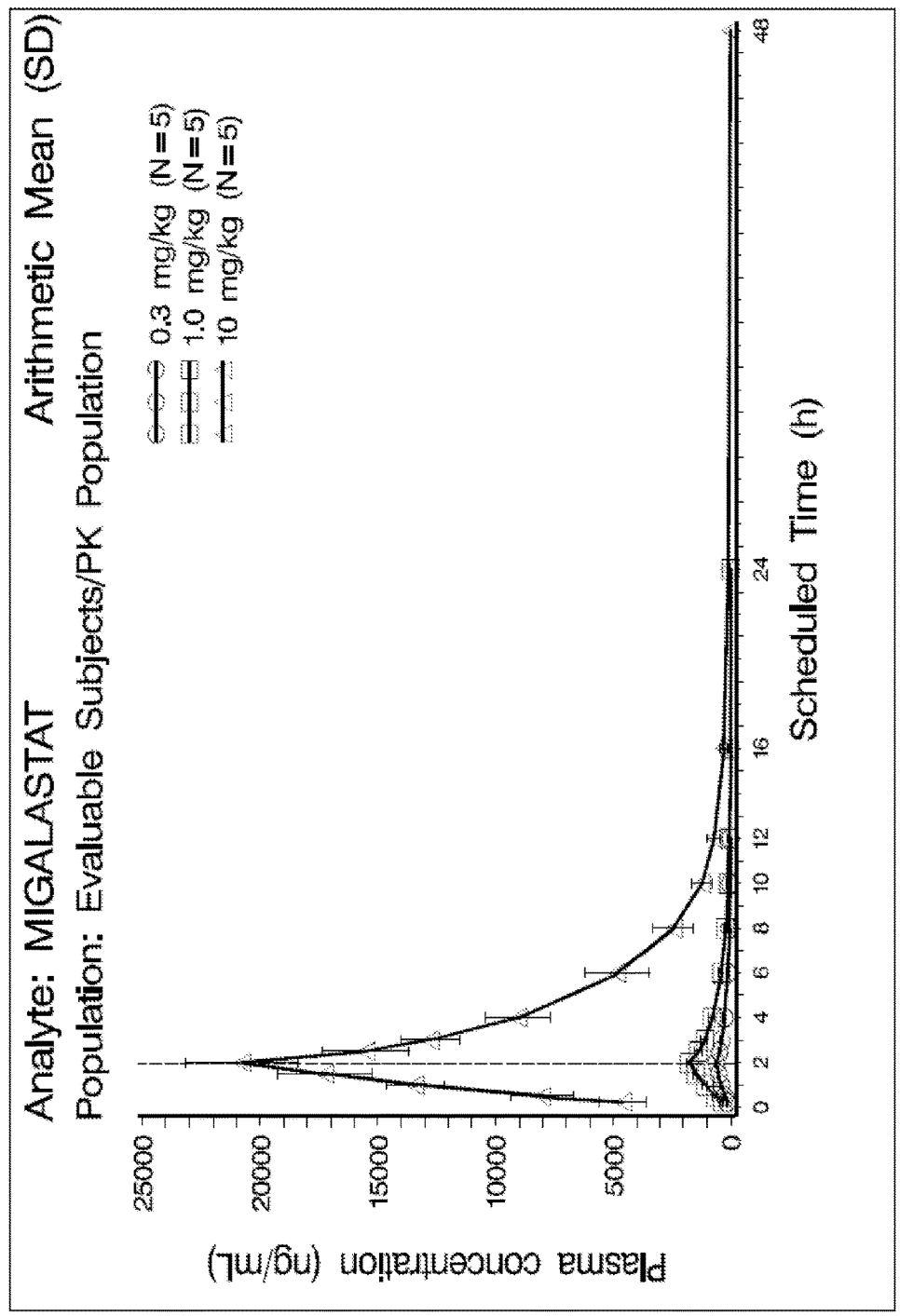
Figure 14B:
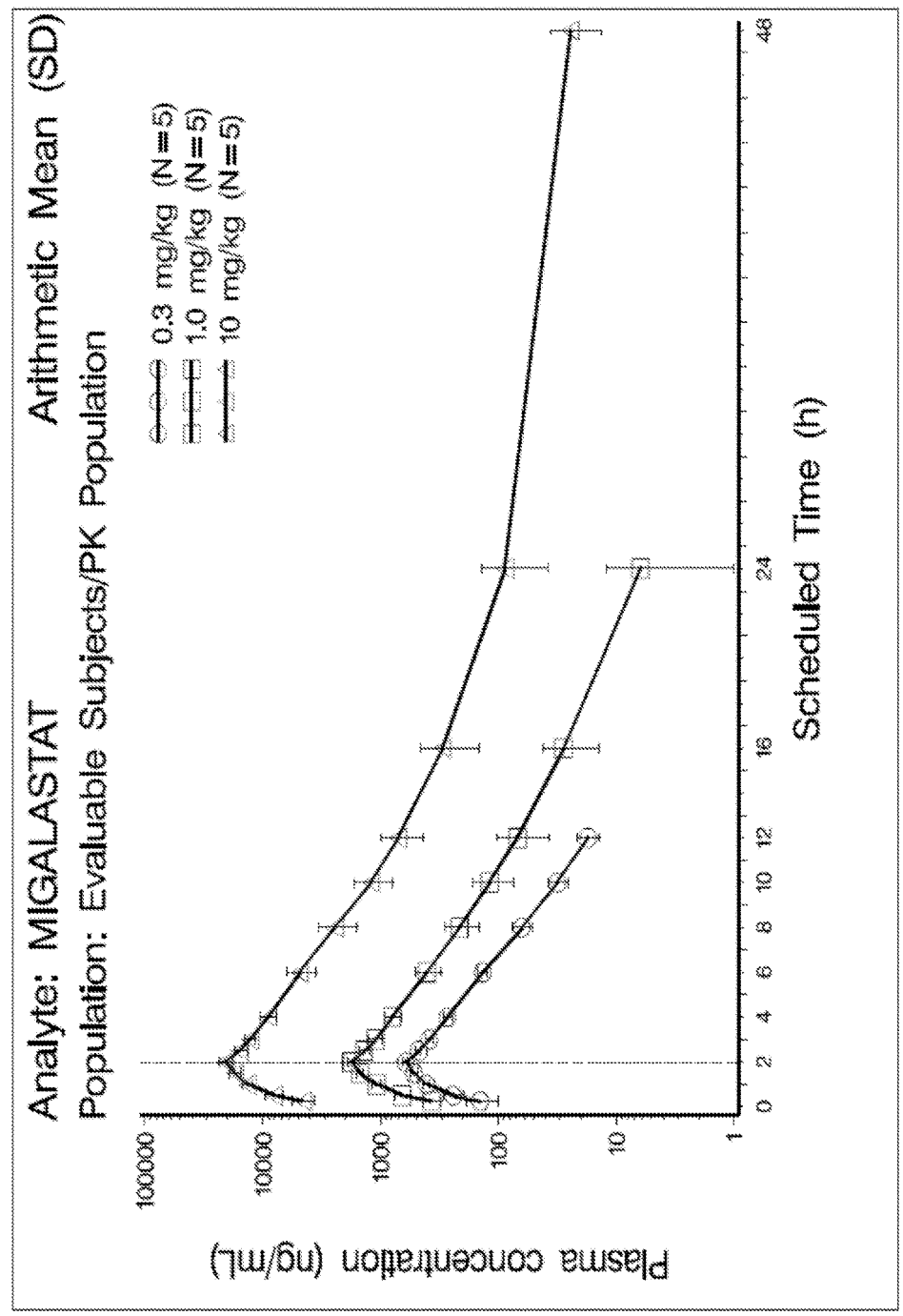

FIG. 14A-B shows the pharmacokinetic profile of migalastat intravenous dosing in human subjects.

Figure 15A:
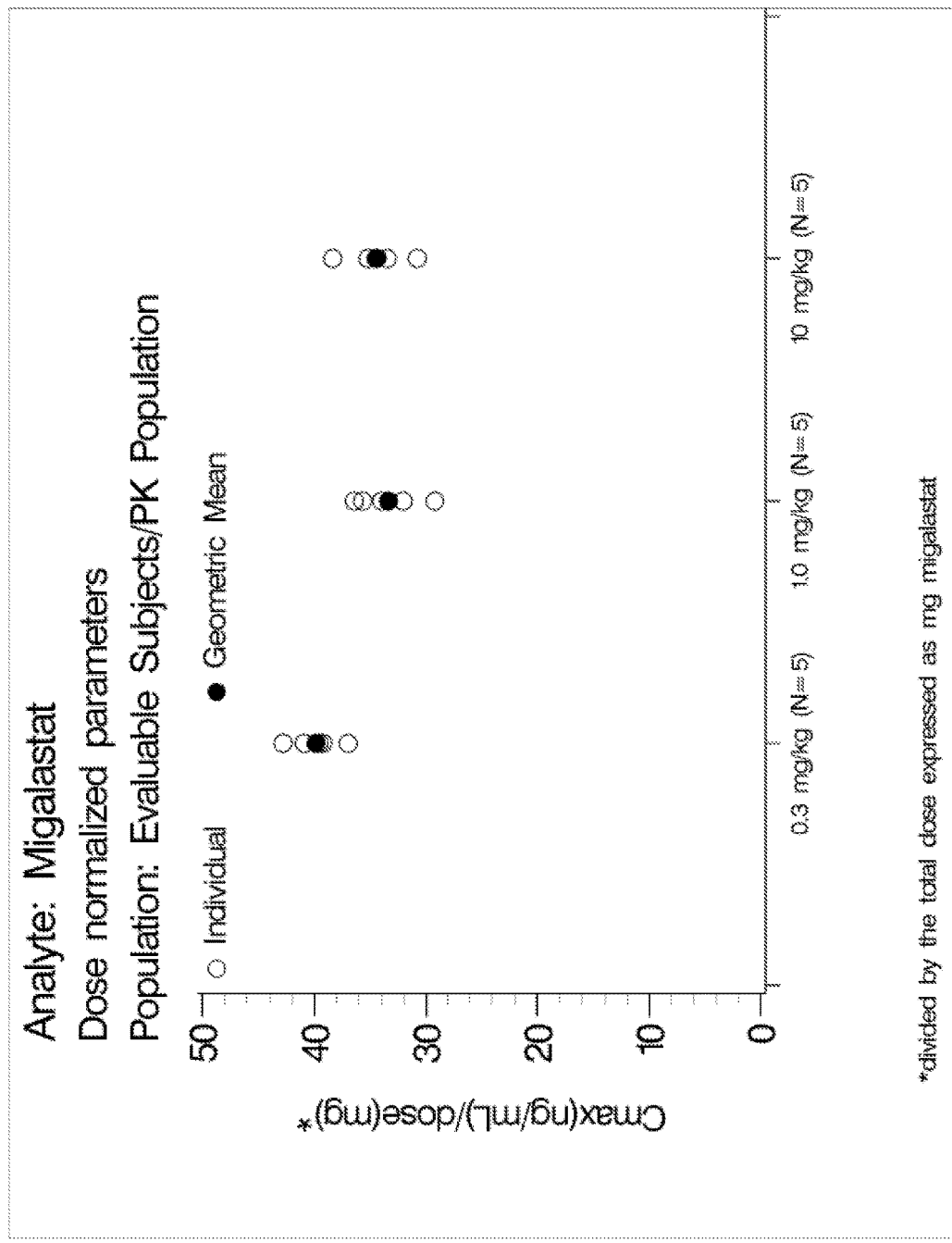
Figure 15B:
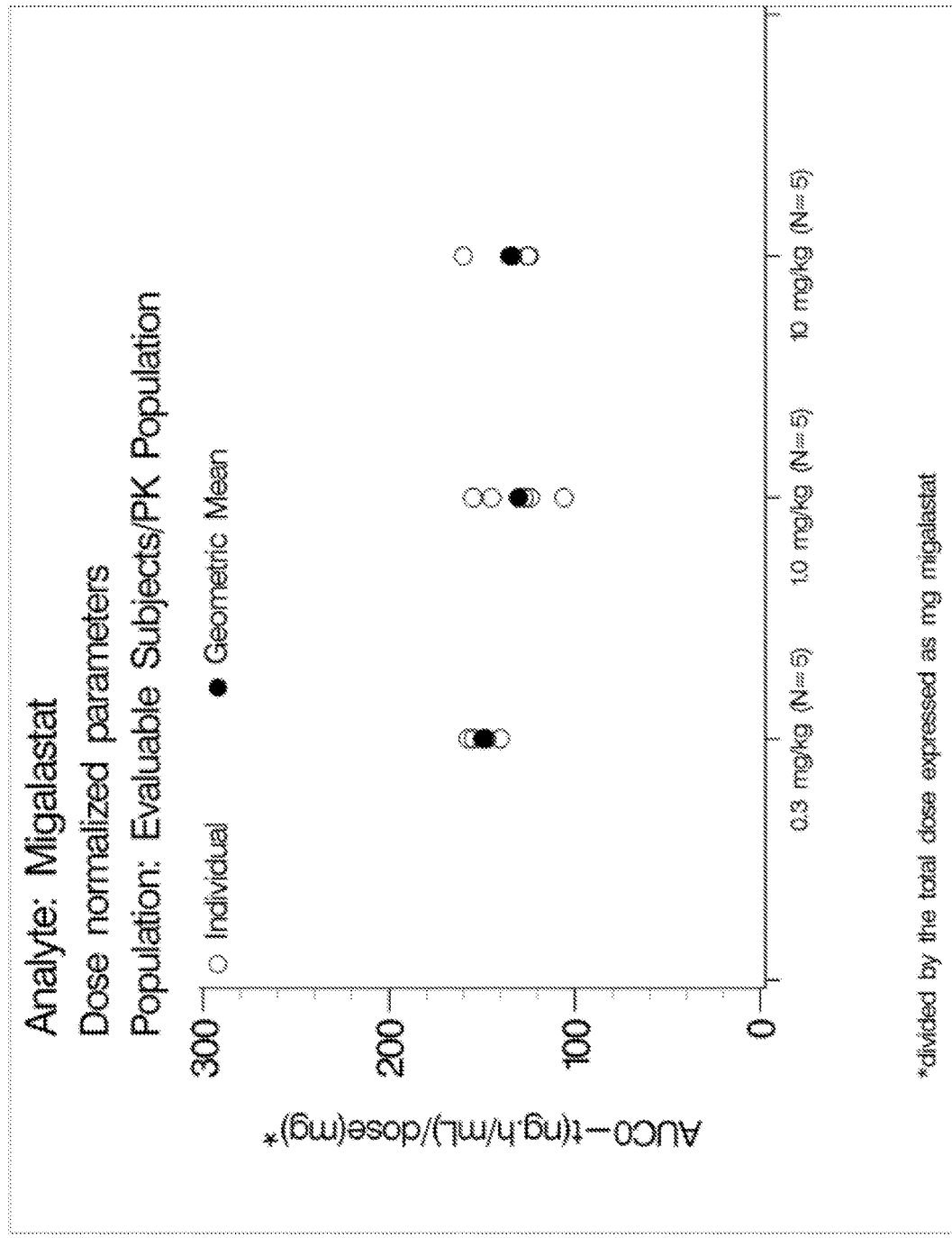
Figure 15C:
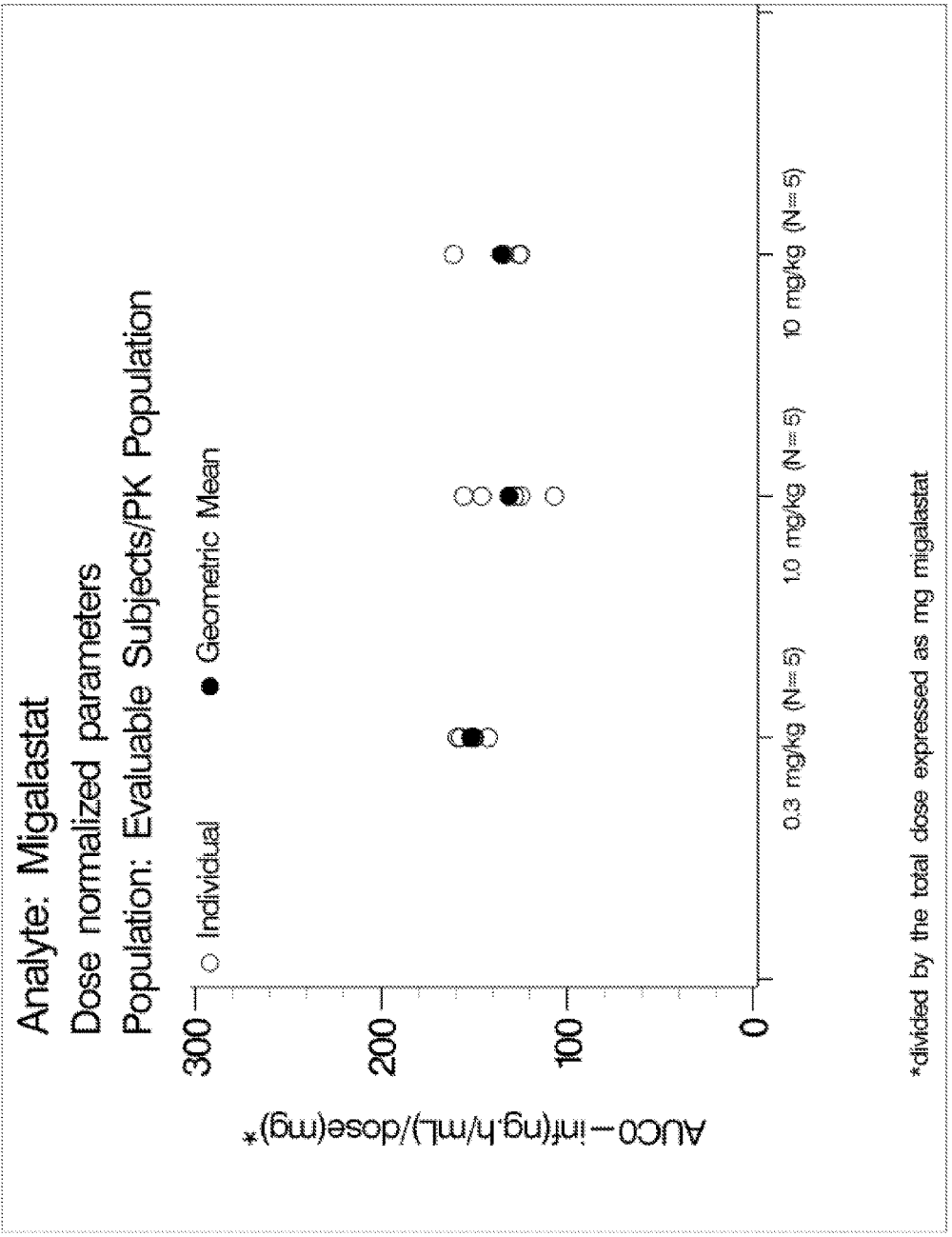

FIG. 15A-C shows the dose normalized parameters of migalastat intravenous dosing in human subjects.

Figure 16A:
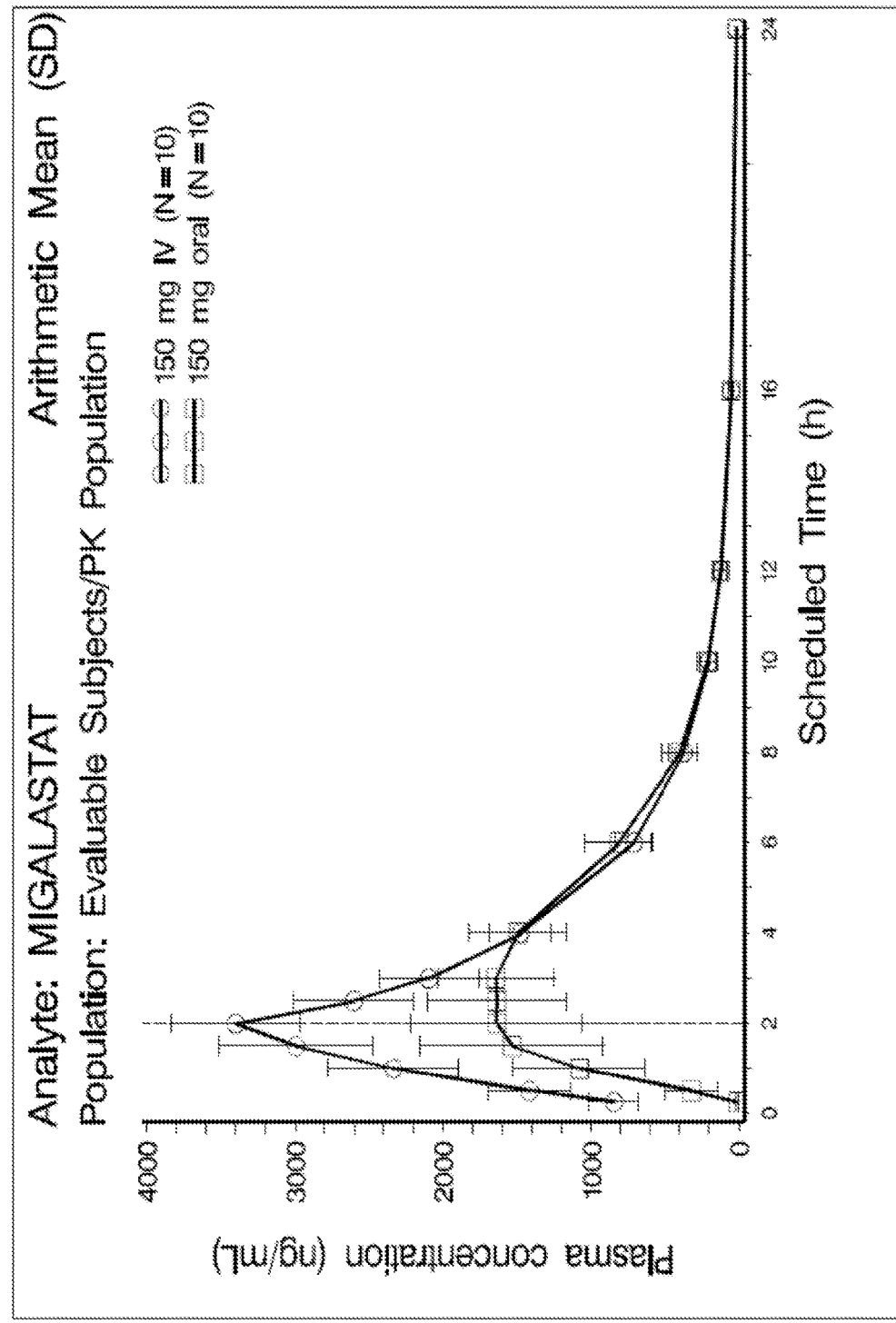
Figure 16B:
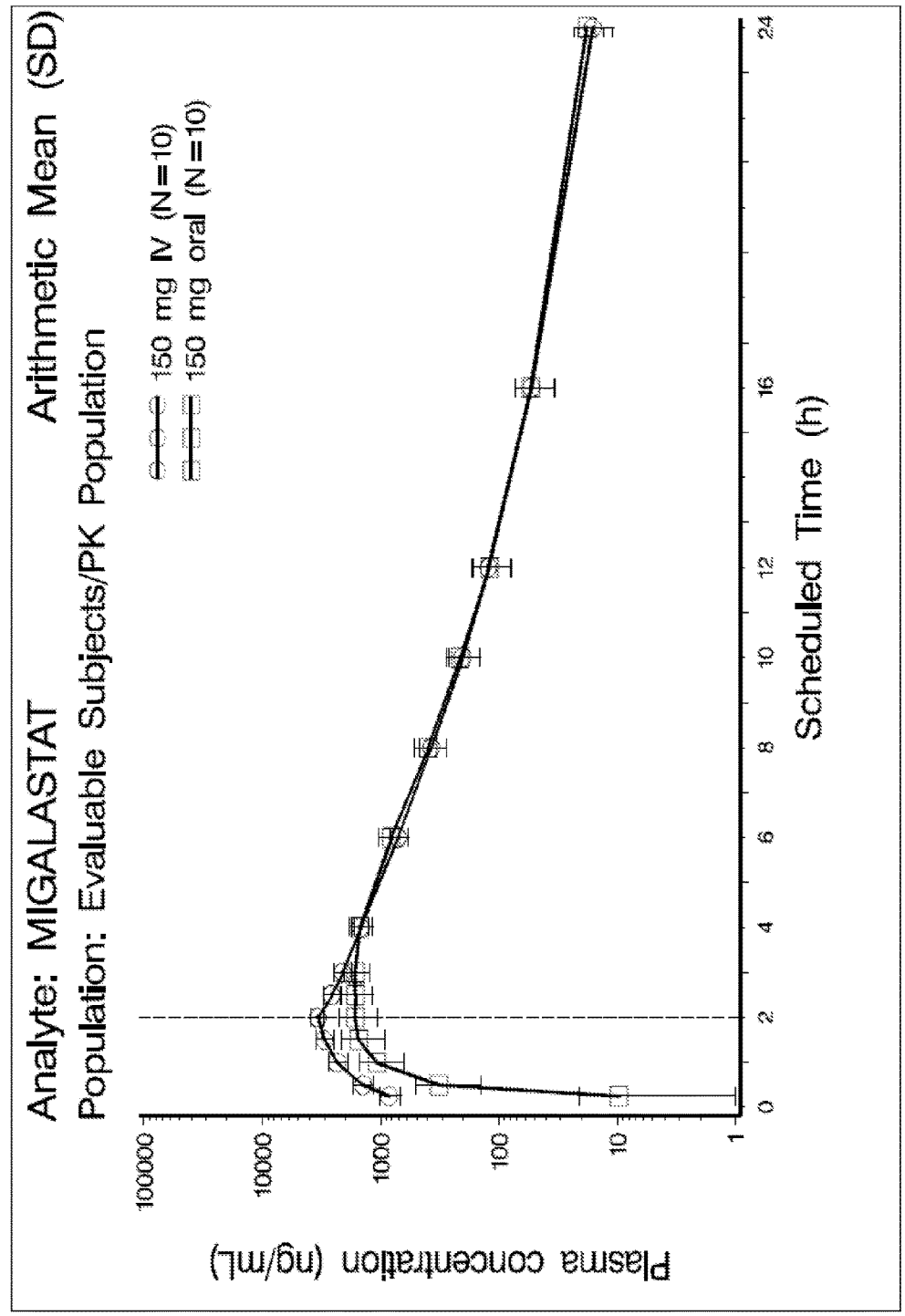

FIG. 16A-B shows a comparison of the pharmacokinetic profiles of intravenous and oral administration of migalastat.

Figure 17:
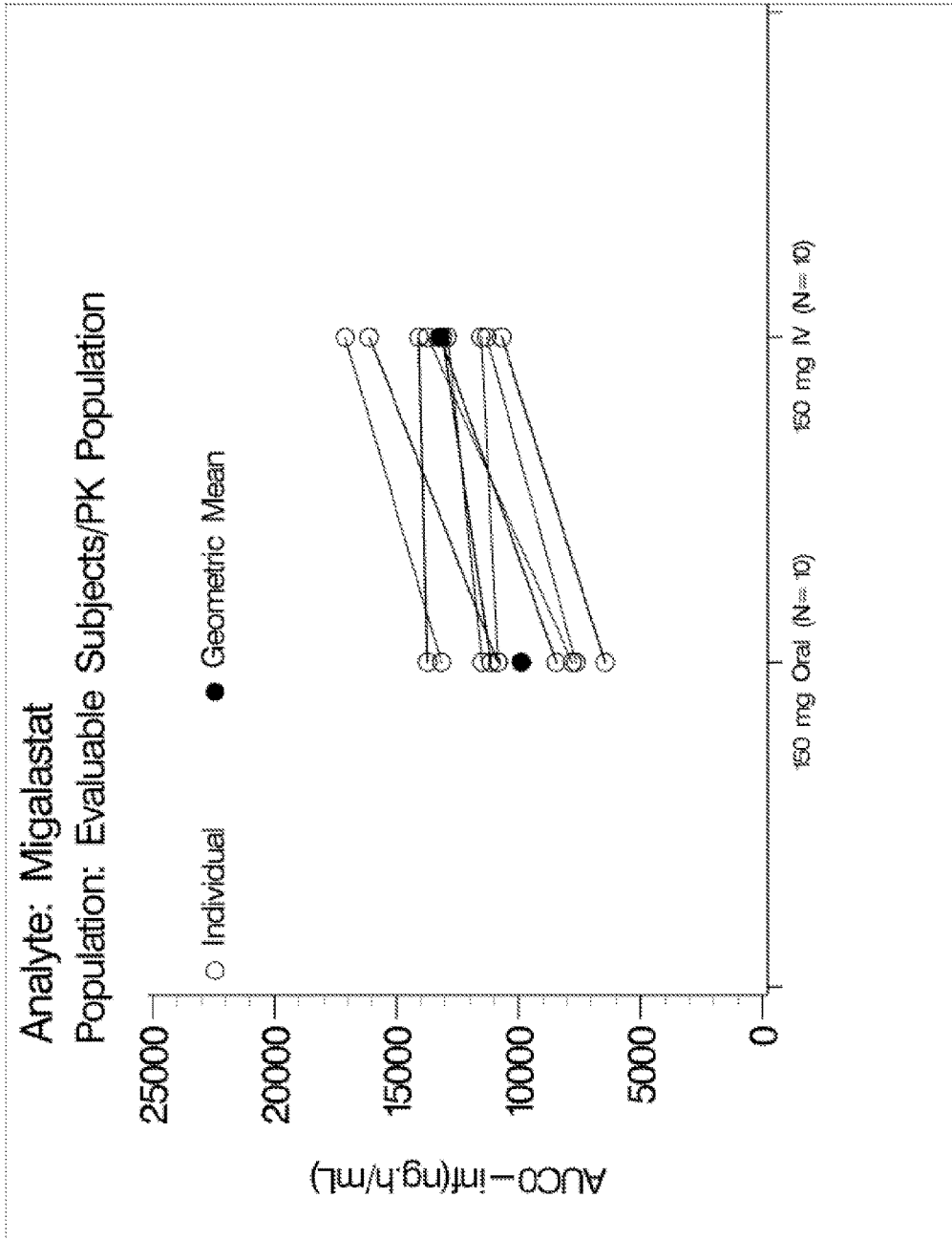

FIG. 17 shows a comparison of the migalastat exposure of intravenous and oral administration of migalastat.

5. DETAILED DESCRIPTION

For clarity and not by way of limitation, this detailed description is divided into the following sub-portions:
(i) Definitions;
(ii) Enzyme Replacement Therapy;
(iii) Pharmaceutical Compositions;
(iv) Treatment of Fabry Disease with ERT and an ASSC;
(v) In Vitro Stability; and
(vi) In Vivo Stability.

5.1 Definitions

The terms used in this specification generally have their ordinary meanings in the art, within the context of this application and in the specific context where each term is used. Certain terms are discussed below, or elsewhere in the specification, to provide additional guidance to the practitioner in describing the compositions and methods of the application and how to make and use them.

The terms "Fabry disease" refers to classical Fabry disease, late-onset Fabry disease, and hemizygous females having mutations in the gene encoding α-galactosidase A (α-Gal A). The term "Fabry disease," as used herein, further includes any condition in which a subject exhibits lower than normal endogenous α-Gal A activity.

"1-deoxygalactonojirimycin" (DGJ) refers to (2R,3S,4R,5S)-2-(hydroxymethyl) piperdine-3,4,5-triol. As used herein, reference to "1-deoxygalactonojirimycin" or "DGJ" or "AT1001" throughout includes both the free base and any pharmaceutically acceptable salt forms of the same. The hydrochloride salt of DGJ is known as migalastat hydrochloride.

The terms "α-galactosidase A" or "α-Gal A" refer to a protein with enzymatic activity comprising hydrolysis of terminal, non-reducing α-D-galactose residues in α-D-galactosides, including galactose oligosaccharides, galactomannans and galactolipids. In certain embodiments, α-Gal A comprises the enzyme described by IUBMB Enzyme Nomenclature EC 3.2.1.22 (see. e.g., http://www-.chem.qmul.ac.uk/iubmb/enzyme/EC3/2/1/22.html; Suzuki et al., α-Galactosidase from *Mortierella vinacea*. Crystallization and properties. J. Biol. Chem. 245 (1970) 781-786; and Wiederschain, G. and Beyer, E. [Interrelation of α-D-fucosidase and α-D-galactosidase activities in man and animals]. Dokl. Akad. Nauk S.S.S.R. 231 (1976) 486-488.). In certain embodiments, α-Gal A comprises a protein encoded by a nucleic acid comprising the human GLA gene, for example, the human GLA gene defined by GenBank Accession No. NM_000169. In certain embodiments, α-Gal A comprises a protein comprising the amino acid sequence defined by GenBank Accession No. NP_000160.

In certain embodiments, α-Gal A may be obtained from a cell endogenously expressing the α-Gal A, or the α-Gal A may be a recombinant human α-Gal A (rhα-Gal A), as described herein. In one, non-limiting embodiment, the rhα-Gal A is a full length wild-type α-Gal A. In other non-limiting embodiments, the rhα-Gal A comprises a subset of the amino acid residues present in a wild-type α-Gal A, wherein the subset includes the amino acid residues of the wild-type α-Gal A that form the active site for substrate binding and/or substrate reduction. As such, the present invention contemplates an rhα-Gal A that is a fusion protein comprising the wild-type α-Gal A active site for substrate binding and/or substrate reduction, as well as other amino acid residues that may or may not be present in the wild type α-Gal A.

α-Gal A may be obtained from commercial sources or may be obtained by synthesis techniques known to a person of ordinary skill in the art. The wild-type enzyme can be purified from a recombinant cellular expression system (e.g., mammalian cells such as CHO cells, or insect cells-see generally U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; and U.S. Pat. No. 6,083,725 to Selden et al.), human placenta, or animal milk.

Other synthesis techniques for obtaining α-Gal A suitable for pharmaceutical use can be found, for example, in U.S. Pat. No. 7,560,424 and U.S. Pat. No. 7,396,811 to Lebowitz et al., U.S. Published Application Nos. 2009/0203575, 2009/0029467, 2008/0299640, 2008/0241118, 2006/0121018, and 2005/0244400 to Lebowitz et al., U.S. Pat. Nos. 7,423,135, 6,534,300, and 6,537,785; International Published Application No. 2005/077093 and U.S. Published Application Nos. 2007/0280925, and 2004/0029779. These references are hereby incorporated by reference in their entirety.

In certain embodiments, the α-Gal A is Agalsidase alpha, produced by genetic engineering technology in a human cell line. Agalsidase alpha is available as Replagal®, from Shire Plc. (Dublin, Ireland).

In certain embodiments, the α-Gal A is Agalsidase beta, produced by recombinant DNA technology in a Chinese hamster ovary (CHO) cell line. Agalsidase beta is available as Fabrazyme®, from Genzyme Corporation (Cambridge, Mass.).

In certain embodiments, the α-Gal A is a recombinant human α-Gal A produced in CHO sells transformed with an expression vector encoding the human α-Gal A gene (JCR Pharmaceuticals Co. Ltd, (Japan)), identified as JR-051.

In addition to proteins that comprise an amino acid sequence that is identical to the human α-Gal A proteins described herein, this disclosure also encompasses α-Gal A proteins that are "substantially similar" thereto. Proteins described herein as being "substantially similar" to a reference protein include proteins that retain certain structural and functional features of the native proteins yet differ from the native amino acid sequence at one or more amino acid positions (i.e., by amino acid substitutions).

Proteins altered from the native sequence can be prepared by substituting amino acid residues within a native protein and selecting proteins with the desired activity. For example, amino acid residues of an α-Gal A protein can be systematically substituted with other residues and the substituted proteins can then be tested in standard assays for evaluating the effects of such substitutions on the ability of the protein to hydrolyze a terminal, non-reducing α-D-galactose residues in α-D-galactosides, including galactose oligosaccharides, galactomannans and galactolipids; and/or on the ability to treat or prevent Fabry disease.

In some embodiments, to retain functional activity, conservative amino acid substitutions are made. As used herein, the language a "conservative amino acid substitution" is intended to include a substitution in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Other substitutions involve replacement of an amino acid residue with another residue having a small side chain, such as alanine or glycine. Amino acid substituted peptides can be prepared by standard techniques, such as, for example, automated chemical synthesis.

In one embodiment, an α-Gal A protein of the present disclosure is at least about 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, homologous to the amino acid sequence of an α-Gal A protein described herein or known in the art.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences.

For example, the percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases, for example, to identify related sequences. Such searches can be performed, for example, using the XBLAST program (version 2.0) of Altschul, et al. (1990) *J. Mol. Biol.* 215:403-10. To obtain gapped alignments for comparison purposes, Gapped BLAST can be utilized, for example, as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See the National Center for Biotechnology Information (NCBI) website.

The term "AUC" represents a mathematical calculation to evaluate the body's total exposure over time to a given drug. In a graph plotting how concentration in the blood after dosing, the drug concentration variable lies on the y-axis and time lies on the x-axis. The area between a drug concentration curve and the x-axis for a designated time interval is the AUC. AUCs are used as a guide for dosing schedules and to compare different drugs' availability in the body.

The term "Cmax" represents the maximum plasma concentration achieved after dosing.

According to the application, a "subject" or "patient" is a human or non-human animal. In certain embodiments, the subject is a mammal. In certain embodiments, the subject is a human. Although the animal subject is preferably a human, the compounds and compositions of the application have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term "enzyme replacement therapy" or "ERT" refers to refers to the introduction of a non-native, purified enzyme into an individual having a deficiency in such enzyme. The administered enzyme can be obtained from natural sources or by recombinant expression. The term also refers to the introduction of a purified enzyme in an individual otherwise requiring or benefiting from administration of a purified enzyme, e.g., suffering from protein insufficiency. The introduced enzyme can be a purified, recombinant enzyme produced in vitro, or enzyme purified from isolated tissue or fluid, such as, e.g., placenta or animal milk, or from plants.

The term "adjuvant" or "adjuvant therapy" refers to any additional substance, treatment, or procedure used for increasing the efficacy, safety, or otherwise facilitating or enhancing the performance of a primary substance, treatment, or procedure.

The term "co-formulation" refers to a composition comprising an enzyme, such as an enzyme used for ERT, for example, an α-Gal A enzyme (e.g., a human recombinant α-Gal A enzyme (rhα-Gal A)), that is formulated together with an ASSC for the enzyme. In certain embodiments the ASSC is 1-deoxygalactonojirimycin (DGJ), or a pharmaceutically acceptable salt, ester or prodrug of 1-deoxygalactonojirimycin. In one embodiment, the salt is hydrochloride salt (i.e. 1-deoxygalactonojirimycin-HCl). In certain embodiments, treating a subject with the co-formulation comprises administering the co-formulation to the subject such that the α-Gal A enzyme and ASSC are administered concurrently at the same time as part of the co-formulation.

The term "combination therapy" refers to any therapy wherein the results are enhanced as compared to the effect of each therapy when it is performed individually. The individual therapies in a combination therapy can be administered concurrently or consecutively.

Enhancement can include any improvement of the effect of the various therapies that may result in an advantageous result as compared to the results achieved by the therapies when performed alone. Enhanced effect and determination of enhanced effect can be measured by various parameters such as, but not limited to: temporal parameters (e.g., length of treatment, recovery time, long-term effect of the treatment or reversibility of treatment); biological parameters (e.g., cell number, cell volume, cell composition, tissue volume, tissue size, tissue composition); spatial parameters (e.g., tissue strength, tissue size or tissue accessibility) and physiological parameters (e.g., body contouring, pain, discomfort, recovery time or visible marks). Enhanced effect can include a synergistic enhancement, wherein the enhanced effect is more than the additive effects of each therapy when performed by itself. Enhanced effect can also include an additive enhancement, wherein the enhanced effect is substantially equal to the additive effect of each therapy when performed by itself. Enhanced effect can also include less than a synergistic effect, wherein the enhanced effect is lower than the additive effect of each therapy when performed by itself, but still better than the effect of each therapy when performed by itself.

The term "stabilize a proper conformation" refers to the ability of a compound or peptide or other molecule to associate with a wild-type protein, or to a mutant protein that can perform its wild-type function in vitro and in vivo, in such a way that the structure of the wild-type or mutant protein can be maintained as its native or proper form. This effect can manifest itself practically through one or more of (i) increased shelf-life of the protein; (ii) higher activity per unit/amount of protein; or (iii) greater in vivo efficacy. It may be observed experimentally through increased yield from the ER during expression; greater resistance to unfolding due to temperature increases (e.g., as determined in thermal stability assays), or the present of chaotropic agents, and by similar means.

As used herein, the term "active site" refers to the region of a protein that has some specific biological activity. For example, it can be a site that binds a substrate or other binding partner and contributes the amino acid residues that directly participate in the making and breaking of chemical bonds. Active sites in this application can encompass catalytic sites of enzymes, antigen biding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "active site-specific chaperone" refers to any molecule including a protein, peptide, nucleic acid, carbohydrate, etc. that specifically interacts reversibly with an active site of a protein and enhances formation of a stable molecular conformation. As used herein, "active site-specific chaperone" does not include endogenous general chaperones present in the ER of cells such as Bip, calnexin or calreticulin, or general, non-specific chemical chaperones such as deuterated water, DMSO, or TMAO.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for safe administration to a human or non-human animal.

As used herein, the terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

As used herein the term "mutant protein" refers to proteins translated from genes containing genetic mutations that result in altered protein sequences. In a specific embodiment, such mutations result in the inability of the protein to achieve its native conformation under the conditions normally present in the ER. The failure to achieve this conformation results in these proteins being degraded, rather than being transported through their normal pathway in the protein transport system to their proper location within the cell. Other mutations can result in decreased activity or more rapid turnover.

As used herein the term "wild-type gene" refers to a nucleic acid sequences which encodes a protein capable of having normal biological functional activity in vivo. The wild-type nucleic acid sequence may contain nucleotide changes that differ from the known, published sequence, as long as the changes result in amino acid substitutions having little or no effect on the biological activity. The term wild-type may also include nucleic acid sequences engineered to encode a protein capable of increased or enhanced activity relative to the endogenous or native protein.

As used herein, the term "wild-type protein" refers to any protein encoded by a wild-type gene that is capable of having functional biological activity when expressed or introduced in vivo. The term "normal wild-type activity" refers to the normal physiological function of a protein in a cell. Such functionality can be tested by any means known to establish functionality of a protein.

The term "genetically modified" refers to cells that express a particular gene product following introduction of a nucleic acid comprising a coding sequence which encodes the gene product, along with regulatory elements that control expression of the coding sequence. Introduction of the nucleic acid can be accomplished by any method known in the art including gene targeting and homologous recombination. As used herein, the term also includes cells that have been engineered to express or overexpress an endogenous gene or gene product not normally expressed by such cell, e.g., by gene activation technology.

The phrase "pharmaceutically acceptable", whether used in connection with the pharmaceutical compositions of the application, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "therapeutically effective dose" and "effective amount" refer to the amount of the compound that is sufficient to result in a therapeutic response. In embodiments where an ASSC and α-Gal A are administered together in a co-formulation, the terms "therapeutically effective dose" and "effective amount" may refer to the amount of the co-formulation that is sufficient to result in a therapeutic response. A therapeutic response can be any response that a user (e.g., a clinician) will recognize as an effective response to the therapy. Thus, a therapeutic response will generally be an amelioration of one or more symptoms or sign of a disease or disorder.

Non-limiting examples of improvements in surrogate markers for Fabry disease include increases in α-GAL levels or activity in cells (e.g., fibroblasts) and tissue; reductions in of GL-3 accumulation as measured by the change in kidney interstitial capillary biopsies using histology; decreased urine GL-3 levels; assessment of renal function (including glomerular filtration rate (GFR) and 24-hour urine protein; decreased plasma concentrations of homocysteine and vascular cell adhesion molecule-1 (VCAM-1); decreased GL-3 accumulation within myocardial cells and valvular fibrocytes; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin (Fuller et al., *Clinical Chemistry*. 2005; 51: 688-694); the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities).

It should be noted that a concentration of the ASSC that is inhibitory during in vitro production, transportation, or storage of the purified therapeutic protein can still constitute an "effective amount" for purposes of this application because of dilution (and consequent shift in binding due to the change in equilibrium), bioavailability and metabolism of the ASSC upon administration in vivo.

5.2 Enzyme Replacement Therapy

The current approved treatment for Fabry disease is enzyme replacement therapy. Two products are currently available for the treatment of Fabry disease: agalsidase alfa (Replagal®, Shire Human Genetic Therapies) and agalsidase beta (Fabrazyme®; Genzyme Corporation), marketed globally. These two forms of ERT are intended to compensate for a patient's inadequate α-Gal A activity with a recombinant form of the enzyme, administered intravenously. ERT has been demonstrated to reduce GL-3 deposition in capillary endothelium of the kidney and certain other cell types. While ERT is effective in many settings, the treatment also has limitations. ERT has not been demonstrated to decrease the risk of stroke, cardiac muscle responds slowly, and GL-3 elimination from some of the cell types of the kidneys is limited. Some patients develop immune reactions to ERT.

The recommended dosage of agalsidase alfa is 0.2 mg/kg body weight infused every 2 weeks as an intravenous infusion The recommended dosage of agalsidase beta is 1 mg/kg body weight infused every 2 weeks as an intravenous infusion.

5.3 Pharmaceutical Compositions

According to the present application, 1-deoxygalactonojirimycin (DGJ) can be administered as the free base or as a pharmacologically acceptable salt form, including 1-deoxygalactonojirimycin hydrochloride (also known as, migalastat hydrochloride). It can be administered in a form suitable for parenteral administration, including e.g., in a sterile aqueous solution for intravenous administration. The compounds and compositions of the application can be formulated as pharmaceutical compositions by admixture with a pharmaceutically acceptable carrier or excipient.

In certain embodiments, DGJ and α-Gal A are formulated together in a single composition (i.e., co-formulated together). Such a composition enhances stability of α-Gal A both during storage (i.e., in vitro) and in vivo after administration to a subject, thereby increasing circulating half-life, tissue uptake, and resulting in increased therapeutic efficacy of α-Gal A (e.g., increasing the reduction of tissue GL-3 levels). The co-formulation is preferably suitable for intravenous administration.

The present application features liquid pharmaceutical co-formulations (e.g., formulations comprising α-Gal A and DGJ) having improved properties as compared to art-recognized formulations.

In certain embodiments, co-formulations of the application include an α-Gal A enzyme and DGJ that are suitable for intravenous administration.

In certain embodiments, the compositions of the present application comprise a co-formulation of an α-Gal A enzyme and an ASSC for the α-Gal A enzyme. In certain embodiments, the ASSC is 1-deoxygalactonojirimycin. In certain embodiments, the ASSC is 1-deoxygalactonojirimycin-HCl.

In certain embodiments, the co-formulation composition comprises α-Gal A at a concentration of between about 0.05 and about 100 μM, or between about 0.1 and about 75 μM, or between about 0.2 and about 50 μM, or between about 0.3 and about 40 μM, or between about 0.4 and about 30 μM, or between about 0.5 and about 20 μM, or between about 0.6 and about 15 μM, or between about 0.7 and about 10 μM, or between about 0.8 and about 9 μM, or between about 0.9 and about 8 μM, or between about 1 and about 7 μM, or between about 2 and about 6 μM, or between about 3 and about 5 μM. Concentrations and ranges intermediate to the above recited concentrations are also intended to be part of this application.

In certain embodiments, the co-formulation composition comprises α-Gal A at a concentration of about 0.1, 0.2, 0.3, 0.4, 0.5, 0.6, 0.7, 0.8, 0.9, 1, 1.1, 1.2, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 μM.

In certain embodiments, the co-formulation composition comprises α-Gal A at a concentration of between about 0.0025 and about 5 mg/ml, or between about 0.005 and about 4.5 mg/ml, or between about 0.025 and about 4 mg/ml, or between about 0.05 and about 3.5 mg/ml, or between about 0.25 and about 3 mg/ml, or between about 0.5 and about 2.5 mg/ml, or between about 0.75 and about 2 mg/ml, or between about 1 and about 1.5 mg/ml. Concentrations and ranges intermediate to the above recited concentrations are also intended to be part of this application.

In certain embodiments, the co-formulation composition comprises DGJ at a concentration of between about 10 and about 25,000 μM, or between about 50 and about 20,000 μM, or between about 100 and about 15,000 μM, or between about 150 and about 10,000 μM, or between about 200 and about 5,000 μM, or between about 250 and about 1,500 μM, or between about 300 and about 1,000 μM, or between about 350 and about 550 μM, or between about 400 and about 500 μM. Concentrations and ranges intermediate to the above recited concentrations are also intended to be part of this application.

In certain embodiments, the co-formulation composition comprises DGJ at a concentration of between about 0.002 and about 5 mg/ml, or between about 0.005 and about 4.5 mg/ml, or between about 0.02 and about 4 mg/ml, or between about 0.05 and about 3.5 mg/ml, or between about 0.2 and about 3 mg/ml, or between about 0.5, and about 2.5 mg/ml, or between about 1 and about 2 mg/ml. Concentrations and ranges intermediate to the above recited concentrations are also intended to be part of this application.

In certain embodiments, the co-formulation composition comprises DGJ at a concentration of about 50; 100; 150; 200; 250; 300; 350; 400; 450; 500; 550; 600; 650; 700; 750; 800; 850; 900; 950; 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000 or 20,000 μM.

In certain embodiments, the co-formulation composition comprises DGJ at a concentration of about 449, 748, 1,495, 4,490, or 14,950 μM.

In certain embodiments, the co-formulation composition of the application comprises α-Gal A enzyme and DGJ, wherein the α-Gal A is present at a concentration selected from the group consisting of 1.2, 2, 4, 8 and 12 μM; and wherein the DGJ is present at a concentration selected from the group consisting of 449, 748, 1,495, 4,490 and 14,950 μM.

In certain embodiments, the co-formulation composition of the application comprises about 1.2 μM α-Gal A enzyme and about 449 μM DGJ.

In certain embodiments, the co-formulation composition of the application comprises about 1.2 μM α-Gal A enzyme and about 748 μM DGJ.

In certain embodiments, the co-formulation composition of the application comprises about 1.2 μM α-Gal A enzyme and about 1,495 μM DGJ.

In certain embodiments, the co-formulation composition of the application comprises about 1.2 μM α-Gal A enzyme and about 4,490 μM DGJ.

In certain embodiments, the co-formulation composition of the application comprises about 1.2 μM α-Gal A enzyme and about 14,950 μM DGJ.

In certain embodiments, the co-formulation composition of the application comprises about 2 μM α-Gal A enzyme and about 449 μM DGJ.

In certain embodiments, the co-formulation composition of the application comprises about 2 μM α-Gal A enzyme and about 748 μM DGJ.

In certain embodiments, the co-formulation composition of the application comprises about 2 μM α-Gal A enzyme and about 1,495 μM DGJ.

In certain embodiments, the co-formulation composition of the application comprises about 2 μM α-Gal A enzyme and about 4,490 μM DGJ.

In certain embodiments, the co-formulation composition of the application comprises about 2 μM α-Gal A enzyme and about 14,950 μM DGJ.

In certain embodiments, the co-formulation composition of the application comprises about 4 μM α-Gal A enzyme and about 449 μM DGJ.

In certain embodiments, the co-formulation composition of the application comprises about 4 μM α-Gal A enzyme and about 748 μM DGJ.

In certain embodiments, the co-formulation composition of the application comprises about 4 μM α-Gal A enzyme and about 1,495 μM DGJ.

In certain embodiments, the co-formulation composition of the application comprises about 4 μM α-Gal A enzyme and about 4,490 μM DGJ.

In certain embodiments, the co-formulation composition of the application comprises about 4 µM α-Gal A enzyme and about 14,950 µM DGJ.

In certain embodiments, the co-formulation composition of the application comprises about 8 µM α-Gal A enzyme and about 449 µM DGJ.

In certain embodiments, the co-formulation composition of the application comprises about 8 µM α-Gal A enzyme and about 748 µM DGJ.

In certain embodiments, the co-formulation composition of the application comprises about 8 µM α-Gal A enzyme and about 1,495 µM DGJ.

In certain embodiments, the co-formulation composition of the application comprises about 8 µM α-Gal A enzyme and about 4,490 µM DGJ.

In certain embodiments, the co-formulation composition of the application comprises about 8 µM α-Gal A enzyme and about 14,950 µM DGJ.

In certain embodiments, the co-formulation composition of the application comprises about 12 µM α-Gal A enzyme and about 449 µM DGJ.

In certain embodiments, the co-formulation composition of the application comprises about 12 µM α-Gal A enzyme and about 748 µM DGJ.

In certain embodiments, the co-formulation composition of the application comprises about 12 µM α-Gal A enzyme and about 1,495 µM DGJ.

In certain embodiments, the co-formulation composition of the application comprises about 12 µM α-Gal A enzyme and about 4,490 µM DGJ.

In certain embodiments, the co-formulation composition of the application comprises about 12 µM α-Gal A enzyme and about 14,950 µM DGJ.

The present invention also provides the use of a co-formulation of between about 0.5 and about 20 µM α-Gal A and between about 50 and 20,000 µM DGJ or a pharmaceutically acceptable salt thereof in the preparation of a medicament for the treatment of Fabry disease, wherein the medicament is formulated for parenteral administration to a subject.

The present invention also provides the use of a co-formulation of about 1.2, 2, 4, 8, or 12 µM α-Gal A and about 449, 748, 1,495, 4,490, or 14,950 µM DGJ or a pharmaceutically acceptable salt thereof in the preparation of a medicament for the treatment of Fabry disease, wherein the medicament is formulated for parenteral administration to a subject.

The present invention also provides the use of a co-formulation of between about 0.0025 and about 5 mg/ml, or between about 0.005 and about 4.5 mg/ml, or between about 0.025 and about 4 mg/ml, or between about 0.05 and about 3.5 mg/ml, or between about 0.25 and about 3 mg/ml, or between about 0.5 and about 2.5 mg/ml, or between about 0.75 and about 2 mg/ml, or between about 1 and about 1.5 mg/ml α-Gal A; and between about 0.002 and about 5 mg/ml, or between about 0.005 and about 4.5 mg/ml, or between about 0.02 and about 4 mg/ml, or between about 0.05 and about 3.5 mg/ml, or between about 0.2 and about 3 mg/ml, or between about 0.5, and about 2.5 mg/ml, or between about 1 and about 2 mg/ml DGJ or a pharmaceutically acceptable salt thereof in the preparation of a medicament for the treatment of Fabry disease, wherein the medicament is formulated for parenteral administration to a subject.

The present invention also provides the use of a co-formulation of between about 0.05 and about 100 µM, or between about 0.1 and about 75 µM, or between about 0.2 and about 50 µM, or between about 0.3 and about 40 µM, or between about 0.4 and about 30 µM, or between about 0.5 and about 20 µM, or between about 0.6 and about 15 µM, or between about 0.7 and about 10 µM, or between about 0.8 and about 9 µM, or between about 0.9 and about 8 µM, or between about 1 and about 7 µM, or between about 2 and about 6 µM, or between about 3 and about 5 µM α-Gal A; and between about 10 and about 25,000 µM, or between about 50 and about 20,000 µM, or between about 100 and about 15,000 µM, or between about 150 and about 10,000 µM, or between about 200 and about 5,000 µM, or between about 250 and about 1,500 µM, or between about 300 and about 1,000 µM, or between about 350 and about 550 µM, or between about 400 and about 500 µM DGJ or a pharmaceutically acceptable salt thereof in the preparation of a medicament for the treatment of Fabry disease, wherein the medicament is formulated for parenteral administration to a subject.

The present invention also provides the use of a co-formulation of about 0.1, 0.2, 0.3, 0.4, 0.5, 0.6, 0.7, 0.8, 0.9, 1, 1.1, 1.2, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 µM α-Gal A; and about 50; 100; 150; 200; 250; 300; 350; 400; 450; 500; 550; 600; 650; 700; 750; 800; 850; 900; 950; 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000 or 20,000 µM DGJ or a pharmaceutically acceptable salt thereof in the preparation of a medicament for the treatment of Fabry disease, wherein the medicament is formulated for parenteral administration to a subject.

The present invention also provides a co-formulation of between about 0.5 and about 20 µM α-Gal A and between about 50 and about 20,000 µM DGJ or a pharmaceutically acceptable salt thereof for use in the treatment of Fabry disease, wherein the co-formulation is administered parenterally.

The present invention also provides a co-formulation of about 1.2, 2, 4, 8, or 12 µM α-Gal A and about 449, 748, 1,495, 4,490, or 14,950 µM DGJ or a pharmaceutically acceptable salt thereof for use in the treatment of Fabry disease, wherein the co-formulation is administered parenterally.

The present invention also provides a co-formulation of between about 0.0025 and about 5 mg/ml, or between about 0.005 and about 4.5 mg/ml, or between about 0.025 and about 4 mg/ml, or between about 0.05 and about 3.5 mg/ml, or between about 0.25 and about 3 mg/ml, or between about 0.5 and about 2.5 mg/ml, or between about 0.75 and about 2 mg/ml, or between about 1 and about 1.5 mg/ml α-Gal A; and between about 0.002 and about 5 mg/ml, or between about 0.005 and about 4.5 mg/ml, or between about 0.02 and about 4 mg/ml, or between about 0.05 and about 3.5 mg/ml, or between about 0.2 and about 3 mg/ml, or between about 0.5, and about 2.5 mg/ml, or between about 1 and about 2 mg/ml DGJ or a pharmaceutically acceptable salt thereof for use in the treatment of Fabry disease, wherein the co-formulation is administered parenterally.

The present invention also provides a co-formulation of between about 0.05 and about 100 µM, or between about 0.1 and about 75 µM, or between about 0.2 and about 50 µM, or between about 0.3 and about 40 µM, or between about 0.4 and about 30 µM, or between about 0.5 and about 20 µM, or between about 0.6 and about 15 µM, or between about 0.7 and about 10 µM, or between about 0.8 and about 9 µM, or between about 0.9 and about 8 µM, or between about 1 and about 7 µM, or between about 2 and about 6 µM, or between about 3 and about 5 µM α-Gal A; and between about 10 and about 25,000 µM, or between about 50 and about 20,000 µM, or between about 100 and about 15,000 µM, or between about 150 and about 10,000 µM, or between about 200 and about 5,000 µM, or between about 250 and about 1,500 µM, or between about 300 and about 1,000 µM, or between about 350 and about 550 µM, or between about 400 and about 500 µM DGJ or a pharmaceutically acceptable salt thereof for use in the treatment of Fabry disease, wherein the co-formulation is administered parenterally.

The present invention also provides a co-formulation of about 0.1, 0.2, 0.3, 0.4, 0.5, 0.6, 0.7, 0.8, 0.9, 1, 1.1, 1.2, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 µM α-Gal A; and about 50; 100; 150; 200; 250; 300; 350; 400; 450; 500; 550; 600; 650; 700; 750; 800; 850; 900; 950; 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000 or 20,000 µM DGJ or a pharmaceutically acceptable salt thereof for use in the treatment of Fabry disease, wherein the co-formulation is administered parenterally.

In certain embodiments, the α-Gal A enzyme and DGJ are combined to create a co-formulation with a molar ratio of DGJ to α-Gal A enzyme of between about 10:1 and about 20,000:1; or between about 20:1 and about 15,000:1; or between about 50:1 and about 10,000:1; or between about 100:1 and about 5,000:1; or between about 150:1 and about 1,000:1; or between about 200:1 and about 500:1; or between about 250:1 and about 450:1; or between about 300:1 and about 400:1.

The pharmaceutical co-formulations suitable for intravenous administration use include sterile aqueous solutions (where water soluble) or dispersions and sterile powders for the extemporaneous preparation of sterile injectable solutions or dispersion. In certain embodiments, the form is sterile and fluid to the extent that easy syringability exists. In certain embodiments, it is stable under the conditions of manufacture and storage and preserved against the contaminating action of microorganisms such as bacteria and fungi. In certain embodiments, the composition comprises a carrier such as a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like.

In many cases, it will be preferable to include isotonic agents, for example, sugars or sodium chloride. Prolonged absorption of the injectable compositions can be brought about by the use in the compositions of agents delaying absorption, for example, aluminum monosterate and gelatin. Sterile injectable solutions can be prepared by incorporating the α-Gal A and ASSC (e.g., DGJ) in the required amounts in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

In certain embodiments, the co-formulation can contain an excipient. Pharmaceutically acceptable excipients which can be included in the co-formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the co-formulations include citrate; acetate; bicarbonate; and phosphate buffers.

The co-formulation also can contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

For lyophilization of protein and chaperone preparations, the protein concentration can be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

In certain embodiments, the co-formulation composition of the application is formulated for intravenous administration. Administration of the above-described parenteral co-formulations can be by periodic injections of a bolus of the preparation, or can be administered by intravenous administration from a reservoir which is external (e.g., an i.v. bag).

5.4 Treatment of Fabry Disease with ERT and an ASSC

In accordance with the application, there are provided methods of using α-Gal A (e.g., rhα-Gal A) in combination with an ASSC for the α-Gal A (e.g., DGJ). One embodiment of the present application provides for combination therapy of α-Gal A (e.g. rhα-Gal A ERT) and an ASSC, wherein the α-Gal A and ASSC are co-formulated together and administered to a subject concurrently as a co-formulation. In certain embodiments, the ASSC 1-deoxygalactonojirimycin is co-formulated with α-Gal A as a pharmaceutical composition.

In certain embodiments, the route of administration is intravenous. Administration can be by periodic injections of a bolus of the preparation, or as a sustained release dosage form over long periods of time, such as by intravenous administration, for example, from a reservoir which is external (e.g., an IV bag).

In certain embodiments, the α-Gal A enzyme and DGJ are combined to create a co-formulation for administration to a subject, wherein the dosage of α-Gal A enzyme of the co-formulation administered to the subject is between about 0.05 and about 10 mg/kg, or between about 0.1 and about 5 mg/kg, or between about 0.2 and about 4 mg/kg, or between about 0.3 and about 3 mg/kg, or between about 0.4 and about 2 mg/kg, or between about 0.5 and about 1.5 mg/kg, or between about 0.5 and about 1 mg/kg. Concentrations and ranges intermediate to the above recited concentrations are also intended to be part of this application.

In certain embodiments, the dosage of α-Gal A enzyme of the co-formulation administered to the subject is about 0.05, 0.1, 0.2, 0.3, 0.4, 0.5, 1, 1.5, 2, 2.5, 3, 3.5, 4, 4.5, or 5 mg/kg.

In certain embodiments, the α-Gal A enzyme and DGJ are combined to create a co-formulation for administration to a subject, wherein the dosage of DGJ of the co-formulation administered to the subject is between about 0.05 and 20 mg/kg, or between about 0.1 and about 15 mg/kg, or between about 0.2 and about 10 mg/kg, or between about 0.3 and about 10 mg/kg, or between about 0.4 and about 9 mg/kg, or between about 0.5 and about 8 mg/kg, or between about 0.6 and about 7 mg/kg, or between about 0.7 and about 6 mg/kg, or between about 0.8 and about 5 mg/kg, or between about 0.9 and about 4 mg/kg, or between about 1 and about 3 mg/kg, or between about 1.5 and about 2 mg/kg. Concentrations and ranges intermediate to the above recited concentrations are also intended to be part of this application.

In certain embodiments, the dosage of DGJ of the co-formulation administered to the subject is about 0.05, 0.1, 0.2, 0.3, 0.4, 0.5, 0.6, 0.7, 0.8, 0.9, 1, 2, 3, 4, 5, 6, 7, 8, 9 or 10 mg/kg.

In certain embodiments, the co-formulation composition of the application comprises α-Gal A enzyme and DGJ, wherein the dosage of α-Gal A of the co-formulation administered to a subject is at a concentration selected from the group consisting of 0.3, 0.5, 1, 2 and 3 mg/kg; and wherein the dosage of DGJ of the co-formulation administered to the subject is at a concentration selected from the group consisting of 0.1, 0.3, 0.5, 1, 3, and 10 mg/kg.

The present invention also provides the use of a co-formulation of α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount between about 0.1 and about 0.5 mg/kg, and the DGJ of the co-formulation is formulated for administration in an amount between about 0.1 and about 15 mg/kg.

The present invention also provides the use of a co-formulation of α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount of about 0.3, 0.5, 1, 2 or 3 mg/kg, and the DGJ of the co-formulation is formulated for administration in an amount of about 0.1, 0.3, 0.5, 1, 3, or 10 mg/kg.

The present invention also provides the use of a co-formulation of α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount between about 0.05 and about 10 mg/kg, or between about 0.1 and about 5 mg/kg, or between about 0.2 and about 4 mg/kg, or between about 0.3 and about 3 mg/kg, or between about 0.4 and about 2 mg/kg, or between about 0.5 and about 1.5 mg/kg, or between about 0.5 and about 1 mg/kg; and the DGJ of the co-formulation is formulated for administration in an amount between about 0.05 and 20 mg/kg, or between about 0.1 and about 15 mg/kg, or between about 0.2 and about 10 mg/kg, or between about 0.3 and about 10 mg/kg, or between about 0.4 and about 9 mg/kg, or between about 0.5 and about 8 mg/kg, or between about 0.6 and about 7 mg/kg, or between about 0.7 and about 6 mg/kg, or between about 0.8 and about 5 mg/kg, or between about 0.9 and about 4 mg/kg, or between about 1 and about 3 mg/kg, or between about 1.5 and about 2 mg/kg.

The present invention also provides the use of a co-formulation of α-Gal A and DGJ or a pharmaceutically acceptable salt thereof in the preparation of a medicament for the treatment of Fabry disease, wherein the medicament is formulated for parenteral administration to a subject, and wherein the α-Gal A of the co-formulation is formulated for administration in an amount of about 0.05, 0.1, 0.2, 0.3, 0.4, 0.5, 1, 1.5, 2, 2.5, 3, 3.5, 4, 4.5, or 5 mg/kg; and the DGJ of the co-formulation is formulated for administration in an amount of about 0.05, 0.1, 0.2, 0.3, 0.4, 0.5, 0.6, 0.7, 0.8, 0.9, 1, 2, 3, 4, 5, 6, 7, 8, 9 or 10 mg/kg.

The present invention also provides a co-formulation of α-Gal A and DGJ or a pharmaceutically acceptable salt thereof for use in the treatment of Fabry disease, wherein the co-formulation is administered parenterally, and wherein the α-Gal A of the co-formulation is administered in an amount between about 0.1 and about 0.5 mg/kg, and the DGJ of the co-formulation is administered in an amount between about 0.1 and about 15 mg/kg.

The present invention also provides a co-formulation of α-Gal A and DGJ or a pharmaceutically acceptable salt thereof for use in the treatment of Fabry disease, wherein the co-formulation is administered parenterally, and wherein the α-Gal A of the co-formulation is administered in an amount of about 0.3, 0.5, 1, 2 or 3 mg/kg, and the DGJ of the co-formulation is administered in an amount of about 0.1, 0.3, 0.5, 1, 3, or 10 mg/kg.

The present invention also provides a co-formulation of α-Gal A and DGJ or a pharmaceutically acceptable salt thereof for use in the treatment of Fabry disease, wherein the co-formulation is administered parenterally, and wherein the α-Gal A of the co-formulation is administered in an amount between about 0.05 and about 10 mg/kg, or between about 0.1 and about 5 mg/kg, or between about 0.2 and about 4 mg/kg, or between about 0.3 and about 3 mg/kg, or between about 0.4 and about 2 mg/kg, or between about 0.5 and about 1.5 mg/kg, or between about 0.5 and about 1 mg/kg; and the DGJ of the co-formulation is administered in an amount between about 0.05 and 20 mg/kg, or between about 0.1 and about 15 mg/kg, or between about 0.2 and about 10 mg/kg, or between about 0.3 and about 10 mg/kg, or between about 0.4 and about 9 mg/kg, or between about 0.5 and about 8 mg/kg, or between about 0.6 and about 7 mg/kg, or between about 0.7 and about 6 mg/kg, or between about 0.8 and about 5 mg/kg, or between about 0.9 and about 4 mg/kg, or between about 1 and about 3 mg/kg, or between about 1.5 and about 2 mg/kg.

The present invention also provides a co-formulation of α-Gal A and DGJ or a pharmaceutically acceptable salt thereof for use in the treatment of Fabry disease, wherein the co-formulation is administered parenterally, and wherein the α-Gal A of the co-formulation is administered in an amount of about 0.05, 0.1, 0.2, 0.3, 0.4, 0.5, 1, 1.5, 2, 2.5, 3, 3.5, 4, 4.5, or 5 mg/kg; and the DGJ of the co-formulation is administered in an amount of about 0.05, 0.1, 0.2, 0.3, 0.4, 0.5, 0.6, 0.7, 0.8, 0.9, 1, 2, 3, 4, 5, 6, 7, 8, 9 or 10 mg/kg.

In one non-limiting embodiment, DGJ and recombinant human α-Gal A administered as a co-formulation show surprising efficacy on plasma enzyme activity and enzyme uptake into tissue. In wild-type mice, the plasma half-life of recombinant human α-Gal A (rhα-Gal A) increased 5-fold following a single intravenous injection of a co-formulation of α-Gal A and DGJ, and plasma AUC was increased 4-fold compared to intravenous administration of α-Gal A alone. Additionally, in wild-type mice, the tissue uptake of α-Gal A into kidney and heart tissue was increased up to 1.5-fold following a single intravenous injection of a co-formulation of α-Gal A and DGJ compared to intravenous administration of α-Gal A alone.

In one non-limiting embodiment, DGJ and recombinant human α-Gal A administered as a co-formulation show surprising efficacy on plasma enzyme activity, on enzyme uptake into tissue, and GL-3 reduction in tissue. In mice deficient for endogenous α-Gal A expression (i.e., GLA knockout mice) the plasma half-life of recombinant human α-Gal A (rhα-Gal A) increased up to 3-fold at 0.5 hr, and up to 6-fold at 1 hr following a single intravenous injection of a co-formulation of α-Gal A and DGJ. Additionally, there was a greater GL-3 reduction, and increase in α-Gal A in heart and kidney tissue of the mice after intravenous administration compared to treatment with α-Gal A alone.

In certain non-limiting embodiments, the co-formulation of α-Gal A and DGJ can be administered intravenously to a subject in an amount effective to achieve a plasma AUC concentration of between about 0.5 and 10-fold, or between about 1 and about 8-fold, or between about 1.5 and about 6-fold, or between about 2 and about 5.5-fold, or between about 2.5 and about 5-fold, or between about 3 and about 4.5-fold of the plasma AUC concentration achieved when α-Gal A is administered to a subject in the same dosage as the co-formulation, but in the absence of DGJ.

In certain non-limiting embodiments, the co-formulation of α-Gal A and DGJ can be administered intravenously to a subject in an amount effective to achieve a level of α-Gal A tissue uptake of between about 0.5 and 10-fold, or between about 1 and about 8-fold, or between about 1.5 and about 6-fold, or between about 2 and about 5.5-fold, or between about 2.5 and about 5-fold, or between about 3 and about 4.5-fold of the level of α-Gal A tissue uptake achieved when α-Gal A is administered to a subject in the same dosage as the co-formulation, but in the absence of DGJ.

Delivery of the co-formulation can be continuous over a pre-selected administration period ranging from several hours, one to several weeks, one to several months, or up to one or more years. In certain embodiments, the dosage form is one that is adapted for delivery of α-Gal A over an extended period of time. Such delivery devices may be adapted for administration of α-Gal A for several hours (e.g., 2 hours, 12 hours, or 24 hours to 48 hours or more), to several days (e.g., 2 to 5 days or more, from about 100 days or more), to several months or years. In some of these embodiments, the device is adapted for delivery for a period ranging from about 1 month to about 12 months or more. The α-Gal A delivery device can be one that is adapted to administer α-Gal A to an individual for a period of, e.g., from about 2 hours to about 72 hours, from about 4 hours to about 36 hours, from about 12 hours to about 24 hours; from about 2 days to about 30 days, from about 5 days to about 20 days, from about 7 days to about 100 days or more, from about 10 days to about 50 days; from about 1 week to about 4 weeks; from about 1 month to about 24 months or more, from about 2 months to about 12 months, from about 3 months to about 9 months; or other ranges of time, including incremental ranges, within these ranges, as needed.

In certain embodiments, the methods of the application include administering to an individual, for example, by intravenous administration, a dose of α-Gal A present in a co-formulation with DGJ, wherein the dose is administered once per day, once every two days, once every three days, once every four days, once every five days, or once every six days. In certain embodiments, the dose does not result in a toxic level of α-Gal A in the liver of the individual. In some embodiments, the co-formulation of α-Gal A and DGJ is administered in a sufficient dose to result in a peak concentration of α-Gal A in tissues of the subject, within about 24 hours after the administration of the dose. In certain embodiments, the co-formulation is administered in a sufficient dose to result in a peak concentration of α-Gal A in tissues of the subject within between about 0.2 to about 50 hours, or between about 0.2 to about 24 hours, or between about 0.2 to about 5 hours, or between about 0.2 to about 1 hour, or between about 0.2 to about 0.5 hour, or about 40, 30, 20, 10, 5, 1, 0.5 or fewer hours after the administration of the dose. Ranges intermediate to the above recited ranges are also intended to be part of this application. In some embodiments, the co-formulation is administered as a single-dose. In some embodiments, the co-formulation is administered as a multi-dose.

5.5 Treatment of Fabry Disease with Intravenous DGJ

In accordance with the application, there are provided methods of using intravenous administration of DGJ or salts thereof for the treatment of Fabry disease. In one or more embodiments, a salt such as DGJ HCl is used.

Administration can be by periodic injections of a bolus of the preparation, or as a sustained release dosage form over long periods of time, such as by intravenous administration, for example, from a reservoir which is external (e.g., an IV bag).

In certain embodiments, the dosage of DGJ of salt thereof administered to the subject is between about 0.05 and 20 mg/kg, or between about 0.1 and about 15 mg/kg, or between about 0.2 and about 10 mg/kg, or between about 0.3 and about 10 mg/kg, or between about 0.4 and about 9 mg/kg, or between about 0.5 and about 8 mg/kg, or between about 0.6 and about 7 mg/kg, or between about 0.7 and about 6 mg/kg, or between about 0.8 and about 5 mg/kg, or between about 0.9 and about 4 mg/kg, or between about 1 and about 3 mg/kg, or between about 1.5 and about 2 mg/kg. Concentrations and ranges intermediate to the above recited concentrations are also intended to be part of this application.

In certain embodiments, the dosage of DGJ or salt thereof administered to the subject is about 0.05, 0.1, 0.2, 0.3, 0.4, 0.5, 0.6, 0.7, 0.8, 0.9, 1, 2, 3, 4, 5, 6, 7, 8, 9 or 10 mg/kg.

In certain embodiments, the methods of the application include administering to an individual, for example, by intravenous administration, a dose of DGJ or salt thereof, wherein the dose is administered once per day, once every two days, once every three days, once every four days, once every five days, once every six days, once a week or once every two weeks. In some embodiments, the DGJ is administered as a single-dose. In some embodiments, the DGJ is administered as a multi-dose.

In certain embodiments, the DGJ is co-administered with α-Gal A enzyme, such as in a co-formulation. The co-formulation can have any of the features described above.

5.6 In Vitro Stability

Ensuring the stability of a replacement protein formulation during its shelf life is a major challenge. For example, vials of recombinant enzyme are often for single use only and unused product should be discarded. Additionally, recombinant enzyme often must often be reconstituted, diluted, and administered by a health care professional, and that administration should be without delay. Recombinant enzymes must often be stored at low temperatures, for example, 2 to 8° C., and the product only stable for a limited amount of time, for example, up to 24 hours.

When an ASSC and α-Gal A are present in the same composition, the co-formulated compositions of the application provide more stable compositions. In addition to stabilizing the administered protein in vivo, the ASSC reversibly binds to and stabilizes the conformation of the α-Gal A in vitro, thereby preventing aggregation and degradation, and extending the shelf-life of the co-formulation. Analysis of the ASSC/replacement protein interaction can be evaluated using techniques well-known in the art, such as, for example, differential scanning calorimetry, or circular dichroism.

For example, where an aqueous injectable co-formulation of the composition is supplied in a stoppered vial suitable for withdrawal of the contents using a needle and syringe, the presence of an ASSC inhibits aggregation of the α-Gal A. The vial could be for either single use or multiple uses. In another embodiment, the co-formulation is in a dry or lyophilized state, which would require reconstitution with a standard or a supplied, physiological diluent to a liquid state. In this instance, the presence of an ASSC stabilizes the α-Gal A during and post-reconstitution to prevent aggregation. In the embodiment where the co-formulation is a liquid for intravenous administration, such as in a sterile bag for connection to an intravenous administration line or catheter, the presence of an ASSC confers the same benefit.

In addition to stabilizing the replacement protein to be administered, the presence of an ASSC enables the α-Gal A co-formulation to be stored at a neutral pH of about 7.0-7.5. This confers a benefit to proteins that normally must be stored at a lower pH to preserve stability. For example, lysosomal enzymes, such as α-Gal A, typically retain a stable conformation at a low pH (e.g., 5.0 or lower). However, extended storage of the replacement enzyme at a low pH may expedite degradation of the enzyme and/or co-formulation. In certain embodiments, the co-formulations of the present application remain stable at a pH of between about 5 and about 9, or between about 6 and about 8, or between about 6.5 and about 7.5, or between about 7 and about 7.5.

As described above, the liquid co-formulation of the application has advantageous stability and storage properties. Stability of the liquid co-formulation is not dependent on the form of storage, and includes, but is not limited to, co-formulations which are frozen, lyophilized, spray-dried, or co-formulations in which the active ingredient is suspended. Stability can be measured at a selected temperature for a selected time period. In one aspect of the application, the protein in the liquid co-formulations is stable in a liquid form for at least about 1 week; at least about 2 weeks; at least about 3 weeks; at least about 1 month; at least about 2 months; at least about 3 months; at least about 4 months, at least about 5 months; at least about 6 months; at least about 12 months; at least about 18 months. Values and ranges intermediate to the above recited time periods are also intended to be part of this application, e.g., about 3, 4, 5, 6, 7, 8, 9, 10, 11, 12, 13, 14, 15, 16, 17, 18, 19, 20, 21, 22, 23, or about 24 months. In addition, ranges of values using a combination of any of the above recited values as upper and/or lower limits are intended to be included.

In certain embodiments, the co-formulation is stable at room temperature (about 30° C.) or at about 37° C., or at about 40° C., or at about 45° C. for at least about 1 month and/or stable at about 2-8° C. for at least about 1 year, or more preferably stable at about 2-8° C. for at least about 2 years. In certain embodiments, the co-formulation is stable at a temperature of between about 35 and about 90° C., or between about 40 and about 85° C., or between about 45 and about 80° C., or between about 50 and about 75° C., or between about 55 and about 70° C., or between about 60 and about 70° C. Furthermore, the co-formulation is preferably stable following freezing (to, e.g., −80° C.) and thawing of the co-formulation, hereinafter referred to as a "freeze/thaw cycle."

Stability of a protein (e.g., protein stability and/or reduction in contamination) in a liquid co-formulation can also be defined as the percentage of monomer, aggregate, or fragment, or combinations thereof, of the protein in the co-formulation. In certain embodiments, a protein "retains its physical stability" in a co-formulation if it shows substantially no signs of aggregation, precipitation and/or denaturation upon visual examination of color and/or clarity, or as measured by UV light scattering or by size exclusion chromatography, non-denaturing PAGE, or other methods for determining size, etc. In one aspect of the application, a stable liquid co-formulation is a co-formulation having less than about 10%, or less than about 5%, or less than about 5%, or less than about 4%, or less than about 3%, or less than about 2%, or less than about 1% of the protein being present as aggregate in the co-formulation.

In one embodiment, the physical stability of a liquid co-formulation is determined by determining turbidity of the co-formulation following a stir stress assay, e.g., 24 hour or 48-hour stir-stress assay. For example, a stir stress assay can be performed by placing a suitable volume of a liquid co-formulation in a beaker with a magnetic stirrer, e.g., (multipoint HP, 550 rpm), removing aliquots at any suitable time, e.g., at T0-T48 (hrs), and performing suitable assays as desired on the aliquots. Samples of a co-formulation under the same conditions but without stirring serve as control.

Turbidity measurements can be performed using a laboratory turbidity measurement system from Hach (Germany) and are reported as nephelometric units (NTU).

Stability of the composition (e.g., protein stability and/or reduction in contamination) can also be measured, e.g., by measuring protein degradation or contaminant growth or presence. Protein degradation can be determined, e.g., by reverse phase HPLC, non-denaturing PAGE, ion-exchange chromatography, peptide mapping, or similar methods.

The stability of α-Gal A in the presence of an ASSC, at a concentration described herein, can be measured, e.g., as a percent aggregation or degradation, at a predetermined time and compared with one or more standards. For example, a suitable standard is a composition similar to the test conditions except that the α-Gal A is not contacted with an ASSC. The stabilities of the α-Gal A at a concentration are compared. Suitability can be shown by the α-Gal A at a particular concentration in combination with an ASSC having comparable or better stability than in the absence of the ASSC.

5.7 In Vivo Stability

As described above for the in vitro co-formulations, the presence of an ASSC for the α-Gal A has the benefit of prolonging in plasma the half-life of the exogenous α-Gal A, thereby maintaining effective replacement protein levels over longer time periods, resulting in increased exposure of clinically affected tissues to the α-Gal A and, thus, increased uptake of protein into the tissues. This confers such beneficial effects to the patient as enhanced relief, reduction in the frequency, and/or reduction in the amount administered. This will also reduce the cost of treatment.

In addition to stabilizing wild-type replacement α-Gal A, the ASSC will also stabilize and enhance expression of endogenous mutant α-Gal A that are deficient as a result of mutations that prevent proper folding and processing in the ER, as in conformational disorders such as Fabry Disease.

The compositions and methods of the present application are not to be limited in scope by the specific embodiments described herein and the Examples that follow. Indeed, various modifications of the compositions and methods described by the present application, in addition to those described herein, will become apparent to those skilled in the art from the foregoing description and the accompanying Examples and Figures. Such modifications are intended to fall within the scope of the appended claims.

EXAMPLES

Example 1: Pharmacokinetics and Tissue Uptake of Rhα-Gal A and DGJ-HCl Administered Intravenously to Wild-Type Mice The pharmacokinetics (PK) and tissue uptake of a co-formulation of recombinant human α-Gal A (rhα-Gal A) and 1-deoxygalactonojirimycin-HCl (DGJ-HCl) were determined following a single intravenous (IV) infusion administration to wild-type (WT) mice. (1-deoxygalactonojirimycin is also referred to as "AT1001", recombinant human α-Gal A is also referred to as "JR051").

Eight-week old male WT C57BL/6 mice (n=5) received either rhα-Gal A 1 mg/kg alone (via jugular vein IV infusion) or co-formulated with 3 or 10 mg/kg of DGJ-HCl (free base equivalents of 3.66 and 12.2 mg/kg DGJ-HCl, respectively). Table 1 describes the molar ratios of these compounds:

TABLE 1

| JR-051 (mg/kg) | AT1001 (mg/kg) | JR-051 (µM) | AT1001 (µM) | Ratios in co-formulation mixture (AT1001:JR-051) |
|---|---|---|---|---|
| 1 | 3 | 4 | 4490 | 1122:1 |
| 1 | 10 | 4 | 14950 | 3740:1 |

Plasma was collected at 0, 15, 30, 45, 60, and 90 min, and 24 hrs post-JR-051. Skin, heart, and kidney were collected 24 hrs post-JR-051. JR-051 plasma levels and tissue uptake were assessed by activity and Western blotting (see Methods section below). A comparison was made between JR-051 administered alone and JR-051 co-formulated with AT1001 groups.

Results

Figure 1:
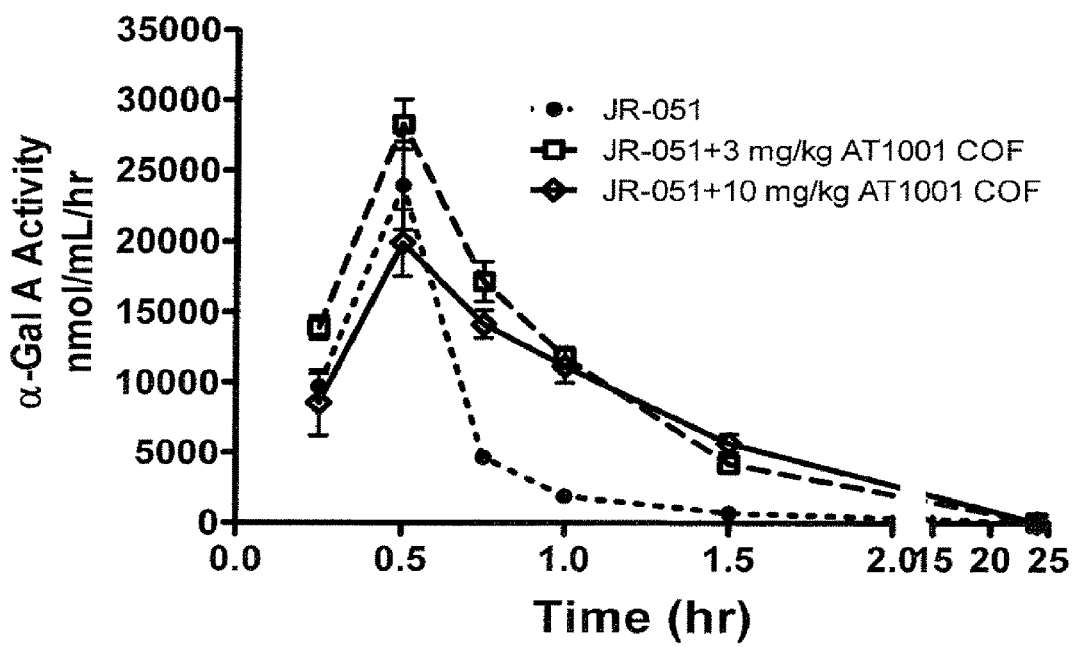
FIG. 1 shows plasma PK of α-Gal A (JR-051) in WT mice following IV infusion administration of α-Gal A or a co-formulation of α-Gal A and DGJ-HCl, as described in Example 1. (DGJ or 1-deoxygalactonojirimycin is also referred to as "AT1001"). The co-formulated composition is referred to as "COF" in the graph.
Figure 2:
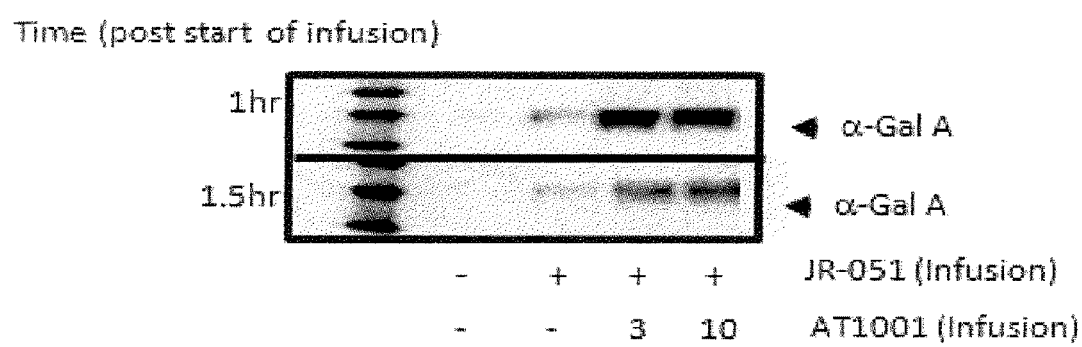
FIG. 2 shows the level of plasma α-Gal A (JR-051) as measured by Western blot in WT mice following IV infusion administration of α-Gal A or a co-formulation of α-Gal A and DGJ-HCl, as described in Example 1. "+": 1 mg/kg JR-051; "−": no compound (either JR-051, or DGJ, or both).

Plasma:

Plasma PK of α-Gal A (JR-051) in WT mice following IV infusion administration is shown in FIGS. 1 and 2. Co-formulation of DGJ with α-Gal A improves α-Gal A PK (as measured by activity and Western blot) in WT mice. Overall, co-formulating DGJ with α-Gal A increases α-Gal A AUC and half-life up to 4- and 5-fold, respectively, as shown in Table 2, below. The effect of DGJ on plasma α-Gal A levels is dose-dependent.

TABLE 2

Summary of half-life and AUC of α-Gal A ± DGJ

| Group | $T_{1/2}$ (hr) | AUC (nmol/mL) |
|---|---|---|
| JR-051 alone | 0.11 | 17960 |
| JR-051 + 3 mg/kg DGJ COF | 0.37 | 67307 |
| JR-051 + 10 mg/kg DGJ COF | 0.56 | 79799 |

Heart and Kidney Tissue:

Co-formulating DGJ with α-Gal A improves α-Gal A uptake into kidney as well as in heart tissue (as measured by activity and Western blot) in wild-type mice, as shown in FIG. 3. Overall, co-formulating DGJ with α-Gal A increases α-Gal A uptake up to 1.5-fold greater than seen with administration of α-Gal A alone. In skin, there was no significant effect seen with either α-Gal A or co-formulated α-Gal A+DGJ (data not shown).

Example 2: Pharmacokinetics, Tissue Uptake and Substrate Reduction of Rhα-Gal a and DGJ-HCl Administered Intravenously to GLA Knockout Mice The pharmacokinetics (PK), tissue uptake and substrate reduction in disease-relevant tissue of a co-formulation of recombinant human α-Gal A (rhα-Gal A) and 1-deoxygalactonojirimycin-HCl (DGJ-HCl) were determined following a single intravenous (IV) infusion administration to GLA knockout mice (GLA KO) (i.e., mice deficient for endogenous α-Gal A expression).

Twelve-week old male GLA KO mice (n=6) received either JR-051: 0.3, 1, or 3 mg/kg alone via jugular vein IV infusion or co-formulated with 1, 3, and 10 mg/kg DGJ (free base equivalents of 1.22, 3.66, and 12.2 mg/kg DGJ-HCl, respectively). Plasma was collected 0.5 and 1 hr after start of infusion to measure JR-051 levels. Enzyme uptake and GL-3 levels were measured in heart, and kidney 7 days post-JR-051 administration (see Methods section below). Table 3 describes the molar ratios of these compounds:

TABLE 3

| JR-051 (mg/kg) | AT1001 (mg/kg) | JR-051 (µM) | AT1001 (µM) | Ratios in co-formulation mixture (AT1001:JR-051) |
|---|---|---|---|---|
| 0.3 | 1 | 1.2 | 1495 | 1246:1 |
| 0.3 | 3 | 1.2 | 4490 | 3742:1 |
| 0.3 | 10 | 1.2 | 14950 | 12460:1 |
| 1 | 1 | 4 | 1495 | 374:1 |
| 1 | 3 | 4 | 4490 | 1122:1 |
| 1 | 10 | 4 | 14950 | 3740:1 |
| 3 | 1 | 12 | 1495 | 125:1 |
| 3 | 3 | 12 | 4490 | 374:1 |
| 3 | 10 | 12 | 14950 | 1250:1 |

Results

Plasma:

Plasma levels of JR-051 in GLA KO mice following IV infusion administration are shown in FIG. 4. There is a dose-dependent increase in the circulating levels of α-Gal A alone in GLA KO mice. Co-formulating DGJ with α-Gal A further increases the circulating levels of α-Gal A. Overall, DGJ co-formulation increases plasma levels of α-Gal A up to 3-fold at 0.5 hr. and up to 6-fold at 1 hr, from start of infusion.

Heart Tissue:

Tissue uptake and reduction in GL-3 in heart tissue of GLA KO mice is shown in FIGS. 5 and 6. There is a dose-dependent GL-3 reduction and α-Gal A increase seen with α-Gal A administration alone in heart. Overall, the co-formulation of DGJ and α-Gal A lead to greater GL-3 reduction and α-Gal A activity than seen with administration of α-Gal A alone. Though the effect of co-formulating α-Gal A and DGJ on α-Gal A activity in heart tissue seems to be dose-dependent with regard to DGJ, the dose-dependent effect was not obvious for GL-3 reduction. GL-3 reduction in heart indicates that when DGJ is co-formulated with lower doses of α-Gal A (e.g., 0.3 or 1 mg/kg), the potency of α-Gal A is increased, achieving effects similar to those of higher doses of α-Gal A alone (3 mg/kg).

Kidney Tissue:

Tissue uptake and reduction in GL-3 in kidney tissue of GLA KO mice is shown in FIGS. 7 and 8. There is a dose-dependent GL-3 reduction and α-Gal A increase seen with α-Gal A administration alone in kidney. Overall, the co-formulation of DGJ and α-Gal A lead to greater GL-3 reduction and α-Gal A activity than seen with administration of α-Gal A alone. Though the effect of co-formulating α-Gal A and DGJ on α-Gal A activity in kidney tissue seems to be dose-dependent with regard to DGJ, the dose-dependent effect was not obvious for GL-3 reduction. GL-3 reduction in kidney indicates that when DGJ is co-formulated with lower doses of α-Gal A (e.g., 1 mg/kg), the potency of α-Gal A is increased, achieving effects similar to those of higher doses of α-Gal A alone (3 mg/kg).

Example 3: Pharmacokinetics, Tissue Uptake and Substrate Reduction of Rhα-Gal a and DGJ-HCl Administered Intravenously to GLA Knockout Mice Repeat administration of co-formulated product was tested in fourteen-week old GLA KO mice. The mice received four biweekly (once every two weeks) IV bolus injections of 0.5, 1 or 3 mg/kg α-Gal A (JR-051) alone, or co-formulated with 0.3, 1, 3 or 10 mg/kg of DGJ (AT1001). Table 4 describes the molar ratios of these compounds. Plasma and tissue levels of α-Gal A, and tissue levels of GL-3 were measured.

TABLE 4

| JR-051 (mg/kg) | AT1001 (mg/kg) | JR-051 (μM) | AT1001 (μM) | Ratios in co-formulation mixture (AT1001:JR-051) |
|---|---|---|---|---|
| 0.5 | 0.3 | 2 | 449 | 224:1 |
| 0.5 | 1 | 2 | 1495 | 747:1 |
| 0.5 | 3 | 2 | 4490 | 2245:1 |
| 0.5 | 10 | 2 | 14950 | 7475:1 |
| 1 | 0.3 | 4 | 449 | 112:1 |
| 1 | 1 | 4 | 1495 | 374:1 |
| 1 | 3 | 4 | 4490 | 1122:1 |
| 1 | 10 | 4 | 14950 | 3740:1 |
| 3 | 0.3 | 12 | 449 | 37:1 |
| 3 | 1 | 12 | 1495 | 125:1 |
| 3 | 3 | 12 | 4490 | 374:1 |
| 3 | 10 | 12 | 14950 | 1246:1 |

Results

α-Gal A Plasma Levels

Administration of the DGJ co-formulation showed trends for increased α-Gal A levels. Plasma collected for 1-hour time point analysis of α-Gal A levels was collected over a 1-2 hour window. Plasma collected for 2-hour time point analysis of α-Gal A levels was collected over a 3-4.5 hour window.

α-Gal Tissue Uptake

Overall, there was an increase in α-Gal A uptake into disease-relevant tissues (skin, heart, and kidney) with the DGJ co-formulation. Co-formulation with DGJ at 3 and 10 mg/kg resulted in greater tissue uptake at every dose level of α-Gal A. In heart and kidney, when DGJ was administered in combination with lower doses of α-Gal A, the potency of α-Gal A increased, achieving effects similar to those of higher α-Gal A doses alone. Although α-Gal A alone showed dose-dependent tissue uptake, a clear dose-dependent effect of DGJ was not detected in the samples tested in this experiment.

GL-3 Reduction in Tissue

As shown in Tables 5-7 below, and FIG. 11A-C, a dose-dependent GL-3 reduction was observed in skin, heart, and kidney with repeat administration of α-Gal A alone. DGJ co-formulation with all doses of α-Gal A resulted in significantly greater GL-3 reduction in all tissues tested. While a clear dose-dependent effect for DGJ was not detected in the samples tested in this example, higher doses of DGJ (3 and 10 mg/kg) showed greater GL-3 reductions. When lower doses of α-Gal A (e.g., 0.5 or 1 mg/kg) were co-formulated with DGJ (3 or 10 mg/kg), the potency was similar or greater than that achieved with higher doses of α-Gal A alone.

TABLE 5

GL-3% reduction in skin: data normalized to GL-3 levels in untreated KO and WT mouse tissues; % reduction = 100% − % of untreated

| | | α-Gal A (mg/kg) | | |
|---|---|---|---|---|
| Skin | | 0.5 | 1 | 3 |
| DGJ (mg/kg) | 0 | 85.7 | 90.7 | 97.4 |
| | 0.3 | 92.5# | 95.5 | 97.7 |
| | 1 | 90.0 | 95.9 | 98.7# |
| | 3 | 95.4# | 97.0# | 98.7# |
| | 10 | 94.6# | 97.6# | 99.2# | p<0.05 in 2-sided t-test; #: Vs. respective JR-051 alone)

TABLE 6

GL-3% reduction in heart: data normalized to GL-3 levels in untreated KO and WT mouse tissues; % reduction = 100% − % of untreated

| | | α-Gal A (mg/kg) | | |
|---|---|---|---|---|
| Heart | | 0.5 | 1 | 3 |
| DGJ (mg/kg) | 0 | 72.1 | 82.7 | 93.7 |
| | 0.3 | 82.7# | 87.9 | 93.5 |
| | 1 | 77.1 | 88.0 | 98.3# |
| | 3 | 94.7# | 98.5# | 98.6# |
| | 10 | 94.7# | 97.0# | 98.6# | p<0.05 in 2-sided t-test; #: Vs. respective JR-051 alone)

TABLE 7

GL-3% reduction in kidney: data normalized to GL-3 levels in untreated KO and WT mouse tissues; % reduction = 100% − % of untreated

| | | α-Gal A (mg/kg) | | |
|---|---|---|---|---|
| kidney | | 0.5 | 1 | 3 |
| DGJ (mg/kg) | 0 | 42.7 | 54.9 | 69.5 |
| | 0.3 | 48.5 | 59.1 | 64.8 |

TABLE 7-continued

GL-3% reduction in kidney: data normalized to GL-3 levels in untreated KO and WT mouse tissues; % reduction = 100% − % of untreated

| kidney | α-Gal A (mg/kg) | | |
|---|---|---|---|
| | 0.5 | 1 | 3 |
| 1 | 40.1 | 58.3 | 78.8# |
| 3 | 66.3# | 79.4# | 76.0 |
| 10 | 58.5# | 64.5 | 77.1 | p<0.05 in 2-sided t-test; #: Vs. respective JR-051 alone)

Alternative Dosing Regimens

In an alternative regime repeat administration of co-formulated product will be tested in GLA KO mice. The mice will receive either 0.5, 1.0, or 2 mg/kg α-Gal A (JR-051) alone, or co-formulated with 0.3, 1, 3, and 10 mg/kg of DGJ. These compounds will be administered via IV bolus tail vein injection every other week for a total of 4 injections (total duration of study=8 weeks). Table 8 describes the molar ratios of these compounds.

TABLE 8

| JR-051 (mg/kg) | AT1001 (mg/kg) | JR-051 (µM) | AT1001 (µM) | Ratios in co-formulation mixture (AT1001:JR-051) |
|---|---|---|---|---|
| 0.5 | 0.3 | 2 | 449 | 224:1 |
| 0.5 | 1 | 2 | 1495 | 747:1 |
| 0.5 | 3 | 2 | 4490 | 2245:1 |
| 0.5 | 10 | 2 | 14950 | 7475:1 |
| 1 | 0.3 | 4 | 449 | 112:1 |
| 1 | 1 | 4 | 1495 | 374:1 |
| 1 | 3 | 4 | 4490 | 1122:1 |
| 1 | 10 | 4 | 14950 | 3740:1 |
| 2 | 0.3 | 8 | 449 | 56:1 |
| 2 | 1 | 8 | 1495 | 187:1 |
| 2 | 3 | 8 | 4490 | 560:1 |
| 2 | 10 | 8 | 14950 | 1870:1 |

In an alternative regime repeat administration of co-formulated product can be tested in GLA KO mice. The mice will receive either 0.3, 1.0, or 3 mg/kg α-Gal A (JR-051) alone, or co-formulated with 0.5, 1, 3, and 10 mg/kg of DGJ. These compounds will be administered via IV bolus tail vein injection every other week for a total of 4 injections (total duration of study=8 weeks). Table 9 describes the molar ratios of these compounds.

TABLE 9

| JR-051 (mg/kg) | AT1001 (mg/kg) | JR-051 (µM) | AT1001 (µM) | Ratios in co-formulation mixture (AT1001:JR-051) |
|---|---|---|---|---|
| 0.3 | 0.5 | 1.2 | 748 | 623:1 |
| 0.3 | 1 | 1.2 | 1495 | 1246:1 |
| 0.3 | 3 | 1.2 | 4490 | 3742:1 |
| 0.3 | 10 | 1.2 | 14950 | 12458:1 |
| 1 | 0.5 | 4 | 748 | 187:1 |
| 1 | 1 | 4 | 1495 | 374:1 |
| 1 | 3 | 4 | 4490 | 1122:1 |
| 1 | 10 | 4 | 14950 | 3740:1 |
| 3 | 0.5 | 12 | 748 | 62:1 |
| 3 | 1 | 12 | 1495 | 124:1 |
| 3 | 3 | 12 | 4490 | 374:1 |
| 3 | 10 | 12 | 14950 | 1246:1 |

Methods for Examples 1-3

Measurement of Plasma α-Gal A Activity

For plasma α-Gal A activity measurement, samples were diluted ~400-fold with Lysis Buffer (1% Triton X-100, 150 mM NaCl, 25 mM Bis-Tris, pH 6.5) prior to assay. Diluted plasma (20 µL) was added to 50 µL Assay Buffer (27 mM sodium citrate, 46 mM sodium phosphate dibasic, 6 mM 4-methylumbeliferryl-α-D-galactopyranoside (4-MUG), 90 mM N-acetyl-D-galactosamine, pH 4.6) and incubated for 1 hour at 37° C. Reactions were stopped by addition of 70 µL 0.4 M glycine, pH 10.8. Fluorescence at 460 nm was read on a Victor$^3$ plate reader (Perkin Elmer, Waltham, Mass.) after excitation at 355 nm. Raw fluorescence counts were background subtracted (defined by Assay Buffer only). A 4-MU standard curve ranging from 7 nM to 15 µM was run each day for conversion of fluorescence counts to absolute α-Gal A activity, expressed as nanomoles of released 4-MU per milliliter of plasma per hour (nmol/mL/hr).

Measurement of Plasma α-Gal a Protein by Western Blot

Diluted plasma (1:50) in Lysis Buffer (~10 µg total protein) was subjected to SDS-PAGE on 4-12% polyacrylamide gels (Invitrogen, Grand Island, N.Y.), transferred to nitrocellulose membranes (Invitrogen), and immunoblotted with rabbit anti-human α-Gal A primary antibody (1:2000 dilution; from Shire Pharmaceuticals, Cambridge, Mass.). Protein bands were detected using peroxidase-conjugated goat anti-rabbit secondary antibody (Jackson Immunosearch Labs, West Grove, Pa.) in combination with enhanced chemiluminescence (Pierce, Rockford, Ill.). Blots were scanned on an Image Station 4000R (Kodak, Rochester, N.Y.).

Measurement of Tissue α-Gal A Activity (Uptake) and Western Blot

Tissue lysates from mutant mice were prepared by homogenization of ~50 mg tissue for 3 to 5 seconds on ice with a micro-homogenizer (Pro Scientific, Thorofare, N.J.) in 200 µL Lysis Buffer (0.1% Triton X-100, 27 mM sodium citrate, 46 mM sodium phosphate dibasic, pH 4.6). Lysates (20 µL) were added to 50 µL Assay Buffer (27 mM sodium citrate, 46 mM sodium phosphate dibasic, 6 mM 4-methylumbeliferryl-α-D-galactopyranoside (4-MUG), 90 mM N-acetyl-D-galactosamine, pH 4.6) and incubated for 1 hour at 37° C. Reactions were stopped by the addition of 70 µL 0.4 M glycine, pH 10.8. Fluorescence at 460 nm was read on a Victor$^3$ plate reader (Perkin Elmer, Waltham, Mass.) after excitation at 355 nm. Raw fluorescence counts were background subtracted (defined by Assay Buffer only). A BCA Protein Assay (Pierce, Rockford, Ill.) was used according to the manufacturer's instructions to determine total protein concentration in tissue lysates. A 4-MU standard curve ranging from 1.3 nM to 30 mM was run each day for conversion of fluorescence counts to absolute α-Gal A activity, expressed as nanomoles of released 4-MU per milligram of total protein per hour (nmol/mg protein/hr). For tissue Westerns exactly same procedure was followed as described above for plasma except that 50 µg tissue lysate was used.

Measurement of Tissue GL-3 Levels

Mouse tissues were homogenized in water (1:16.7 tissue: water) using a Fast Prep homogenizer (Pro Scientific, Thorofare, N.J.). Acetone:methanol (50:50) was added at 5× the volume of the homogenate. Samples were vortexed, re-homogenized in the Fast Prep system, and centrifuged at 10600 g for 10 minutes at room temperature. Each supernatant (200 µL of the upper organic portion) was prepared for solid phase extraction by addition of 200 µL dimethyl sulfoxide (DMSO), 50 μL lactosyl ceramide internal standard (from bovine buttermilk; Matreya, LLC, Pleasant Gap, Pa.) at a final concentration of 1.4 μg/mL, and 600 μL of water:methanol (13:87), followed by vortexing. Solid phase extraction was conducted on a pre-conditioned Bond Elut 40 μm, 100 mg C-18 column (Varian Inc, Palo Alto, Calif.) by washing with 67:23:10 methanol:acetone:water and elution with 1 mL of 9:1 acetone:methanol into silanized glass culture tubes containing 200 μL 0.2 mM sodium acetate in DMSO. Total GL-3 levels were determined from 20 μL of each sample extract by liquid chromatography-tandem mass spectroscopy (LC-MS/MS). LC was conducted using an acetone:methanol:acetonitrile (ACN) with sodium acetate binary mobile phase system (mobile phase A: 40:60 methanol:water with 0.1 mM sodium acetate; mobile phase B: 75:15:10 acetone:methanol:ACN with 0.1 mM sodium acetate) with a flow rate of 0.5 mL/min on a C18 column (Aqua 3 μm 100×3.0 mm, 125 A, Phenomenex, Torrance, Calif.). The final GL-3 elution condition was 90% mobile phase B. MS/MS analysis was carried out under positive ion mode (ESI+) and twelve different isoforms of GL-3 [C16:0, C18:0, C20:0, C22:1, C22:0, C23:0, C22:0(2OH), C24:2, C24:1, C24:0, C24:1(2OH), C24:0(2OH)] as well as internal standard were identified in each sample. The following transitions were monitored: m/z 1046.70→m/z 884.7 for C16:0; m/z 1074.8→m/z 912.8 for C18:0; m/z 1102.8→m/z 940.8 for C20:0; m/z 1128.8→m/z 966.8 for C22:1; m/z 1130.9→m/z 968.8 for C22:0; m/z 1144.9→m/z 982.8 for C23:0; m/z 1146.9→m/z 984.8 for C22:0(2OH); m/z 1154.9→m/z 992.8 for C24:2; m/z 1156.9→m/z 994.8 for C24:1; m/z 1158.9→m/z 996.9 for C24:0; m/z 1172.9→m/z 1010.8 for C24:1(2OH); m/z 1174.9→m/z 1012.8 for C24:0(2OH); and m/z 982.9→m/z 820.8 for the lactosyl ceramide internal standard. For quantitation, the area counts for each isoform were determined and then summed to obtain the total GL-3 area counts. The ratio of the total GL-3 area counts to that of the internal standard was determined and used to calculate the final concentration of GL-3 in each sample based on a linear least squares fit equation applied to an 11-point calibration curve prepared in DMSO. Total GL-3 measurements were normalized to the wet tissue weight of each sample.

Example 4: Co-Formulating DGJ with α-Gal A Increases α-Gal A Stability in Blood Ex Vivo The effect of co-formulating α-Gal A with DGJ on α-Gal A stability in blood ex vivo was examined. Time-dependent loss of α-Gal A activity in whole blood at 37° C. was determined. 5 nM and 50 nM α-Gal A was formulated with or without 10 μM DGJ. As shown in FIG. 9A-B, the half-life of α-Gal A in the whole blood samples when formulated without DGJ was about 4-5 hours. DGJ stabilized the enzyme and prevented enzyme inactivation.

Figures 10A, 10B, 10C, 10D:
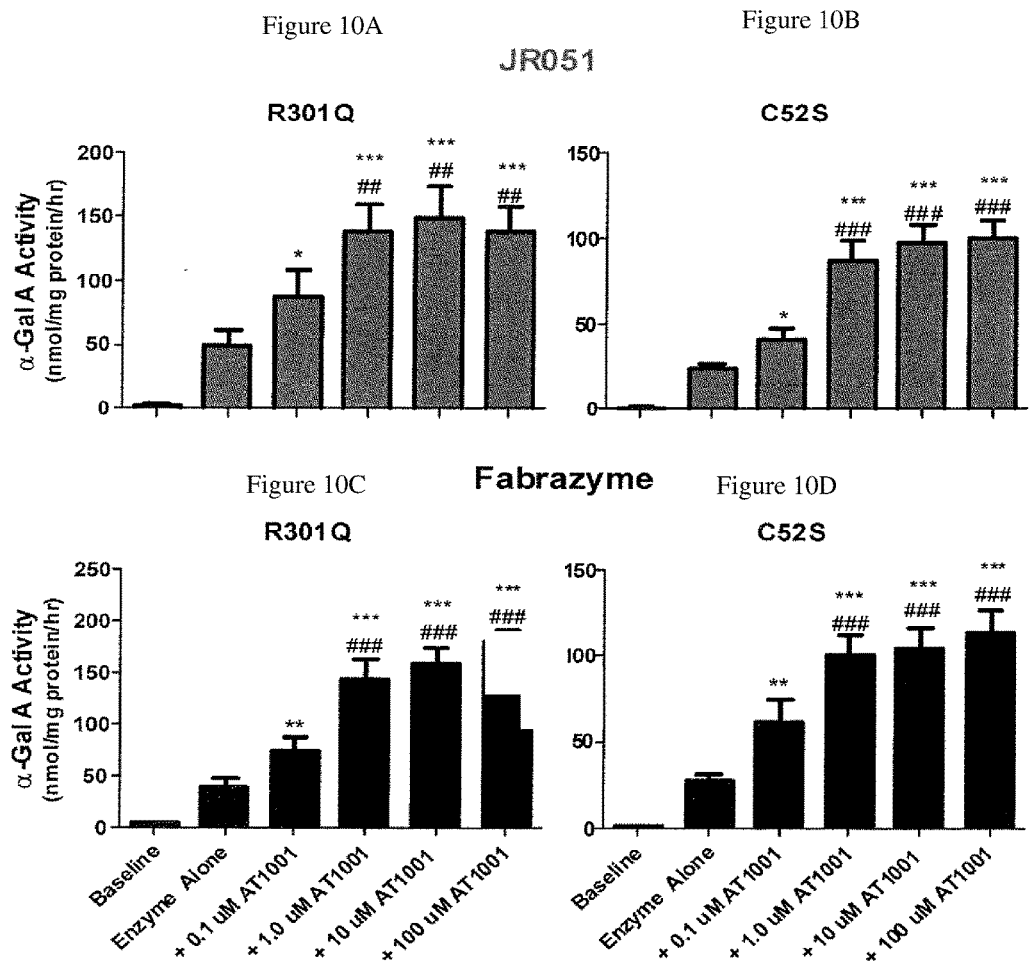

Example 5: Co-Formulating DGJ with α-Gal A Increases Enzyme Uptake and GL-3 Reduction in Fabry Patient Derived Cells The effect of co-formulating α-Gal A with DGJ on α-Gal A uptake and GL-3 reduction in R301Q and C52S fibroblast cells derived from Fabry patients was determined. 0.5 nM α-Gal A was tested alone or co-formulated with 0.1, 1.0, 10 or 100 μM DGJ. As shown in FIGS. 10A and C, in R301Q cells, DGJ increased the uptake of JR051 up to 3-fold compared to up to 4.6-fold with Fabrazyme®. As shown in FIGS. 10B and D, in C52S cells, DGJ increased uptake of both enzymes up to 4.2-fold. The graph bars represent the average of compiled data from 4 separate experiments.

With regard to reducing GL-3 levels, As shown in FIG. 10E-H, in both cell lines, JR051 at 0.5 nM results in similar reduction in GL-3 levels as Fabrazyme® (~70-80% of baseline). Further reduction after co-incubation with DGJ is also similar between the two enzymes (~40-50% of baseline). The graph bars represent the average of compiled data from 4 separate experiments.

Example 6: Pharmacokinetics of Intravenous Administration of DGJ

Healthy volunteers received migalastat HCl (DGJ HCl) via the intravenous (IV) route of administration to evaluate safety, tolerability, and pharmacokinetics. Another study was performed to determine the absolute bioavailability of migalastat after an oral capsule dose as compared to an IV administered dose of migalastat HCl in healthy volunteers. The absolute bioavailability arm was added to determine the exposure ratio of a 150 mg oral dose relative to a 150 mg dose administered as an IV infusion. A list of the primary and secondary objectives and endpoints is provided in Table 10.

TABLE 10

| Objectives | Endpoints |
| --- | --- |
| PRIMARY | |
| Determine the pharmacokinetics of migalastat HCL following a single 2-hour infusion in healthy subjects | Plasma PK: $AUC_{0-\infty}$, $AUC_{0-t}$, $C_{max}$, $t_{max}$, $CL_T$, $V_z$, and $t\frac{1}{2}$ for migalastat |
| Determine the safety and tolerability of a single migalastat HCl 2-hour infusion in healthy subjects | Safety: adverse events (AEs) including infusion site reactions and allergic reactions, clinically significant changes in safety laboratory tests (hematology, chemistry, and urinalysis), vital signs (blood pressure, heart rate, respiratory rate, temperature), physical examinations, and 12-lead electrocardiograms (ECGs) |
| Secondary | |
| Determine dose proportionality of migalastat following a single 2-hour IV infusion in healthy subjects (at doses of 0.3, 1.0, and 10.0 mg/kg) | Plasma PK: $AUC_{0-\infty}$, $AUC_{0-t}$, and $C_{max}$ |

TABLE 10-continued

| Objectives | Endpoints |
|---|---|
| Determine the urinary excretion of the unchanged migalastat following a single 2-hour IV infusion in healthy subjects | Urinary PK: $Ae_{0-24h}$, Fe, $CL_r$ of migalastat |
| Determine the absolute bioavailability of plasma migalastat | Plasma PK: $F_{abs}$, the point estimate for $AUC_{0-\infty}$, $AUC_{0-t}$, ratios and 90% confidence intervals (CIs) |

Type of Study: This Phase 1 study was a single-center study consisting of 2 designs. Cohorts 1, 2, and 3 were performed according to a randomized, double-blind, placebo-controlled, single ascending dose (SAD) IV study design to evaluate the safety, tolerability, and PK of IV administered migalastat HCl or IV administered placebo in healthy subjects. Cohort 4 was an open-label, randomized two-way crossover arm designed to assess the absolute bioavailability of orally administered migalastat HCl relative to IV administered migalastat HCl in healthy subjects. In all cohorts, the duration of the IV infusion with migalastat HCl (or placebo, if applicable) was 2 hours (±10 min) at a constant rate of 125 mL/h.

Cohorts 1, 2, 3: Subjects in Cohorts 1, 2, and 3 received IV administered single ascending doses of migalastat HCl. Seven subjects were enrolled into each cohort (5 subjects randomized to migalastat HCl and 2 subjects randomized to placebo). Dosing of Cohorts 1, 2, and 3 was staggered to allow for safety and tolerability review before proceeding with the next group. Therefore, Cohorts 1, 2, and 3 were each divided into 2 sub-groups: Group A (2 subjects randomized to migalastat HCl and 1 subject randomized to placebo) and Group B (3 subjects randomized to migalastat HCl and 1 subject randomized to placebo). Subjects in Group B were dosed the day following completion of Group A dosing. Except for Cohort 3B, which was dosed 31 days after Cohort 3A because an interim PK review was performed on emerged data from Cohort 3A. Additionally, initiation of infusion was staggered by 60 minutes for Group A subjects, and by 30 minutes for Group B subjects (see FIG. 12).

* In all cohorts, dosing of subjects in Group B started the day after dosing in Group A. Except for Cohort 3B which was dosed 31 days after Cohort 3A, because an interim PK review of Cohort 3A was performed.

Cohort 4: An open-label crossover arm (Cohort 4) was added to assess the absolute bioavailability of orally administered 150 mg migalastat HCl capsule relative to 2-hour IV infusion of 150 mg migalastat HCl. Cohort 4 consisted of 2 sequential treatment periods with a washout period of 7 days between study drug administrations (FIG. 13). Cohort 4 enrolled 10 subjects all of whom received active drug (no placebo was administered). Cohort 4 was randomized such that 5 subjects received the oral formulation and 5 subjects received the IV formulation during Period 1, followed by the alternate formulation during Period 2.

* During Period 1, all Day −1 through Day 3 assessments were performed.  The washout period was 7 days. * During Period 2, subjects repeated all Day −1 through Day 3 assessments.

Dose Escalation This escalating design was chosen to allow careful increase of the dose, after assessment of safety and tolerability of each preceding dose. The IV administered single ascending doses of migalastat HCl include a starting dose of 0.3 mg/kg (Cohort 1), a mid-range dose of 1.0 mg/kg (Cohort 2), and a highest dose of permitted at any time during a cohort based on emergent safety, tolerability, and PK data, up to a maximum allowed dose of 13.0 mg/kg. As per CSP Amendment 3.1 (see Appendix 16.1.1 and Section 9.8.1), the top dose of this study (Cohort 3) was estimated to not exceed the following limit: The maximum exposure (AUC) following oral administration of 1250 mg migalastat HCl of 116 h.µg/mL (115,931 h·ng/mL).

Treatments Administered: In all cohorts, the duration of the IV infusion with migalastat HCl (or placebo, if applicable) was 2 hours (±10 min) at a constant rate of 125 mL/h. Subjects enrolled in Cohorts 1, 2, and 3 were randomized to receive one of the following doses of migalastat HCl (n=5) or placebo (n=2):

Cohort 1 (0.3 mg/kg IV): migalastat HCl (n=5) or placebo (n=2)

Cohort 2 (1.0 mg/kg IV): migalastat HCl (n=5) or placebo (n=2)

Cohort 3 (10.0 mg/kg IV): migalastat HCl (n=5) or placebo (n=2).

Cohort 4: Period 1: 150 mg migalastat HCl capsule (n=5) or 150 mg migalastat HCl via IV infusion (n=5). Period 2: 150 mg migalastat HCl capsule (n=5) or 150 mg migalastat HCl via IV infusion (n=5)

The migalastat HCl used for infusion was 50 mg/ml and the placebo was 0.9% sodium chloride. The oral migalastat HCl was administered as a 150 mg gelatin tablet.

Selection of Doses in the Study: The current single dose levels were selected on the basis of predicted human PK following IV dosing, non-clinical safety margins, and target therapeutic migalastat exposures for efficacy. A starting single IV infusion of 0.3 mg/kg migalastat HCl in humans was selected based on large safety margins (Table 11). Likewise, the migalastat HCl 10 mg/kg dose in humans was supported by previous oral human migalastat exposures and preclinical safety margins (Table 12). Based on a mass-balance study, the recovery of migalastat was high, indicating that migalastat is well absorbed, however, approximately 20% to 25% may represent unabsorbed drug. As such, the predicted exposures were expected to be as much as 1.25-fold greater following IV dosing to account for possible unabsorbed drug following oral dosing.

TABLE 11

Predicted Human Migalastat AUC and $C_{max}$ Following Single IV Dose Administration and Exposure Margins to General Toxicology NOAELs

| Migalastat HCl Dose (mg/kg) | Predicted Median AUC (h · µg/mL) | Fold Cover to NOAEL AUC | | Predicted Median $C_{max}$ (µg/mL) | Fold Cover to NOAEL $C_{max}$ | |
|---|---|---|---|---|---|---|
| | | Rat[1] | Monkey[2] | | Rat[1] | Monkey[2] |
| 0.3 | 1.86 | 134 | 165 | 0.36 | 65 | 68 |
| 10.0 | 61.5 | 4.05 | 4.98 | 12.1 | 1.93 | 2.02 |

Abbreviations:
AUC = area under the concentration-time curve;
$C_{max}$ = maximum observed concentration;
HCl = hydrochloride;
NOAEL = no observed adverse effect level.
[1]Rat NOAEL (1500 mg/kg/day): AUC = 24.9 µg · h/mL, $C_{max}$ = 23.4 µg/mL.
[2]Monkey NOAEL (500 mg/kg/day): AUC = 30.6 µg · h/mL, $C_{max}$ = 24.5 µg/mL.

TABLE 12

Predicted Human Migalastat AUC and $C_{max}$ Following Single IV Dose Administration and Exposure Margins to Human Observed Oral Migalastat Exposures Following a Single Oral Dose of 1250 mg

| Migalastat HCl Dose (mg/kg) | Predicted Median AUC (h · µg/mL) | Fold Cover to AUC from human oral 1250 mg | | | Predicted Median $C_{max}$ (µg/mL) | Fold Cover to $C_{max}$ from human oral 1250 mg | | |
|---|---|---|---|---|---|---|---|---|
| | | Min[1] | Median[2] | Max[3] | | Min[1] | Median[2] | Max[3] |
| 0.3 | 1.86 | 15.5 | 39 | 62 | 0.36 | 2.6 | 36 | 61 |
| 10.0 | 61.5 | 0.47 | 1.19 | 1.89 | 12.1 | 0.08 | 1.07 | 1.81 |

Abbreviations:
AUC = area under the concentration-time curve; $C_{max}$ = maximum observed concentration; HCl = hydrochloride; Max = maximum; Min = minimum.
[1]Minimum observed individual PK exposures: AUC = 28.9 h · µg/mL, $C_{max}$ = 4.78 µg/mL.
[2]Median observed individual PK exposures: AUC = 73.2 h · µg/mL, $C_{max}$ = 13.0 µg/mL.
[3]Maximum observed individual PK exposures: AUC = 115.9 h · µg/mL, $C_{max}$ = 21.9 µg/mL.

Oral administration of the 150 mg migalastat HCl capsule was well tolerated in previous clinical studies conducted in healthy volunteers and Fabry patients. Additionally, single dose administrations up to 2000 mg migalastat HCl to healthy volunteers in Phase 1 studies have been well tolerated. Oral administrations have demonstrated linear exposures to 1250 mg migalastat HCl. A phase 2a study conducted in 23 Fabry patients demonstrated improved tissue uptake of active α-Gal A into skin following co-administration of a single oral administration of 150 mg migalastat HCl with 0.2, 0.5, and 1.0 mg/kg agalsidase. Additionally, oral 150 mg migalastat HCl has been safely administered every other day to Fabry patients with amenable mutations in Phase 2 and 3 studies in the monotherapy program.

Cohorts 1, 2, and 3 (SAD): After a single 2-hour IV infusion of migalastat HCl at doses in the range of 0.3 to 10 mg/kg, maximum arithmetic mean plasma concentrations of migalastat were typically reached at the end of infusion, corresponding to 2 h after start of infusion. The mean migalastat plasma concentration-time profiles displayed a clear dose-dependent increase in plasma concentrations following increasing IV doses of migalastat HCl. After reaching a maximum, the migalastat concentrations decreased rapidly until 12 h post-dose. At the higher dose levels (0.3 mg/kg and 10 mg/kg), the initial rapid decline of migalastat concentrations was followed by a more gradual decline in an apparently biphasic manner (FIG. 14A-B). Combined individual migalastat plasma concentration-time profiles showed minimal inter-individual differences in individual PK profiles across tested IV doses.

After a single 2-hour IV infusion of migalastat HCl at dose levels of 0.3, 1.0, and 10 mg/kg, the median $t_{max}$ of migalastat was 1.93 h post start of the infusion (ie, the end of the infusion). The geometric mean migalastat $C_{max}$ ranged from 609 to 20652 ng/mL and increased with increasing IV dose. The geometric mean $AUC_{0-\infty}$ ranged from 2317 to 81447 h·ng/mL and increased with increasing IV dose as well. The arithmetic mean apparent terminal t½ of migalastat increased from 2.09 to 10.0 h over the IV dose range tested. This increase in t½ with dose appeared to be driven by fewer quantifiable concentrations during the terminal elimination phase at lower IV dose levels (0.3 and 1 mg/kg IV). As a result, the arithmetic mean $V_z$, which was derived from the $CL_T$ and t½, also increased from 19.9 to 107 L with increasing IV dose. Likewise, $V_{ss}$ increased from 17.9 to 27.2 L with increasing IV doses. The arithmetic mean $CL_T$ ranged from 6.59 to 7.68 L/h and was relatively constant across IV doses (see Table 13).

TABLE 13

Summary Statistics of Pharmacokinetic Parameters for Migalastat in Plasma (Cohorts 1-3)

| PK Parameter* | 0.3 mg/kg IV (N = 5) | 1.0 mg/kg IV (N = 5) | 10 mg/kg IV (N = 5) |
|---|---|---|---|
| $C_{max}^a$ (ng/mL) | 609 (5.5%) | 1760 (5.9%) | 20652 (11.4%) |
| $t_{max}^b$ (h) | 1.93 | 1.93 | 1.93 |
| | (1.93-1.95) | (1.93-1.97) | (1.93-1.93) |
| $AUC_{0-t}^a$ (h · ng/mL) | 2282 (7.7%) | 6861 (14.7%) | 81106 (14.5%) |
| $AUC_{0-\infty}^a$ (h · ng/mL) | 2317 (7.4%) | 6917 (14.6%) | 81447 (14.6%) |
| t½ $^c$ (h) | 2.09 (8.9%) | 3.21 (19.5%) | 10.0 (3.1%) |
| $CL_T^c$ (L/h) | 6.59 (4.3%) | 7.68 (14.8%) | 7.40 (9.7%) |
| $V_z^c$ (L) | 19.9 (7.5%) | 35.0 (15.4%) | 107 (10.6%) |
| $V_{ss}^c$ (L) | 17.9 (6.3%) | 24.2 (12.8%) | 27.2 (10.8%) |

CV % = coefficient of variation;
IV = intravenous;
N = number;
PK = pharmacokinetic.
$^a$For $C_{max}$, $AUC_{0-t}$, and $AUC_{0-\infty}$ geometric mean (CV %) are presented.
$^b$For $t_{max}$ median and (minimum-maximum) are presented.
$^c$For t½, $CL_T$, $V_z$, and $V_{ss}$ arithmetic mean (CV %) are presented.

Dose Proportionality

Dose proportionality of plasma migalastat was assessed for the 0.3 to 10 mg/kg single dose range by plotting the dose-normalized parameters $C_{max}$ (FIG. 15A), $AUC_{0-t}$ (FIG. 15B), and $AUC_{0-\infty}$ (FIG. 15C) on a linear scale. Based on regression analysis of dose-normalized these PK parameters versus concentration, the slopes and 90% CIs of the powers of Cmax, AUC0-t, and AUC0-∞ not statistically different from 1 (Table 14). Based on figure of dose-normalized $C_{max}$ versus dose (FIG. 15A), the $C_{max}$ appeared to increase less than dose proportional from 0.3 to 1 mg/kg migalastat HCl, while $C_{max}$ increased dose proportionally from 1.0 to 10 mg/kg migalastat HCl. Similarly, only for the increase from 0.3 to 1.0 mg/kg migalastat HCl, the ratio versus the lowest dose for dose-normalized $C_{max}$ (2.89 [90% CI: 2.64-3.16]) deviated slightly from the theoretical ratio (3.33; see Table 14). Still, for the increase from 0.3 to 10.0 mg/kg migalastat HCl, the ratio versus the lowest dose for dose-normalized Cmax (33.9 [90% CI: 31.0-37.1]) was consistent with the theoretical ratio (33.3). Thus based on the slopes, dose-normalized figures, and ratios with the lowest dose, the exposure parameters of plasma migalastat appeared to be dose proportional over the 0.3 to 10 mg/kg single ascending IV dose range.

TABLE 14

Exploratory Analysis of Dose Proportionality (Cohorts 1-3)

| PK Parameter | Slope | SE | DF | 90% CI Lower | 90% CI Upper |
|---|---|---|---|---|---|
| $C_{max}$ | 0.97 | 0.02 | 13 | 0.94 | 1.00 |
| $AUC_{0-t}$ | 0.98 | 0.02 | 13 | 0.94 | 1.01 |
| $AUC_{0-\infty}$ | 0.98 | 0.02 | 13 | 0.94 | 1.01 |

CI = confidence interval;
DF = degrees of freedom;
PK = pharmacokinetics;
SE = standard error.
Using the power model: parameter = a * dose^b ==> log(parameter) = slope^log(dose) + intercept [+error].
Slope and 90% CIs were determined with the PROC MIXED procedure. A slope close to 1 suggests dose proportionality.

data. The maximum arithmetic mean plasma concentrations were approximately 2-fold higher after IV dosing than after oral dosing of migalastat HCl. After reaching a maximum, for both oral and IV administration of migalastat HCl the migalastat concentrations decreased rapidly followed by a more gradual decline in an apparently biphasic manner (FIG. 16A-B).

Combined individual migalastat plasma concentration-time profiles showed more inter-individual differences in individual PK profiles after oral administration of 150 mg migalastat HCl than after IV administration of 150 mg migalastat HCl. Also the inter-individual differences in PK profiles appeared to be more pronounced after the 150 mg IV dose than after the 0.3 to 10 mg/kg IV dose range, probably related to inter-individual differences in the rate and extent of absorption and clearance after the 150 mg oral dose, or because the 150 mg IV dose was not corrected for the individual subjects' weight.

After a single oral dose of 150 mg migalastat HCl, the median $t_{max}$ of migalastat was 2.75 h post-dose. After a single 2-hour IV infusion of 150 mg migalastat HCl, the median $t_{max}$ of migalastat was 1.93 h post start of the infusion (ie, the end of the infusion) (Table 16).

The geometric mean plasma migalastat $C_{max}$ values were approximately 1.9-fold higher after IV administration ($C_{max}$=3378 ng/mL) than after oral administration ($C_{max}$=1786 ng/mL). The geometric mean $AUC_{0-t}$ and $AUC_{0-\infty}$ values were approximately 1.3-fold higher after IV administration (13167 h·ng/mL and 13253 h·ng/mL, respectively) than after oral administration (9777 h·ng/mL and 9881 h·ng/mL, respectively). Exposures ($AUC_{0-\infty}$) appeared to increase for most (8 of 10) subjects following IV dosing relative to oral (see FIG. 17). The absolute oral bioavail-

TABLE 15

Summary of Statistical Analysis of Dose Proportionality of Migalastat in Plasma - Ratio with Lowest Dose (Cohorts 1-3)

| PK Parameter | Geometric Least Square Means Test | | Geometric Least Square Means Reference | | Ratio Test/Reference Estimate | Ratio Test/Reference (90% CI) | Theoretical Ratio if Dose Proportional |
|---|---|---|---|---|---|---|---|
| $C_{max}$ (ng/mL) | 1.0 mg/kg | 1760 | 0.3 mg/kg | 609 | 2.89 | (2.64, 3.16) | 3.33 |
| | 10 mg/kg | 20652 | 0.3 mg/kg | 609 | 33.9 | (31.0, 37.1) | 33.3 |
| $AUC_{0-t}$ (h · ng/mL) | 1.0 mg/kg | 6861 | 0.3 mg/kg | 2282 | 3.01 | (2.61, 3.47) | 3.33 |
| | 10 mg/kg | 81106 | 0.3 mg/kg | 2282 | 35.5 | (30.8, 41.0) | 33.3 |
| $AUC_{0-\infty}$ (h · ng/mL) | 1.0 mg/kg | 6917 | 0.3 mg/kg | 2317 | 2.99 | (2.59, 3.44) | 3.33 |
| | 10 mg/kg | 81447 | 0.3 mg/kg | 2317 | 35.2 | (30.5, 40.5) | 33.3 |

CI = confidence interval; PK = pharmacokinetic.
Using a model with treatment (dose level in mg/kg) as a fixed factor. The data were natural log transformed and back transformed after the analysis to obtain ratios.

Cohort 4: After oral administration of 150 mg migalastat HCl, migalastat appeared in plasma within 0.25 h to 0.5 h post-dose (0.25 h was the first post-dose sampling time point). Maximum arithmetic mean plasma concentrations of migalastat were typically reached between 2 h and 4 h post oral dose. For most subjects a single peak plasma concentration was observed, except that for Subject 022 an initial peak concentration at 1.5 h was followed by a second and higher peak concentration at 4 h post oral dose. For Subject 030 a similar plateau phase was observed between 1 h and 1.5 h post oral dose, followed by a peak concentration at 3 h post-dose. After IV administration of 150 mg migalastat HCl the maximum arithmetic mean plasma concentrations of migalastat were reached at the end of infusion (corresponding to 2 h after start of infusion), similar to the SAD ability for the 150 mg dose of migalastat HCl was 74.3% (90% CI: 67.0-82.3) based on the $AUC_{0-t}$, and 74.6% (90% CI: 67.2-82.7) based on the $AUC_{0-\infty}$ (Table 15). The individual oral bioavailability values ranged between 56.4% and 97.1% when based on the AUC0-t, and between 56.8% and 97.5% when based on the $AUC_{0-\infty}$.

Although the terminal elimination phase of migalastat was comparable between the oral and IV formulation, the arithmetic mean t½ of migalastat was longer after oral administration of migalastat HCl than after IV administration (7.28 h versus 4.54 h, respectively). This difference in mean t½ between formulations is probably due to fewer quantifiable concentrations during the terminal elimination phase after IV administration compared to oral administration. The arithmetic mean $CL_T/F$ was 12.8 L/h after oral administration and the arithmetic mean $CL_T$ was 9.34 L/h after IV administration of migalastat HCl. The arithmetic mean $V_z/F$ was 123 L after oral administration and the arithmetic mean $V_z$ was 59.4 L after IV administration of migalastat HCl. The arithmetic mean $V_{ss}$ was 30.2 L after IV administration (Table 17).

TABLE 16

Summary Statistics of Pharmacokinetic Parameters for Migalastat in Plasma (Cohort 4)

| PK Parameter* | 150 mg oral (N = 10) | 150 mg IV (N = 10) |
|---|---|---|
| $C_{max}{}^a$ (ng/mL) | 1786 (25.9%) | 3378 (12.6%) |
| $t_{max}{}^b$ (h) | 2.75 (1.50-4.00) | 1.93 (1.93-2.00) |
| $AUC_{0-t}{}^a$ (h · ng/mL) | 9777 (25.7%) | 13167 (14.9%) |
| $AUC_{0-\infty}{}^a$ (h · ng/mL) | 9881 (25.6%) | 13253 (15.0%) |
| $t_{½}{}^c$ (h) | 7.28 (59.2%) | 4.54 (44.8%) |
| $CL_T{}^{c,d}$ (L/h) | 12.8 (26.1%) | 9.34 (14.6%) |
| $V_z{}^{c,d}$ (L) | 123 (46.0%) | 59.4 (33.7%) |
| $V_{ss}{}^{c,e}$ (L) |  | 30.2 (15.0%) |

CV % = coefficient of variation;
IV = intravenous;
N = number;
PK = pharmacokinetic.
$^a$For $C_{max}$, $AUC_{0-t}$, and $AUC_{0-\infty}$ geometric mean (CV %) are presented.
$^b$For $t_{max}$ median and (minimum-maximum) are presented.
$^c$For $t_½$, $CL_T$, $V_z$, and $V_{ss}$ arithmetic mean (CV %) are presented.
$^d$$CL_T$ and $V_z$ for IV treatment and $CL_r/F$ and $V_z/F$ for oral treatment.
$^e$$V_{ss}$ was calculated for IV treatment only.

TABLE 17

Summary of Statistical Analysis of Bioavailability (Cohort 4)

| PK Parameter | Geometric Least Square means | | | Percentage Test/Reference Estimate | (90% CI) |
|---|---|---|---|---|---|
| | Test | | Reference | | |
| $AUC_{0-t}$ | Oral 150 mg | 9777 | IV 150 mg | 13167 | 74.3 (67.0, 82.3) |
| $AUC_{0-\infty}$ | Oral 150 mg | 9881 | IV 150 mg | 13253 | 74.6 (67.2, 82.7) |

CI = confidence interval;
IV = intravenous;
PK = pharmacokinetic.
PK parameters were compared using a model with treatment (oral or IV), period and sequence a fixed factors, and subject within sequence as a random factor. The data were natural log transformed and back transformed after the analysis to obtain ratios.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. In addition, ranges and concentrations intermediate to any ranges and concentrations recited herein are also intended to be part of this application.

Patents, patent applications, publications, product descriptions, GenBank Accession Numbers, and protocols are cited throughout this application, the disclosures of which are incorporated herein by reference in their entireties for all purposes.

What is claimed is:

1. A method of treating Fabry disease in a subject, the method comprising intravenously administering to the subject a pharmaceutical composition comprising a co-formulation of recombinant human α-galactosidase A and 1-deoxygalactonojirimycin, or a pharmaceutically acceptable salt thereof, wherein the 1-deoxygalactonojirimycin or pharmaceutically acceptable salt thereof is administered at a dosage of about 0.1 to about 15 mg/kg and the recombinant human α-galactosidase A is administered at a dosage of about 0.1 to about 5 mg/kg.

2. The method of claim 1, wherein the dosage of 1-deoxygalactonojirimycin or salt thereof is selected from the group consisting of about 0.1, 0.3, 1, 3, and 10 mg/kg.

3. The method of claim 1, wherein the dosage of 1-deoxygalactonojirimycin or salt thereof is about 0.3 to about 10 mg/kg.

4. The method of claim 1, wherein the salt is a hydrochloride salt of 1-deoxygalactonojirimycin.

5. The method of claim 1, wherein the pharmaceutical composition is administered once per day, once every two days, once every three days, once every four days, once every five days, once every six days, or once every seven days.

6. The method of claim 1, wherein the co-formulation comprises:
about 0.5 to about 20 μM recombinant human α-galactosidase A; and
about 50 to about 20,000 μM 1-deoxygalactonojirimycin or salt thereof.

7. The method of claim 6, wherein the α-galactosidase A is present at a concentration selected from the group consisting of about 1.2, 2, 4, 8, and 12 μM; and the 1-deoxygalactonojirimycin or salt thereof is present at a concentration selected from the group consisting of about 449, 1,495, 4,490, 5 and 14,950 μM.

8. The method of claim 6, wherein the 1-deoxygalactonojirimycin and α-galactosidase A are present in a molar ratio of 1-deoxygalactonojirimycin to α-galactosidase A of between about 13,000:1 and about 50:1.

9. The method of claim 6, wherein the pharmaceutical composition is administered once per day, once every two days, once every three days, once every four days, once every five days, once every six days, or once every seven days.

10. The method of claim 1, wherein the pharmaceutical composition is administered every other week.

11. The method of claim 1, wherein the dosage of recombinant human α-galactosidase A is about 1 to about 3 mg/kg.

12. A method of treating Fabry disease in a subject, the method comprising intravenously administering to the subject a pharmaceutical composition comprising a co-formulation of recombinant human α-galactosidase A and 1-deoxygalactonojirimycin, or a pharmaceutically acceptable salt thereof, wherein the 1-deoxygalactonojirimycin or pharmaceutically acceptable salt thereof is administered at a dosage of about 0.3 to about 10 mg/kg and the recombinant human α-galactosidase A is administered at a dosage of about 0.1 to about 5 mg/kg, wherein the pharmaceutical composition is administered once every seven days or once every other week.

13. The method of claim 12, wherein the salt is a hydrochloride salt of 1-deoxygalactonojirimycin.

14. The method of claim 12, wherein the pharmaceutical composition is administered every other week.

15. The method of claim 12, wherein the dosage of 1-deoxygalactonojirimycin or salt thereof is about 0.3 mg/kg.

16. The method of claim 12, wherein the dosage of 1-deoxygalactonojirimycin or salt thereof is about 1 mg/kg.

17. The method of claim 12, wherein the dosage of 1-deoxygalactonojirimycin or salt thereof is about 3 mg/kg.

18. The method of claim 12, wherein the dosage of 1-deoxygalactonojirimycin or salt thereof is about 10 mg/kg.

19. The method of claim 12, wherein the dosage of recombinant human α-galactosidase A is about 1 to about 3 mg/kg.

* * * * *